(12) United States Patent
Stojevic et al.

(10) Patent No.: US 12,254,964 B2
(45) Date of Patent: Mar. 18, 2025

(54) QUANTUM CIRCUIT BASED SYSTEM CONFIGURED TO MODEL PHYSICAL OR CHEMICAL SYSTEMS

(71) Applicant: KUANO LTD., London (GB)

(72) Inventors: Vid Stojevic, London (GB); Matthias Bal, London (GB); Andrew Green, London (GB)

(73) Assignee: KUANO LTD., London (GB)

( * ) Notice: Subject to any disclaimer, the term of this patent is extended or adjusted under 35 U.S.C. 154(b) by 741 days.

(21) Appl. No.: 17/292,086

(22) PCT Filed: Nov. 7, 2019

(86) PCT No.: PCT/GB2019/053152
§ 371 (c)(1),
(2) Date: May 7, 2021

(87) PCT Pub. No.: WO2020/095051
PCT Pub. Date: May 14, 2020

(65) Prior Publication Data
US 2021/0398621 A1    Dec. 23, 2021

(30) Foreign Application Priority Data

Nov. 7, 2018   (GB) .................................... 1818154
Nov. 27, 2018  (GB) .................................... 1819279

(51) Int. Cl.
*G16C 20/70*   (2019.01)
*G06N 5/01*    (2023.01)
*G06N 10/00*   (2022.01)

(52) U.S. Cl.
CPC ............... *G16C 20/70* (2019.02); *G06N 5/01* (2023.01); *G06N 10/00* (2019.01)

(58) Field of Classification Search
None
See application file for complete search history.

(56) References Cited

U.S. PATENT DOCUMENTS

2018/0101784 A1   4/2018  Rolfe et al.
2021/0081804 A1*  3/2021  Stojevic .................. G16B 5/20

OTHER PUBLICATIONS

Giuseppe Carleo, Matthias Troyer, Solving the Quantum Many-Body Problem with Artificial Neural Networks (Year: 2016).*
E. Miles Stoudenmire and David J. Schwab, Supervised Learning With Quantum-Inspired Tensor Networks (Year: 2017).*
van Eersel, H, Tensor network methods for quantum simulation (Year: 2011).*
Aspuru-Guzik, A., et al., "Simulated Quantum Computation of Molecular Energies", Science, vol. 309, No. 5741, pp. 1704-1707 (Sep. 9, 2005) XP055713329.
Cao, Y., et al., "Potential of quantum computing for drug discovery", IBM Journal of Research and Development, vol. 62, No. 6, pp. 6:1-6:20 (Nov. 1, 2018) XP055711414.

(Continued)

*Primary Examiner* — Lina Cordero
(74) *Attorney, Agent, or Firm* — Saul Ewing LLP

(57) ABSTRACT

There is provided a quantum circuit based system configured to model infinite-size systems, in which one or more quantum circuits are configured as an infinite tensor network representation of quantum states of effectively infinite physical or chemical systems.

17 Claims, 65 Drawing Sheets

(56) References Cited

OTHER PUBLICATIONS

Carleo, G., et al., "Machine learningand the physical sciences", arxiv.org, Cornell Univ. Library (Mar. 25, 2019) XP081546191.
Dallaire-Demers, P-L., et al., "Quantum generative adversarial netowrks", Physical Review A, vol. 98, No. 1, p. 012324 (Jul. 1, 2018) XP055710380.
Huggins, W., et al., "Towards Quantum Machine Learning with Tensor Networks", arxiv.org, Cornell Univ. Library, Retrieved from the INternet: URL:https://arxiv.org/pdf/1803.11537v2.pdf; (Jul. 31, 2018) XP081107742.
Jia, Z-A., et al., "Quantum Neural Network States: A Brief Review of Methods and Applications", arxiv.org, Cornell Univ. Library (Feb. 26, 2019) XP081016464.
Orus, R., "A practical introduction to tensor networks: Matrix product states and projected entangled pair states", Annals of Physics, JY, NY, vol. 349, pp. 117-158 (Jun. 19, 2014) XP029041554.
Ran, S-J., et al., "Lecture Notes of Tensor Network Contractions", arxiv.org, Cornell Univ.Library; Retrieved from the Internet: URL:https://arxiv.org/pdf/1708.09213v4.pdf (Jul. 27, 2019) XP081449936.
Ran, S-J., et al., "Review of Tensor Network Contraction Approaches", arxiv.org, Cornell Univ. Library, Retrieved from the Internet: URL:https://arxiv.org/pdf/1708.09213v3.pdf (Aug. 30, 2017) XP081315574.
Schutt, K.T., et al., "Quantum-chemical insights from deep tensor neural networks", Nature Communications, vol. 8, No. 1 (Jan. 9, 2017) XP055711416.
Schuyler Fried, E., et al., "qTorch: The Quantum Tensor Contraction Handler", arxiv.org, Cornell Univ. Library, (Sep. 12, 2017) XP080820281.
Verdon, G., et al., "A quantum algorithm to train neural networks using low-depth circuits", arxiv.org, Cornell Univ. Library; Retrieved from the Internet: URL:https://arxiv.org/pdf/1712.05304v1.pdf; (Dec. 14, 2017) XP0800846185.
International Search Report, dated Jul. 20, 2020, issued in International Application No. PCT/GB2019/053152.

Benedetti, et al., "Adversarial quantum circuit learning for pure state approximation". In: ArXiv e-prints (Jun. 2018). arXiv: 1806.00463 [quant-ph].
Chan, et al., "The Density Matrix Renormalization Group in Quantum Chemistry", Annual Review of Physical Chemistry 62, 465-481 (2011).
Grant, et al., "Hierarchical quantum classifiers". In: ArXiv e-prints (Apr. 2018). arXiv: 1804.03680 [quant-ph].
Hachmann, "Ab initio density matrix renormalization group methodology and computational transition metal chemistry", Cornell University (2010).
Hallam, et al., "Compact neural networks based on the multiscale entanglement renormalization ansatz" ArXiv e-prints (2017).
Han, et al., "Unsupervised Generative Modeling Using Matrix Product States". In: Physical Review X 8.3, 031012 (Jul. 2018), p. 031012. DOI: 10.1103/PhysRevX. 8.031012. [cond-mat.stat-mech].
Havlicek, et al., "Supervised learning with quantum enhanced feature spaces". In: ArXiv e-prints (Apr. 2018). arXiv: 1804.11326 [quant-ph].
Levine, et al., "Quantum Entanglement in Deep Learning Architectures" Phys. Rev. Lett. 122, 065301 (2019).
Neil, et al., "Exploring Deep Recurrent Models with Reinforcement Learning for Molecule Design" ICLR 2018 Conference Blind Submission https://openreview.net/pdf?id=Bk0xil1Dz.
Olivares-Amaya, et al., "The ab-initio density matrix renormalization group in practice", Journal of Chemical Physics 142, 34102 (2015).
Stoudenmire, et al., "Supervised Learning with Quantum-Inspired Tensor Networks". In: ArXiv e-prints (May 2016). arXiv: 1605 . 05775 [stat.ML].
White, et al., "Ab initio quantum chemistry using the density matrix renormalization group", Journal of Chemical Physics 110, 4127-4130 (1999).
Wouters, et al., "The density matrix renormalization group for ab initio quantum chemistry", European Physical Journal D 68 (2014) 10.1140/epjd/e2014-50500-1.

* cited by examiner $$|\psi[A]\rangle = \sum_{i_1,i_2,\ldots,i_N}^{d} v_L^\dagger A_1^{i_1} A_2^{i_2} \cdots A_N^{i_N} v_R |i_1, i_2, \ldots, i_N\rangle, \quad (1)$$

FIGURE 1

$$A^{i_n} \to G_{n-1} A^{i_n} G_n^{-1}, \quad (2)$$

$$\dot{A}^*(t) = \underset{\dot{A}(t)}{\arg\min} \left\| \left| \Phi(\dot{A}, A) \right\rangle + i\hat{H}(t) \left| \Psi(A(t)) \right\rangle \right\|, \quad (3)$$

$$\begin{aligned} \left| \Phi(dA, A) \right\rangle &= \sum_{i_1,\cdots,i_N} v_L^\dagger dA_1^{i_1} A_2^{i_2} \cdots A_N^{i_N} v_R \left| i_1, i_2, \cdots, i_N \right\rangle \\ &+ \sum_{i_1,i_2,\cdots,i_N}^{d} v_L^\dagger A_1^{i_1} dA_2^{i_2} \cdots A_N^{i_N} v_R \left| i_1, i_2, \cdots, i_N \right\rangle \\ &+ \cdots \\ &+ \sum_{i_1,i_2,\cdots,i_N}^{d} v_L^\dagger A_1^{i_1} A_2^{i_2} \cdots dA_N^{i_N} v_R \left| i_1, i_2, \cdots, i_N \right\rangle \\ &:= \sum_\alpha dA^\alpha \frac{\partial}{\partial A^\alpha} \left| \Psi(A) \right\rangle \equiv \sum_\alpha dA^\alpha \left| \partial_\alpha \Psi(A) \right\rangle. \end{aligned} \quad (4)$$

FIGURE 3

$$dA^{i_n} \to dA^{i_n} + X_{n-1}A^{i_n} - A^{i_n}X_n, \quad (5)$$

$$E := \sum_i A^i \otimes \vec{A}^i, \quad (6)$$

FIGURE 5

$$\langle \psi[A] | \hat{O} | \psi[A] \rangle = \sum_{\substack{i_1,i_2,\ldots,i_n \\ j_1,j_2,\ldots,j_n}}^{d} \left( l | O_{i_1\cdots i_n}^{j_1\cdots j_n} \left( A^{i_1} \cdots A^{i_n} \right) \otimes \left( \overline{A}_{j_1} \cdots \overline{A}_{j_n} \right) | r \right). \quad (7)$$

$$A^i \rightarrow G A^i G^{-1}, \quad (8)$$

$$\left( l | \sum_i dA^i \otimes \overline{A}^i = 0 \quad \text{or} \quad \sum_i dA^i \otimes \overline{A}^i | r \right) = 0, \quad (9)$$

$$CA_R = A_L C, \quad (10)$$

FIGURE 6

$$A_L^\dagger A_L = 1 \quad A_R A_R^\dagger = 1$$
$$A_L C = C A_R \quad A_R^\dagger C^\dagger C A_R = C^\dagger C \quad A_L C C^\dagger A_L^\dagger = C C^\dagger \tag{11}$$
$$\rho_l = C^\dagger C \quad \rho_r = C C^\dagger$$
$$A_M := A_L C = C A_R \ .$$

$$\text{while}(C' \not\approx C'') \{ \tag{12}$$
$$[C'', A_R] = \text{qr}(A_L C')$$
$$C' = C'''$$
$$\}.$$

$$\Phi[C, A_R; A_L] = \|A_L C - C A_R\|^2 \ . \tag{13}$$

FIGURE 7

$$G_{\bar{\alpha}\beta} := \langle \partial_{\bar{\alpha}} \Psi(A) | \partial_{\beta} \Psi(A) \rangle, \qquad (14)$$

$$\sum_{\beta} G_{\bar{\alpha}\beta} \dot{A}^{\beta} = -i \langle \partial_{\bar{\alpha}} \Psi(A) | \hat{H}(t) | \Psi(A(t)) \rangle, \qquad (15)$$

$$\sum_{\bar{\alpha},\beta} \overline{dA}^{\alpha} G_{\bar{\alpha}\beta} dA^{\beta} = |Z| (l dA \otimes d\vec{A}' | r), \qquad (16)$$

$$G = \rho_l \otimes \rho_r. \qquad (17)$$

FIGURE 8

$$\sum_{\vec{\alpha}} d\vec{A}^{\vec{\alpha}} \langle \partial_{\vec{\alpha}} \Psi(A) | \hat{H}(t) | \Psi(A(t)) \rangle =$$
$$|\mathbb{Z}| \Big( \big( (l\|H_{d\vec{A}^t A}^{AA}|r) + (l\|H_{A d\vec{A}^t}^{AA}|r) \big)$$
$$+ (l\|H_{AA}^{AA}(1-E)^{PI}(A \otimes d\vec{A}^t)|r) \Big).$$

(18)

$$Ax = b$$

(19)

$$\frac{1}{2} x^T A x - b^T x - c.$$

$$\min_{\tilde{A}_L} \|\tilde{A}_L \hat{C} - \tilde{A}_M\|, \quad (21)$$

$$\hat{C} = C + dt \frac{dC}{dt} \quad (22)$$

$$\tilde{A}_M := A_L C + dt \frac{d}{dt}(A_L C). \quad (23)$$

FIGURE 10

$$\tilde{A}_L CC^\dagger = \tilde{A}_M C^\dagger, \quad (24)$$

$$\tilde{A}_M C^\dagger = UDV^\dagger$$
$$= UV^\dagger(VDV^\dagger). \quad (25)$$

$$\tilde{A}_L = UV^\dagger, \quad (26)$$

$$\tilde{A}_L \tilde{z} - \tilde{A}_M = \tilde{A}_L \tilde{q}\tilde{r} - \tilde{Q}\tilde{R}. \quad (27)$$

$$\tilde{A}_L \tilde{q} = \tilde{Q}$$
$$\tilde{A}_L = \tilde{Q}\tilde{q}^\dagger. \quad (28)$$

FIGURE 12

| Dataset | Dataset size | Task type (# of tasks) | Model | Accuracy |
|---|---|---|---|---|
| ESOL | 1128 | Regression (1) | Weave | 87,731 |
| | | | GTN | 89,211 |
| QM7 | 7165 | Regression (1) | Weave | 65,19 |
| | | | GTN | 67,15 |
| QM8 | 10000 | Regression (16) | Graph Conv. | 58,979 |
| | | | GTN | 61,193 |
| MUV | 93127 | Classification (17) | Graph Conv. | 76,585 |
| | | | GTN | 80,06 |

FIGURE 33

$$\Psi^{i_1 i_2 \cdots i_N} = \sum_{i_1=1}^{d} \sum_{i_2=1}^{d} \cdots \sum_{i_N=1}^{d} v_L^\dagger A_1^{i_1} A_2^{i_2} \cdots A_N^{i_N} v_R$$

FIGURE 38

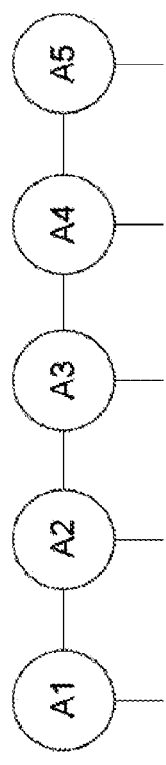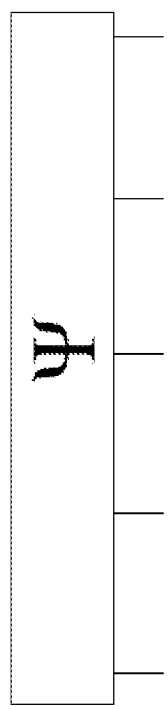
FIGURE 39

$$W^{i_1,i_2,\ldots,i_n}_{j_1,j_2,\ldots,j_n} = \sum_{\alpha_1,\alpha_2,\ldots,\alpha_{n-1}} A^{i_1}_{j_1,\alpha_1} A^{\alpha_1,i_1}_{j_1,\alpha_2} \cdots A^{\alpha_{n-1},i_n}_{j_n}.$$

FIGURE 42

| Network | Parameters (FC Layer) | Parameters (Total) | Compression (FC layer) | Compression (Total) | Accuracy | Standard Deviation |
|---|---|---|---|---|---|---|
| FC-1 | 17,040,000 | 17,336,640 | 1 | 1 | 88.9 | 0.2 |
| FC-2 | 21,440 | 318,080 | 795 | 54.5 | 86.5 | 0.8 |
| MERA | 1192 | 297,832 | 14,295 | 58.21 | 88.5 | 0.1 |
| TT | 1312 | 297,952 | 12,987 | 58.19 | 87.9 | 0.2 |

FIGURE 44

| Network | Parameters (FC Layer) | Parameters (Total) | Compression (FC Layer) | Compression (Total) | Accuracy | Standard Deviation |
|---|---|---|---|---|---|---|
| FC-1 | 17,045,760 | 17,342,400 | 1 | 1 | 61.8 | 0.7 |
| FC-2 | 48,000 | 344,640 | 355 | 50.3 | 53.4 | 0.6 |
| MERA | 6952 | 303,592 | 2451 | 57.12 | 58.4 | 0.6 |
| TT | 7072 | 303,712 | 2410 | 57.10 | 57.9 | 0.6 |

FIGURE 45

Variational Auto-Encoder (VAE)

Appendix 2 equations and schematics $$H(\mathbf{R}, \mathbf{r})\Psi(\mathbf{R}, \mathbf{r}) = E(\mathbf{R})\Psi(\mathbf{R}, \mathbf{r}), \quad (1)$$

$$H(\mathbf{R}, \mathbf{r}) = -\frac{1}{2}\sum_{i=1}^{N}\nabla_i^2 - \frac{1}{2}\sum_{A=1}^{M}\frac{1}{M_A}\nabla_A^2 - \sum_{i=1}^{N}\sum_{A=1}^{M}\frac{Z_A}{r_{iA}} + \sum_{i=1}^{N}\sum_{j>i}^{N}\frac{1}{r_{ij}} + \sum_{A=1}^{M}\sum_{B>A}^{M}\frac{Z_A Z_B}{R_{AB}}, \quad (2)$$

$$H_{elec}(\mathbf{R}, \mathbf{r})\chi(\mathbf{R}, \mathbf{r}) = E_{elec}(\mathbf{R})\chi(\mathbf{R}, \mathbf{r}) \quad (3)$$

$$H_{elec}(\mathbf{R}, \mathbf{r}) = -\frac{1}{2}\sum_{i=1}^{N}\nabla_i^2 - \sum_{i=1}^{N}\sum_{A=1}^{M}\frac{Z_A}{r_{iA}} + \sum_{i=1}^{N}\sum_{j>i}^{N}\frac{1}{r_{ij}}, \quad (4)$$

FIGURE 52

$$\Psi(x_1, x_2, \ldots, x_N) = \frac{1}{\sqrt{N!}} \begin{vmatrix} \chi_1(x_1) & \chi_2(x_1) & \cdots & \chi_N(x_1) \\ \chi_1(x_2) & \chi_2(x_2) & \cdots & \chi_N(x_2) \\ \vdots & \vdots & \ddots & \vdots \\ \chi_1(x_N) & \chi_2(x_N) & \cdots & \chi_N(x_N) \end{vmatrix} \quad (5)$$

$$\equiv |\chi_1, \chi_2, \ldots, \chi_N\rangle, \quad (6)$$

where the $\chi_i(x), \forall i \in \{1, 2, \ldots, N\}$ are a set of one-electron spin-orbital wave functions.

FIGURE 53

$$|\Psi_{CI}\rangle = (1+T_1+T_2+\ldots)|\Psi_{HF}\rangle.$$

(9)

$$\rho = |\Psi(x_1, x_2, \ldots, x_N)\rangle \langle \Psi(x_1, x_2, \ldots, x_N)|, \quad (10)$$

$$\rho^{(1)}(x_1, x_1') = N \int \Psi^*(x_1', x_2, \ldots, x_N) \Psi(x_1, x_2, \ldots, x_N)\, dx_2 \ldots dx_N, \quad (11)$$

$$\rho^{(1)}(x_1) = N \int \Psi^*(x_1, x_2, \ldots, x_N) \Psi(x_1, x_2, \ldots, x_N)\, dx_2 \ldots dx_N. \quad (12)$$

$$P^{(1)}(\mathbf{r}_1) = \int \rho^{(1)}(\mathbf{r}_1; s_1)\, ds_1. \quad (13)$$

$$\rho^{(2)}(x_1, x_2, x_1', x_2') = N(N-1) \int \Psi^*(x_1', x_2', \ldots, x_N) \Psi(x_1, x_2, \ldots, x_N)\, dx_3 \ldots dx_N, \quad (14)$$

$$\rho^{(2)}(x_1, x_2) = N(N-1) \int \Psi^*(x_1, x_2, \ldots, x_N) \Psi(x_1, x_2, \ldots, x_N)\, dx_3 \ldots dx_N. \quad (15)$$

FIGURE 57

$$\rho^{(1)}(\mathbf{x}_1, \mathbf{x}'_1) = \sum_{i,j} \rho^{(1)}_{ij} \phi_i(\mathbf{x}_1) \phi^*_j(\mathbf{x}'_1). \quad (16)$$

$$\rho^{(1)}(\mathbf{x}_1, \mathbf{x}'_1) = \sum_i n_i \phi^{NSO}_i(\mathbf{x}_1) \phi^{*NSO}_j(\mathbf{x}'_1). \quad (17)$$

$$p^{(1)}(\mathbf{r}_1, \mathbf{r}'_1) = \sum_i n_i \phi^{NO}_i(\mathbf{r}_1) \phi^{*NO}_j(\mathbf{r}'_1). \quad (18)$$

Atomic orbital → NHO → NBO → NLMO → Molecular orbital, (19)

FIGURE 58

$$|\Psi_{CAS-CI}\rangle = \sum_{n_1,\ldots,n_L} C_{n_1,\ldots,n_L} |n_1 n_2 \ldots n_L\rangle, \quad (20)$$

$$\epsilon = |||\Psi\rangle - |\tilde{\Psi}\rangle||^2 = 1 - \sum_{\alpha=1}^{D} w_\alpha, \quad (21)$$

$$S_i = -\sum_{\alpha=1}^{4} w_{\alpha,i} \ln w_{\alpha,i} \quad (22)$$

$$S_{ij} = -\sum_{\alpha=1}^{16} w_{\alpha,ij} \ln w_{\alpha,ij} \quad (23)$$

$$I_{ij} = \frac{1}{2}(S_i + S_j - S_{ij})(1 - \delta_{ij}) \quad (24)$$

FIGURE 62

| model | type | ordering | seq.? | components | remarks |
|---|---|---|---|---|---|
| GraphVAE | VAE | ordered | no | atoms | poor results |
| Our Attempt | VAE | covariant | no | atoms | convergence issues |
| Junction Tree VAE | VAE | arbitrary | yes | clusters | two-step process |
| Constraint graph VAE | VAE | covariant | yes | atoms | |
| MolGAN | GAN | ordered | no | atoms | mode collapse |
| GCPN | RL | arbitrary | yes | atoms (flexible) | strong results |

Table 1: Overview of different models, their architectures and charateristics.

FIGURE 66

QUANTUM CIRCUIT BASED SYSTEM CONFIGURED TO MODEL PHYSICAL OR CHEMICAL SYSTEMS

CROSS REFERENCE TO RELATED APPLICATIONS

This application claims the priority of PCT/GB2019/053152, filed on Nov. 7, 2019, which claims priority to GB Application No. GB 1818154.5, filed on Nov. 7, 2018; and GB Application No. GB 1819279.9, filed on Nov. 27, 2019, the entire contents of each of which being fully incorporated herein by reference.

BACKGROUND OF THE INVENTION

1. Field of the Invention

The field of the invention relates to a quantum circuit based system configured to model effectively infinite physical or chemical systems, and related methods.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Background of the Invention

In small molecule drug design, after a disease mechanism has been identified, a new journey through chemical space is initiated. The challenge is to identify a candidate molecule that binds to a specified target protein in order to cure, prevent entirely, or mitigate the symptoms of the disease—all the while having minimal negative side effects for the patient. The process starts by filtering millions of molecules, in order to identify a hundred or so promising leads with high potential to become medicines. Around 99% of selected leads fail later in the process, both due to the inability of current technologies to accurately predict their impact on the body, and the limited pool from which they were sampled. Currently the process takes approximately 15 years and costs $2.6 bn.

The very low accuracy achieved is due in part to the problem of representation of the molecules. Molecules are often represented in a simplified model using strings or graphs where the wave function and quantum properties should be taken into account. However, the description of molecular quantum states involves vector spaces whose dimension is exponentially large in the number of constituent atoms.

Another key challenge lies in the astronomical size of the search space: there are an estimated $10^{60}$ possible small drug-like molecules.

The pharma industry has largely not been able to address these challenges with truly novel methods, and as legacy approaches to discovering new drugs are drying-up, so-called "Eroom's Law" is observed: a staggering drop in R&D drug development efficiencies by a factor of one half every nine years.

Infinite tensor networks can be used to represent many body quantum states that have (effectively) infinite spatial extent, which includes molecular or atomic systems with repeating structures. The full description of the system involves a component describing the quantum information/entanglement of the region in which observables of interest reside, as well as a description of the environment, which describes the integrated effect of the rest of the infinitely large system.

Methods for periodic systems, such as iMPS, iPEPS, or uniform cMPS are regularly used to simulate effectively infinite systems, such as spin systems, gasses of strongly interacting particles, or ordered solid-state systems (crystal structures). Usually one is constrained to lower dimensions (1 or 2 spatial dimensions), as higher dimensional calculations become prohibitively expensive, and in many cases are expected to be infeasible on classical computers.

Additionally, the simulation of infinite or large-scale problems, such as the quantum states of large-sized molecule still need to be achieved with desired accuracies much more efficiently that what classical methods offer.

The present invention addresses the above vulnerabilities and also other problems not described above.

SUMMARY OF THE INVENTION

The invention is a quantum circuit based system configured to model infinite-size systems, in which one or more quantum circuits are configured as an infinite tensor network representation of quantum states of effectively infinite physical or chemical systems.

Another aspect is a method of modeling infinite-size systems, in which quantum circuits(s) are configured as an infinite tensor network representation of quantum states of (effectively) infinite physical or chemical systems.

Another aspect is a drug-like molecule identified, selected or optimized using the system or the method above.

Another aspect is a material or other substance identified, selected or optimized using the system or the method above.

BRIEF DESCRIPTION OF THE FIGURES

Aspects of the invention will now be described, by way of example(s), with reference to the following Figures, which each show features of the invention:

FIG. 1 reproduces equation (1).
FIG. 3 reproduces equations (2) to (4).
FIG. 5 reproduces equations (5) and (6).
FIG. 6 reproduces equations (7) to (10).
FIG. 7 captures equations (11) to (13).
FIG. 8 reproduces equations (14) to (17).
FIG. 9 reproduces equations (18) to (20).
FIG. 10 reproduces equations (21) to (23).
FIG. 12 reproduces equations (24) to (28).

FIG. 33 shows a table of results.

FIG. 38 shows is a diagram showing an example of a decomposition of a tensor into a matrix product state.

FIG. 39 shows a schematic decomposition of a mode-5 tensor as a matrix product state.

FIG. 42 shows equation (1).

FIG. 44 shows a table of results.

FIG. 45 shows a table of results.

FIG. 52 shows equations (1) to (4) from Appendix 3.

FIG. 53 shows equations (5) to (6) from Appendix 3.

FIG. 57 shows equations (10) to (15) from Appendix 3.

FIG. 58 shows equations (16) to (19) from Appendix 3.

FIG. 62 shows equations (12) to (14) from Appendix 3.

FIG. 66 is a summary overview of generative models.

DETAILED DESCRIPTION

Figure 2:
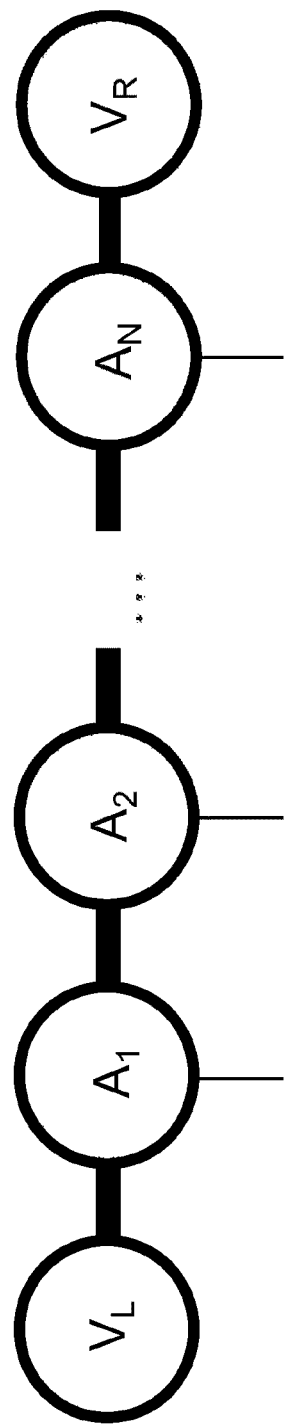
FIG. 2 shows a graphical representation of FIG. 1.

A description of both the environment and the local region of interest of an infinite tensor network is computed on a quantum computer by optimising appropriate quantum circuits. The methods are also amenable to classical data that has a naturally repeating structure or is effectively infinite in extent. The method can be used for optimising a single system of infinite-size (e.g. its energy or another property), or to train a machine learning model on a dataset of such systems. We note that classical tensor network methods for physical or chemical systems of infinite extent have been studied extensively over the past 10+ years—both the quantum computing implementation and the machine learning generalisation constitute novel material.

Key Features

Quantum circuits(s) configured as an infinite tensor network representation of quantum states of (effectively) infinite physical or chemical systems.

Quantum circuits(s) configured as an infinite tensor network representation of a classical system with a naturally repeating structure or having an (effectively) infinite extent.

Machine learning based method applied to a dataset of infinite tensor network representations of quantum states of (effectively) infinite physical or chemical systems or for classical data with a naturally repeating structure or having an (effectively) infinite extent. [Machine learning on infinite system] (see Appendix 1).

Using quantum computers to describe an infinite tensor network.

Where the infinite tensor network is used to represent the repeating crystal structure of a physical system or a classical system with a naturally repeating structure or having an (effectively) infinite extent.

Quantum algorithm for calculating the environment of an infinite tensor network representation of molecular quantum states of infinite or large sized molecule(s).

Quantum algorithm for optimising a property (e.g. energy or the expectation value of an operator) of an infinite tensor network representation of a quantum state of (effectively) infinite physical or chemical systems or of a classical system with a naturally repeating structure or having an (effectively) infinite extent.

Method of computing and tuning the environment of an infinite tensor network by sampling the output of a quantum circuit configured as an infinite tensor network.

- Method of computing and tuning a property of an infinite tensor network by sampling the output of a quantum circuit configured as an infinite tensor network.
- Machine learning system implemented on a quantum computer with quantum circuits configured as infinite tensor networks.
- Machine learning network represented as a quantum machine learning circuit.
- Machine learning system is a quantum machine learning circuit based on an infinite tensor network, and obtained by embedding the infinite tensors in the networks into unitary gates.
- Machine learning method used to optimise chemical properties for candidate drug-like molecules, and in the condensed matter and material science context (e.g. energy transfer, organic LED and photovoltaic material properties, melting point, log P, log D, lipophilicity and permeability, to name a few concrete examples).

A method based on infinite tensor networks to implement machine learning and many body quantum physics algorithms for systems of infinite size on quantum computers is presented.

1. High-Level Overview

This document describes a method for optimising translation invariant tensor networks for infinitely large systems (i.e. in the thermodynamic limit) on quantum computers.

Applications include both algorithms for solving quantum mechanical problems, like finding the ground state of a specific Hamiltonian, time evolution simulations based on the inverse free classical methods [Tangent-space methods for uniform matrix product states: https://arxiv.org/pdf/1810.07006.pdf] (we describe the implementation of this on quantum computers), as well as machine learning applications.

In Section 1.1 we provide some background information on one dimensional tensor networks, specifically both finite and infinite matrix product states. We also provide a brief review of infinite tensor networks in more than one dimension. Quantum algorithms generalising the classical methods for optimising iMPS, iTDVP, as well as higher dimensional algorithms.

1.1 Review of Finite and Infinite MPS

A matrix product state (MPS) [https://arxiv.org/pdf/1810.07006.pdf] is a state of the form:

$$|\Psi[A]\rangle = \sum_{i_1, i_2, \cdots, i_N}^{d} v_L^\dagger A_1^{i_1} A_2^{i_2} \cdots A_N^{i_N} v_R |i_1, i_2, \cdots, i_N\rangle, \quad (1)$$

where d is the number of physical (spin) degrees of freedom, and $A^{i\alpha}$ is a $D_{A-1} \times D_A$ matrix, while $v_L$ and $v_R$ are vectors of dimensionality $D_0$ and $D_N$ respectively. The dimension of these internal/virtual indices is referred to as the bond dimension.

FIG. 1 reproduces equation (1).

The open boundary condition Ansatz is presented here for the sake of concreteness—the periodic boundary condition MPS Ansatz corresponds to taking a trace in place of contraction by $v_L^\dagger$ and $v_R$. Graphically the state (1) can be represented as shown in FIG. 2, where the thick lines represent the internal bond dimension indices, while the physical spins are denoted by the thin lines with 'uncontracted' ends. Here and in what follows we will not graphically depict any variation in the dimensionality of physical or bond indices.

Transformations of the MPS matrices of the form:

$$A^{i_n} \to G_{n-1} A^{i_n} G_n^{-1}, \quad (2)$$

where $G_n$, $G_{n-1} \in GL(D, \mathbb{C})$ [https://arxiv.org/pdf/1810.07006.pdf] leave the state invariant, and are referred to as gauge transformations. The gauge transformations of the boundary (co)-vectors are given by $v_L^\dagger \to v_L^\dagger G_0^{-1}$, and $v_R \to G_N v_R$.

Applying the time-dependent variational principle (TDVP) to the MPS variational class [2, 3] yields:

$$\dot{A}^*(t) = \arg \min_{\dot{A}(t)} \left\| |\Phi(\dot{A}, A)\rangle + i\hat{H}(t)|\Psi(A(t))\rangle \right\|, \quad (3)$$

where the object $|\Phi(dA, A)\rangle$ is given by:

$$|\Phi(dA, A)\rangle = \sum_{i_1, \cdots, i_N} v_L^\dagger dA_1^{i_1} A_2^{i_2} \cdots A_N^{i_N} v_R |i_1, i_2, \cdots, i_N\rangle + \quad (4)$$

$$\sum_{i_1, i_2, \cdots, i_N}^{d} v_L^\dagger dA_1^{i_1} A_2^{i_2} \cdots A_N^{i_N} v_R |i_1, i_2, \cdots, i_N\rangle +$$

$$\cdots\cdots +$$

$$\sum_{i_1, i_2, \cdots, i_N}^{d} v_L^\dagger dA_1^{i_1} A_2^{i_2} \cdots A_N^{i_N} v_R |i_1, i_2, \cdots, i_N\rangle$$

$$:= \sum_\alpha dA^\alpha \frac{\partial}{\partial A^\alpha} |\Psi(A)\rangle \equiv \sum_\alpha dA^\alpha |\partial_\alpha \Psi(A)\rangle.$$

FIG. 3 reproduces equations (2) to (4).

The $\alpha$ index on the last line combines physical, virtual, and site indices. Unlike elements in the variational class of MPS, the objects $|\Phi(dA, A)\rangle$ form a vector space—and are in fact tangent vectors to the MPS manifold [3, 4]. The gauge invariance of MPS eq. (2) can be shown to imply the invariance of tangent states under $$dA^{i_n} \to dA^{i_n} + X_{n-1} A^{i_n} - A^{i_n} X_n, \quad (5)$$

where the matrices X live in the Lie algebra gl(D;C) of the gauge group. One can use this freedom to improve the numerical stability of a particular problem, for example the integration of equation (3).

Figure 4:
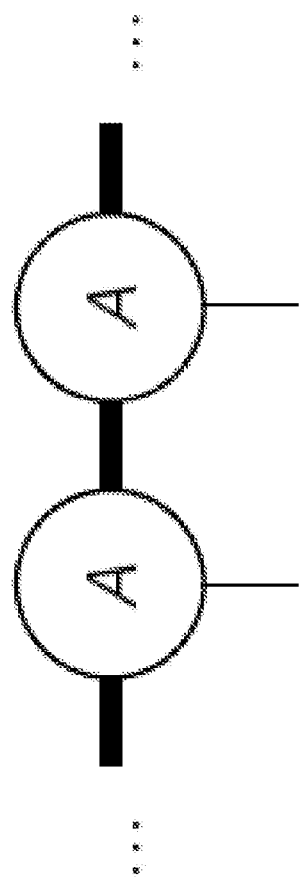
FIG. 4 shows the graphical representation of a iMPS.

The novel methods described in this text are based on working with MPS directly in the thermodynamic limit ($N \to \infty$). We will use a translation invariant Ansatz, taking the MPS tensors to be position independent (which clearly requires a constant bond dimension D). We refer to the class of such states as infinite MPS (iMPS). FIG. 4 shows the graphical representation of a iMPS.

The largest eigenvalue of the iMPS transfer matrix E, $$E := \sum_i A^i \otimes \bar{A}^i, \quad (6)$$

needs to be fixed to unity in order to ensure finite normalisation. The state norm is given by (l|r), where (l| and |r) are respectively the left and right eigenvectors of E corresponding to eigenvalue 1, and since the eigenvectors can be rescaled freely the state can always be normalised to one.

FIG. 5 reproduces equations (5) and (6).

The expectation value of a local operator acting on n sites can now be written as:

$$\langle \Psi[A] | \hat{O} | \Psi[A] \rangle = \tag{7}$$

$$\sum_{\substack{i_1, i_2, \ldots, i_n, \\ j_1, j_2, \ldots, j_n}}^{d} (l | O_{i_1 \ldots i_n}^{j_1 \ldots j_n} (A^{i_1} \ldots A^{i_n}) \otimes (\overline{A}_{j_1} \ldots \overline{A}_{j_n}) | r).$$

The cost of computing this object, using the optimal sequence of contractions, can be seen to scale as $O(ndD^3)$ on a classical computer. Quantum generalisations of MPS algorithms scale, as we will see, as $O(\log(D))$. Therefore, calculations with high bond dimensions that would classically require exponential resources become feasible on a quantum computer.

The iMPS parametrisation is invariant under gauge transformations:

$$A^i \to G A^i G^{-1}, \tag{8}$$

and these can be used to set either $\rho_l=1$ or $\rho_r=1$ (but in general not both), where $\rho_l$ is the $D^2$ dimensional co-vector (|l⟩ reshaped to a D×D matrix, and similarly for $\rho_r$. The corresponding gauge transformations in the tangent plane (see (5)) are given by $dA^i \to dA^i + XA^i - A^i X$, and this gauge freedom can be used to set either:

$$\left( l \left| \sum_i dA^i \otimes \overline{A}^i = 0 \text{ or } \sum_i dA^i \otimes \overline{A}^i \right| r \right) = 0, \tag{9}$$

but again in general not both. These are referred to as, respectively, the left and right tangent space gauge conditions, and we'll denote the corresponding MPS tensors as $A_L$ and $A_R$.

In modern MPS algorithms, fixed points (or environments) of translation invariant MPS are no longer calculated by constructing the transfer matrix (double-layer) to find its eigenvectors. Single-layer algorithms have been developed which find the fixed point by acting only on the ket (another application of single-layer algorithms is the use of one-dimensional algorithms to approximately contract two-dimensional systems. There, having a single- rather than a double-layer algorithm makes an enormous difference in numerical cost). The equation to be approximated as accurately as possible in these algorithms is $$CA_R = A_L C, \tag{10}$$

which is referred to as a pulling-through equation (C is being pulled through the other tensor) because of its similarity to matrix product operator (MPO) pulling-through equations appearing in the framework of topologically-ordered PEPS and MPO algebras [5, 6].

FIG. 6 reproduces equations (7) to (10).

1.1.1 Calculating the Environment: Solving the Pulling-Through Equation on a Classical Computer Here we describe a classical algorithm [7] to find AL and a C (or AR and C) given an AR (or AL) that satisfy the pulling-through equation (10). This is a more useful starting point for determining the environment on a classical computer, than approaches that calculate $\rho_l$ or $\rho_r$ directly [2].

First, some definitions and basic relations:

$$A_L^\dagger A_L = 1 \; A_R A_R^\dagger = 1$$

$$A_L C = C A_R \; A_R^\dagger C^\dagger C A_R = C^\dagger C \; A_L C C^\dagger A_L^\dagger = C C^\dagger$$

$$\rho_l = C^\dagger C \; \rho_r = C C^\dagger$$

$$A_M := A_L C = C A_R. \tag{11}$$

Given an $A_L$ one can calculate both C and $A_R$ from an iterative inverse-free procedure. Schematically, input $A_L$ and some initial (random or recycled from parts of an algorithm that might subsume this method) C into $$\text{while}(C' \neq C'') \tag{12}$$

$$\{[C'', A_R] = qr(A_L C')$$

$$C' = C''\},$$

Where qr refers to a QR-decomposition.

When $C'=C''$ up to some desired numerical accuracy, the algorithm outputs $C=C''$ and $A_R$, satisfying $A_L C = C A_R$ up to said accuracy.

In transitioning to the quantum algorithm it will be useful to think of the above as a procedure for minimising the cost function $$\Phi[C, A_R; A_L] = \|A_L C - C A_R\|^2. \tag{13}$$

FIG. 7 reproduces equations (11) to (13).

1.1.2 Time Evolution for iMPS

The Gram matrix, given by:

$$G_{\overline{\alpha}\beta} := \langle \partial_{\overline{\alpha}} \psi(A) | \partial_\beta \psi(A) \rangle, \tag{14}$$

defines a natural metric on the iMPS manifold [4]. The TDVP equations can be formally expressed as:

$$\sum_\beta C_{\alpha\beta} \dot{A}^\beta = -i \langle \partial_\alpha \Psi(A) | \hat{H}(t) | \Psi(A(t)) \rangle. \tag{15}$$

Where $\dot{A}$ refers to the time derivative of A.

Imposing either the left or right tangent gauge condition (9) simplifies the equations significantly, and is in fact necessary to eliminate infinities in (15) stemming from transformations along the iMPS state itself. The expression for the overlap of two tangent vectors takes the simple form:

$$\sum_{\alpha, \beta} \overline{A}^{\prime \overline{\alpha}} G_{\overline{\alpha}\beta} dA^\beta = |\mathbb{Z}|(l | dA \otimes d\overline{A}' | r), \tag{16}$$

since the left (or right) gauge condition implies that all terms for which the dA and $d\overline{A}'$ tensors are not at the same site are zero. The Gram matrix then takes the simple form:

$$G = \rho_l \otimes \rho_r \tag{17}$$

FIG. 8 reproduces equations (14) to (17).

The nature of the right hand side of (15) is elucidated by contracting it with $d\overline{A}'^{\alpha}$:

$$\sum_{\alpha} d\overline{A}'^{\alpha} \langle \partial_{\overline{\alpha}} \Psi(A) | \hat{H}(t) | \Psi(A(t)) \rangle = \qquad (18)$$

$$|\mathbb{Z}|((l|H^{AA}_{d\overline{A}'\overline{A}}|r) + (l|H^{AA}_{\overline{A}d\overline{A}'}|r) + (l|H^{AA}_{\overline{A}\overline{A}}(1-E)^{PI}(A \otimes d\overline{A}')|r)).$$

Here $$H \frac{A}{A} \frac{A}{dA'}$$

for example, stands for the contraction of the two 'ket' indices of a local term in the Hamiltonian, which is assumed to be translation invariant, with two A uMPS tensors, and the contraction of its 'bra' indices with $\overline{A}$ and $d\overline{A}'$ tensors. PI indicates a pseudo-inverse on the subspace of $D^2 \times D^2$ matrices defined by the projector $1_{D^2 \times D^2} - |r)(l|$. This term stems form a summation over all contributions with the $d\overline{A}'$ tensor to the right of the local Hamiltonian terms (the terms when $d\overline{A}'$ is on the left are zero due to the left tangent gauge condition, which is assumed here).

We note that to solve the TDVP equations one needs to calculate the result of the pseudo-inverse $(1-E)^{PI}$, acting on a vector. This can be done using a conjugate gradient style method [8]. While such terms do not look easily amenable to being solved on a quantum computer, they correspond to minimising a quadratic form, i.e. solving $$Ax = b \qquad (19)$$

for x, corresponds to minimising $$\tfrac{1}{2} x^T A x - b^T x - c. \qquad (20)$$

FIG. 9 reproduces equations (18) to (20).

This generalises straightforwardly to $(1-E)^{PI}(A \otimes d\overline{A}')|r)$, as described in [8], and the corresponding quadratic form can be tackled by a quantum algorithm.

In the present formulation, in order to solve the iTDVP equations, we still need to invert the Gram matrix (17), so one really needs an inverse free classical formulation in order to have any hope of formulating iTDVP on a quantum computer in a natural manner.

Luckily, such a formulation exists, and we describe it in the next subsection.

1.1.3 Inverse-Free TDVP for iMPS

Integrating (3) on a quantum computer is not straightforward, as in general the classical approach necessitates taking inverses of environment matrices, which doesn't generalize nicely to quantum algorithms. We describe a classical method here that avoids inverses [7], which is the starting point for our proposal for a quantum iTDVP algorithm.

The inverse-free update of AL is obtained by solving:

$$\min_{\tilde{A}_L} \|\tilde{A}_L \tilde{C} - \tilde{A}_M\|, \qquad (21)$$

where $$\tilde{C} = C + dt \frac{dC}{dt} \qquad (22)$$

and $$\tilde{A}_M := A_L C + dt \frac{d}{dt}(A_L C). \qquad (23)$$

FIG. 10 reproduces equations (21) to (23).

The solution to (21) is thus the update of AL under time evolution by dt. (3 Here we are only considering the simplest first-order integration method. More elaborate methods can be implemented [7,8]. We also note that imaginary time evolution can be performed, in order to e.g. obtain an approximation to the ground state, in which case the precise integration method matters less).

Figure 11:
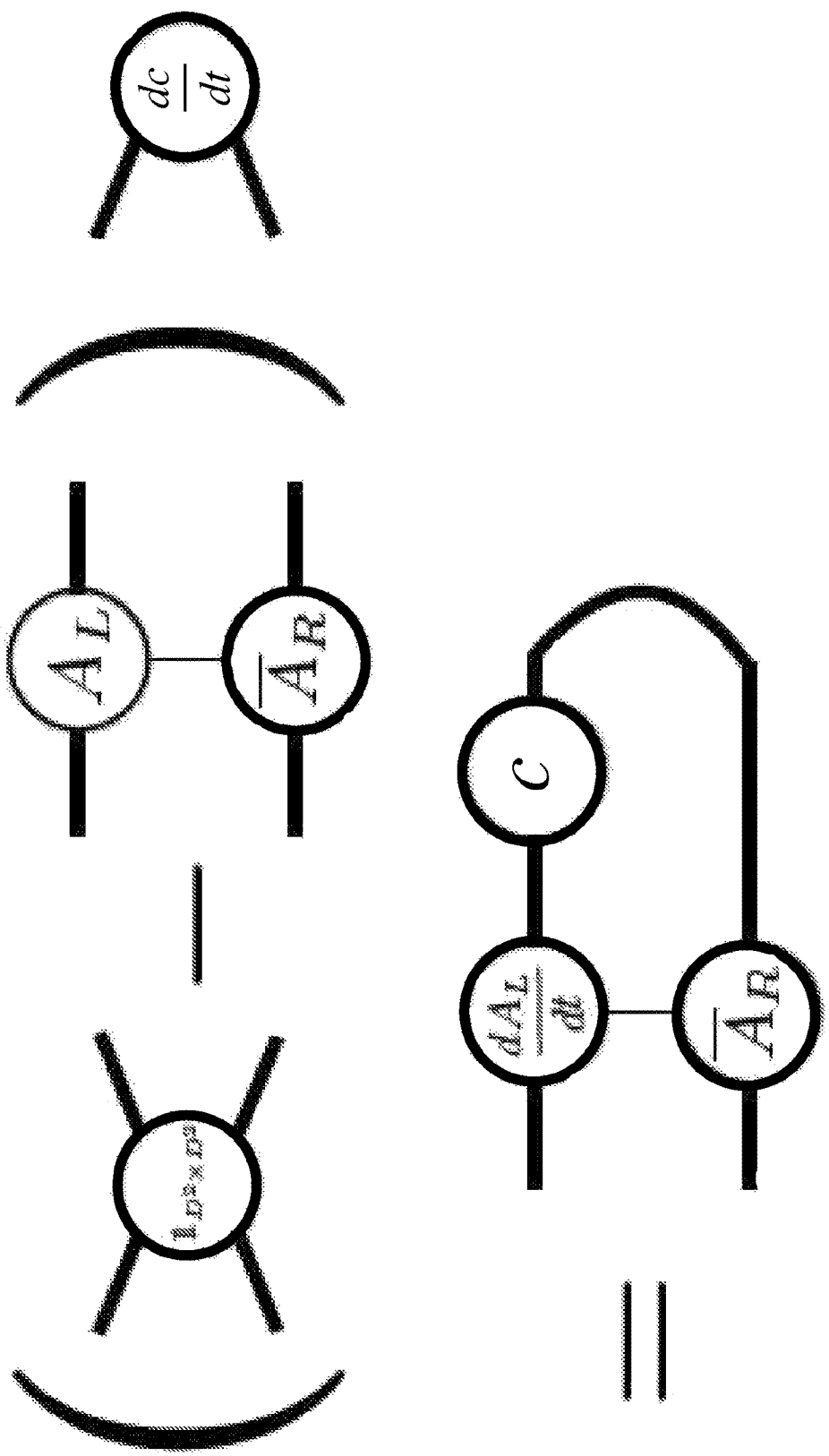
FIG. 11 shows the equation one needs to solve in order to obtain dC/dt.

First, we observe that every quantity in the second term of (21) can be calculated without invoking an inverse of C; $A_L C$ is obviously inverse-free, $$\frac{dA_L}{dt} C \text{ we}$$

know is inverse free from the structure of the TDVP equations, while the equation one needs to solve in order to obtain $$\frac{dC}{dt}$$

can be expressed as shown in FIG. 11 and therefore $$A_L \frac{dC}{dt}$$

can be obtained in an inverse-free manner.

One way of obtaining a solution to the minimisation problem (21) (classically) is by performing a singular value decomposition of the right hand side of:

$$\tilde{A}_L C C^\dagger = \tilde{A}_M C^\dagger, \qquad (24)$$

so $$\tilde{A}_M C^\dagger = U D V^\dagger \qquad (25)$$
$$= U V^\dagger (V D V^\dagger).$$

$VDV^\dagger$ is hermitian, and it turns out $$\tilde{A}_L = UV^\dagger, \qquad (26)$$

is the solution to (21). Alternatively, we can use a QR decomposition, as follows $$\tilde{A}_L \tilde{z} - \tilde{A}_M = \tilde{A}_L \tilde{q} \tilde{r} - \tilde{Q}\tilde{R}. \quad (27)$$

Assuming $\tilde{r} = \tilde{R}$, $$\tilde{A}_L \tilde{q} = \tilde{Q}$$

$$\tilde{A}_L = \tilde{Q}\tilde{q}^\dagger. \quad (28)$$

FIG. 12 reproduces equations (24) to (28).

1.2 Higher Dimensional Tensor Networks

The idea here is to approximate the environment of an infinite 2-dimensional network using lower dimensional networks. So, for iPEPS (see e.g. [2015PhRvB..92c5142P] and references therein), one can represent the up, down, left and right environments of a site using four different iMPS, which in the quantum case can be approximated using bond dimensions exponentially larger than what is classically available. The classical algorithms used to estimate these environments are standard, with all the steps in this process requiring evaluation of circuits of the kind already described in this report.

Estimates of environments, and corner transfer matrices, are described in [9, 10, 11, 12].

2. General Solution on a Quantum Computer

The classical algorithms described above generalise to quantum computers in a relatively straightforward manner.

To start with, one needs a quantum circuit description of an iMPS tensor. Left and right-gauge iMPS tensors are easy to represent using unitary matrices, as shown in FIG. 13.

Figure 13:
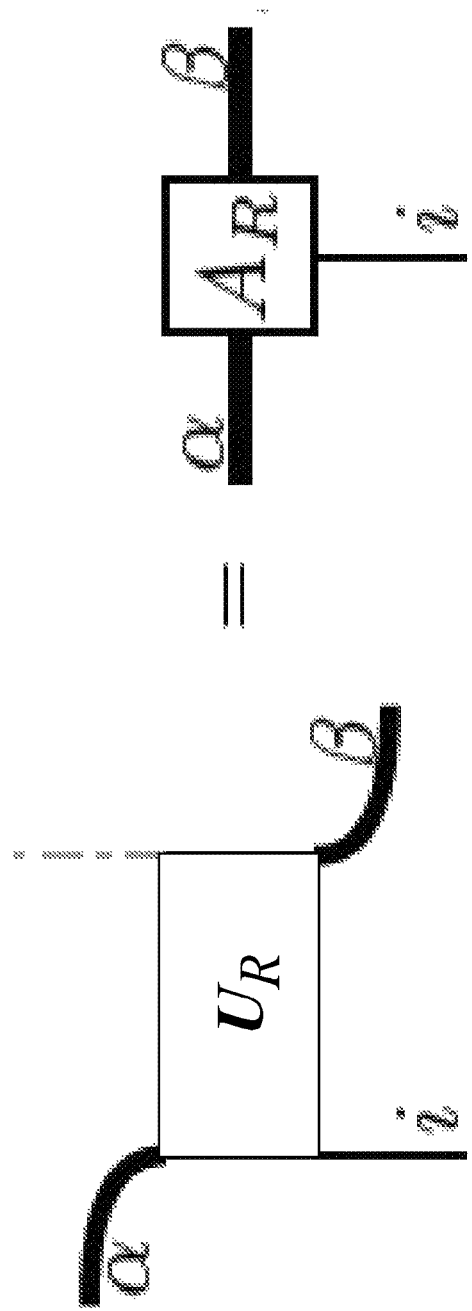
FIG. 13 shows a representation of Left and right-gauge iMPS tensors.

With reference to FIG. 13, $U_R$ stands for a unitary implemented by an arbitrary quantum circuit (not, as in the Examples in Section 4, a 2-qubit gate). The thick lines represent the bond dimensions.

We assume that these thick lines correspond to k qubits (qudits). The effective bond dimension is therefore $2^k(d^k)$, meaning that we can achieve bond dimensions exponentially larger than what is possible classically. The grey line stands for a qubit (qudit) measured in some fixed basis.

The iMPS tensor $A_R$ is not generic, but is constrained by the form of the quantum circuit that specifies it. This is unlike the standard MPS case, where one generally does not constrain the form of the iMPS tensors, and needs to be respected by the quantum algorithm.

Figure 14:
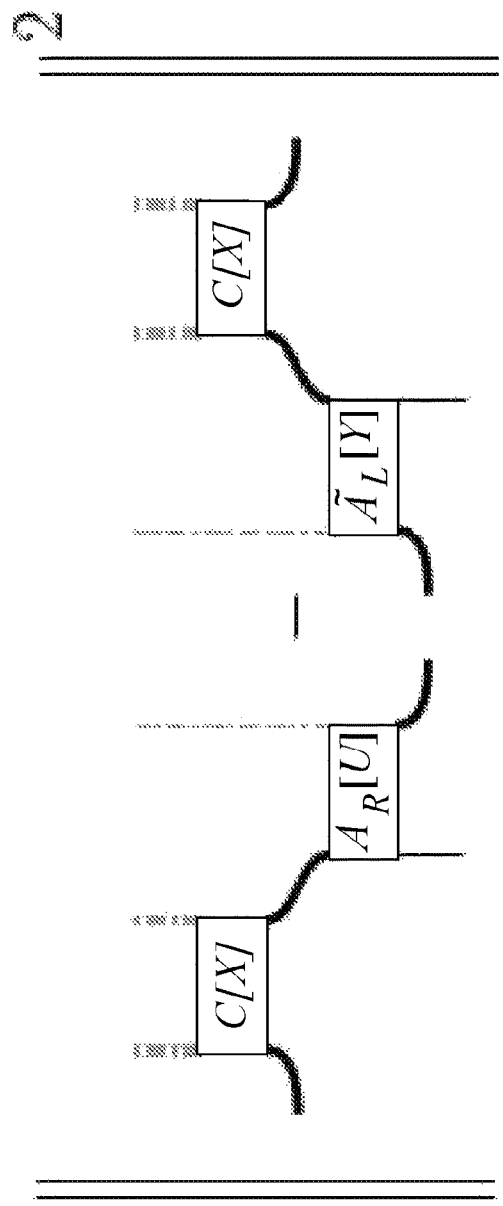
FIG. 14 shows the equation used to obtain a quantum circuit description of the environment tensor.

With reference to FIG. 14, in order to obtain a quantum circuit description of the environment tensor, we need to minimise the pulling-through cost function (13). As in the classical algorithm described in 1.1.1, we fix the form of $A_R$ and design an algorithm that outputs both $A_L$ and C. The difference is that $A_R$ is now determined by some fixed quantum circuit U, and is not a generic iMPS tensor. Similarly, we need to fix a form for an initial guess for C, which we'll call $\tilde{C}$, which is defined in terms of a quantum circuit X, and an initial guess for $A_L$ (denoted as $\tilde{A}_L$), determined by a circuit Y.

In general one can not expect to solve the equation exactly, since the circuits X or Y are generically not going to provide enough variational freedom for $\tilde{A}_L$ and $\tilde{C}$ to exactly capture $A_L$ and C. Given circuit architectures for X and Y, the minimum of the cost function will therefore in general be larger than zero. Nevertheless, one has the freedom to construct increasingly complex circuit architectures, in order to approach the exact solution to arbitrary accuracy, and for special cases it may be possible to identify an Ansatz that can provide an exact solution (as we do for D=2, and attempt to do for D=4 in the Examples section).

Having fixed the circuit architectures for X and Y, the minimisation of Φ with respect to the parameters in X and Y (e.g. angles of one- and two-qubit gates) can proceed using a finite difference method following [13, 14], or a more sophisticated method based on computing analytic gradients, such as the one described in [15].

Figure 15:
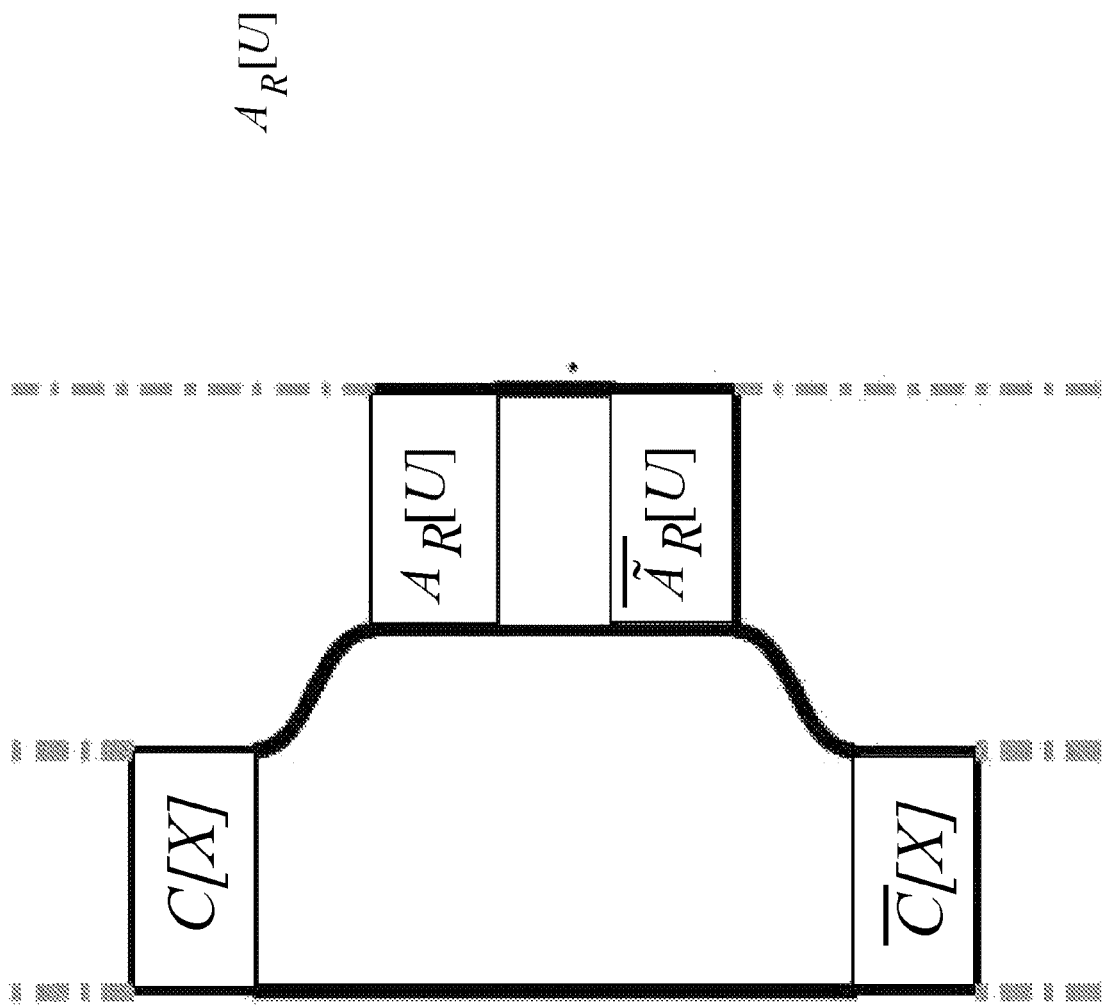
FIG. 15 shows one of the terms from FIG. 14.

It is clear that every element in FIG. 14 can be estimated by running and sampling specific circuits in the expansion. With reference to FIG. 15, let us consider one of the terms. The circuit is run from top to bottom, or bottom to top. We start using the fixed basis that was used to define C and AR—let's assume this is $(|0\rangle)_{in}^{n}$, where $n_{in}$ is the number of auxiliary inputs. Then we measure the output in the same basis, as in the in method for the measuring the overlap of two states (fidelity) in FIG. 2C in [16].

2.1 Minimisation of an Operator Expectation Value

Outline of the algorithm:
1. Define iMPS tensor A.
2. Calculate environment as described in Section 2.
3. Calculate expectation value of H (or some other operator), given the environment this calculation is essentially that of [13]. A is updated as described in Appendix 5: Operator Expectation Value, or in [13]—so using a finite difference method, or a more sophisticated approach such as the one described in [15].
4. 'goto 2)', while recycling as much from the previous steps as possible, such as the precise angles and unitaries of the environment circuit.

2.2 iTDVP on a Quantum Computer

It is straightforward to perform all the inverse free steps TDVP described above steps by evaluating and sampling from results of quantum circuits, using the general procedure described in Section 2 for the environment.

In order to update the iTDVP equation, minimisation in (21) needs to be performed.

Every term in (21) can be obtained by combining appropriate quantum circuits describing the environments, iMPS tensors and operators. Each circuit is then sampled using the procedure described in [15].

For terms involving a pseudo-inverse, an appropriate quadratic form, as described in 1.1.2, needs to be evaluated. This means that further quantum circuits to represent the action of the pseudoinverse term on a vector need to be introduced (the architecture of these circuits needs to be chosen in a maximally optimal manner, as for the environments).

Having evaluated all the terms in (21), minimisation over $\tilde{A}_L$ is performed, as for the environment above, using a finite difference method, or a more sophisticated approach such as the one described in [15].

3. Key Concepts

Method for optimising translation invariant tensor networks for infinitely large systems on quantum computers.

Specific algorithms for solving one-dimensional quantum mechanical problems in the thermodynamic limit, like finding the ground state of a specific Hamiltonian or minimising the expectation value of another local operator of interest.

Method for running real or imaginary time evolution algorithms on quantum computers.

Generalisation to higher dimensions based on approximations of the environment using iMPS (this is straightforward given the iMPS proposals here—include my code), or corner transfer matrices.

Generalisation of the above to density matrices.

Machine learning applications generalising the techniques in Appendix A to infinite systems. As in the description in Appendix A, the 'operator' or the network itself can be optimised in any combination—unlike for quantum mechanical problems where one is concerned with optimising the tensor network describing the state alone. Note that the classical version of this algorithm is itself a key concept. We need to also remember that this does not necessarily need to be done using the operator ML formalism (Appendix A) but applies to a Stoudenmire style MPS algorithm [17].

Generative methods along the lines of [18].

Any of the key concepts listed above may also apply to finite systems.

4. Examples of Circuit iMPS Ansateze

We now describe use case examples of solving the bound order 2 case and the bound order 4 case. The D=2 case is first described as it requires less computation thanks to an interesting property providing that an exact solution is identifiable.

An exact solution is however not necessary as algorithms can be constructed to find $A_L$ and $A_R$ even when the iMPS is not a chiral iMPS and the puling-through equation cannot be solved exactly using a very simple Ansatz for $A_L$. In the general case, a solution may be solved directly on a computer.

For chiral iMPS that represents a chiral state, we can use the same U to represent $A_L$ and $A_R$ (with appropriately swapped indices), so that all we need to do with the pulling through equation is find C. Chiral iMPS states are characterised by an existence of a gauge for which the matrices are complex-symmetric [8]. In this gauge the left and right environment matrices are numerically equivalent, i.e. we are in the symmetric gauge [2014arXiv1408.5056H] (so, non-chiral states in the symmetric gauge are not simplex-symmetric).

An exact solution for $A_L$ (given an $A_R$ and C) can be identified for D=2.

Even though an exact solution may not be found for higher bounder case, such as D=4, a general solution is still achievable computationally. Complex circuits can be picked to represent $A_L$ and C (in the case of the pulling through equation, as described in Section 2), or e.g. for the objects of interest for iTDVP.

4.1 The D=2 Case

4.1.1 Tensor Network Drawings

Let's start by rewriting a translation invariant matrix product state for a system of qubits (physical dimension d=2) in terms of a staircase circuit using unitaries with fixed legs.

Figure 16:
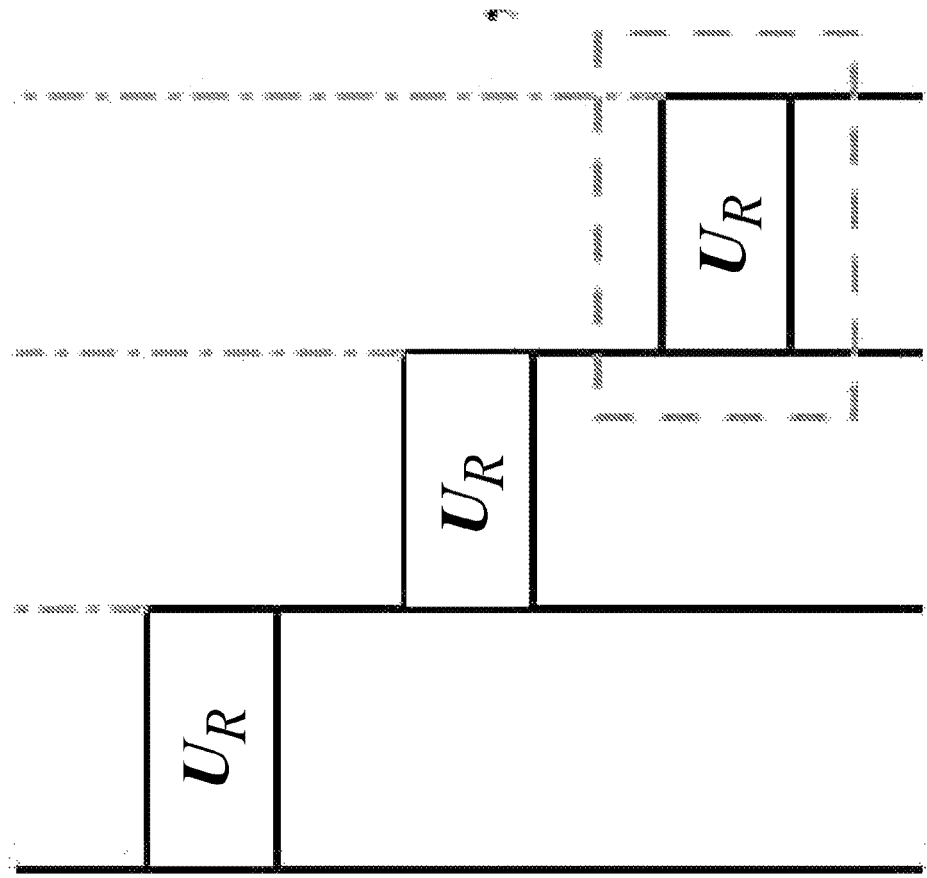
FIG. 16 shows a manifestly right-canonical circuit.
Figure 17:
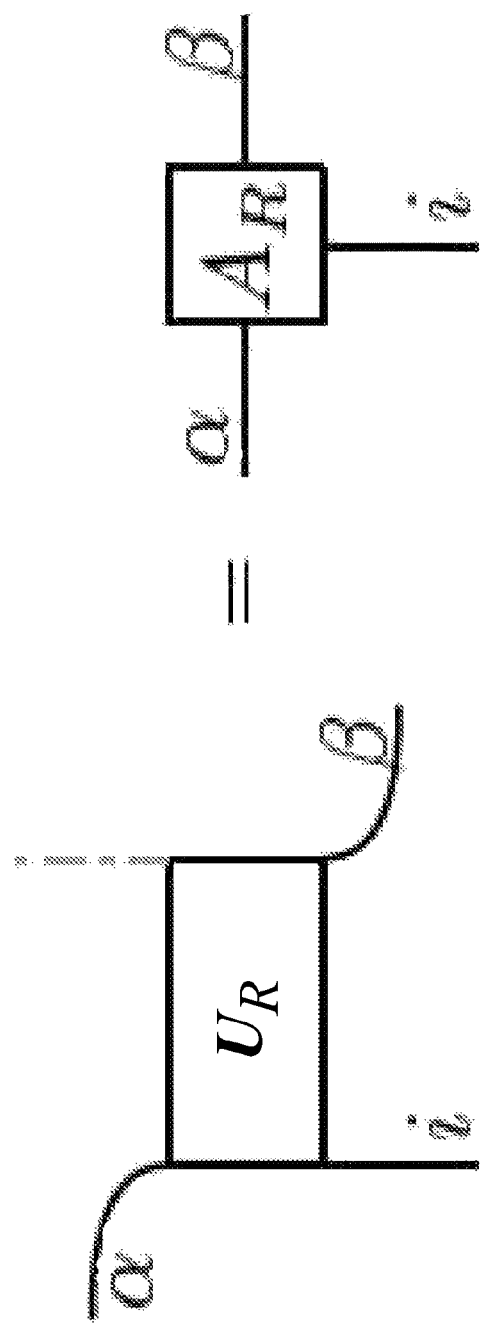
FIG. 17 shows the right-gauge MPS tensor.
Figure 18:
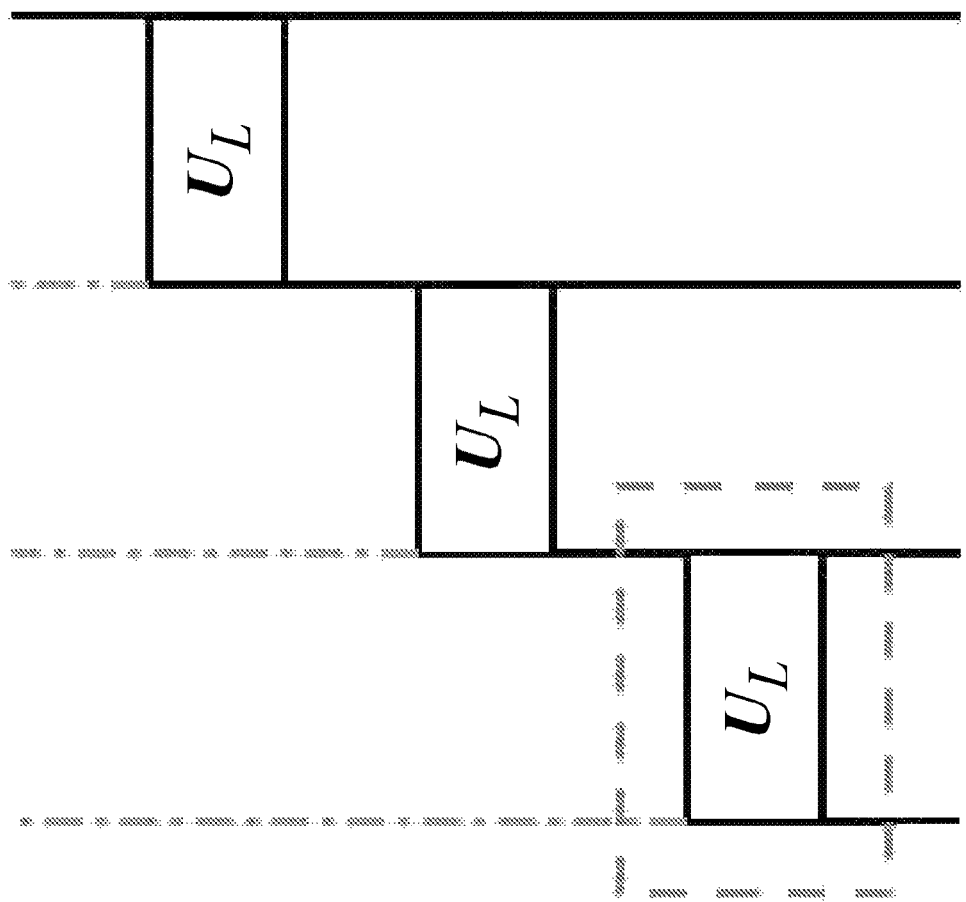
FIG. 18 shows the manifestly left-canonical case.
Figure 19:
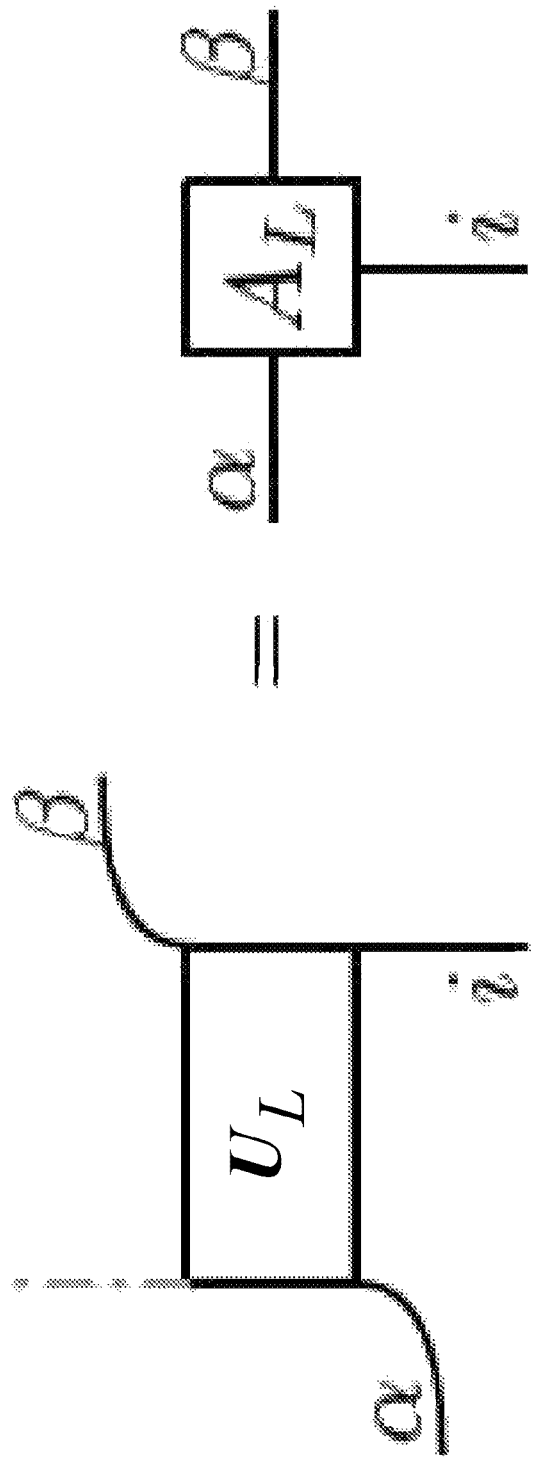
FIG. 19 shows the left-gauge MPS tensor.

With reference to FIG. 16, in terms of isometries, a manifestly right-canonical circuit is shown, where we can identify the right-gauge MPS tensor as seen in FIG. 17. Similarly, the manifestly left-canonical case is shown in FIG. 18 where we can identify the left-gauge MPS tensor as shown in FIG. 19.

Figure 20:
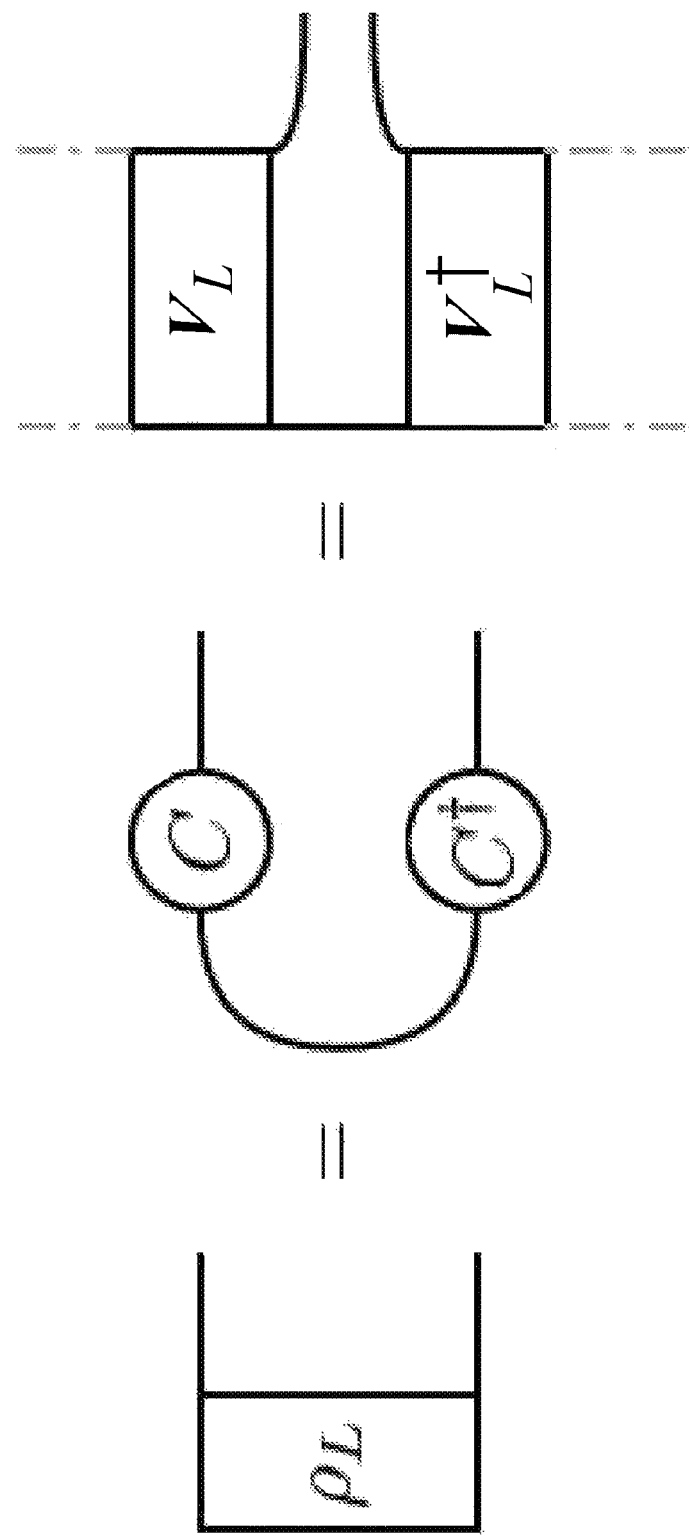
FIG. 20 shows an Ansatz for left environment tensor.
Figure 21:
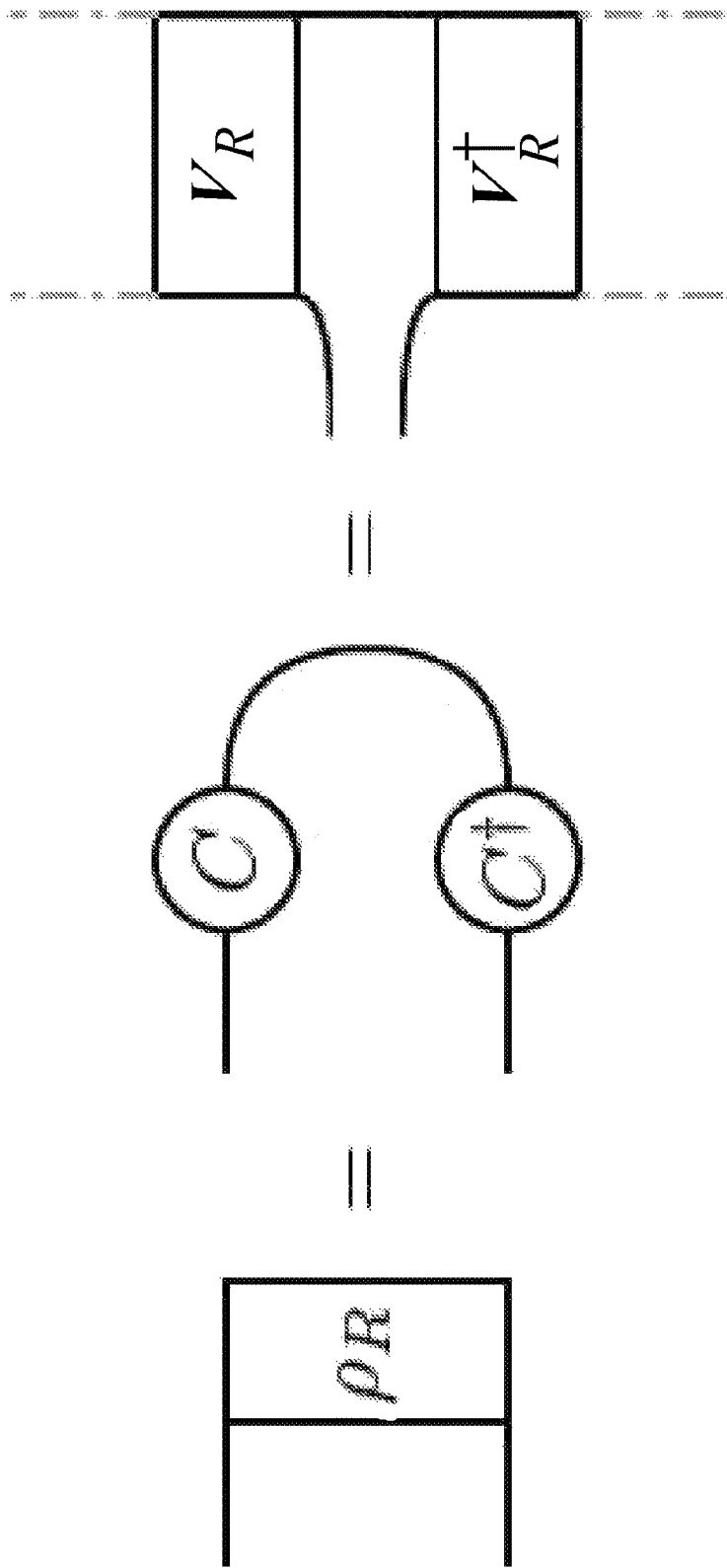
FIG. 21 shows an Ansatz for right environment tensor
Figure 22:
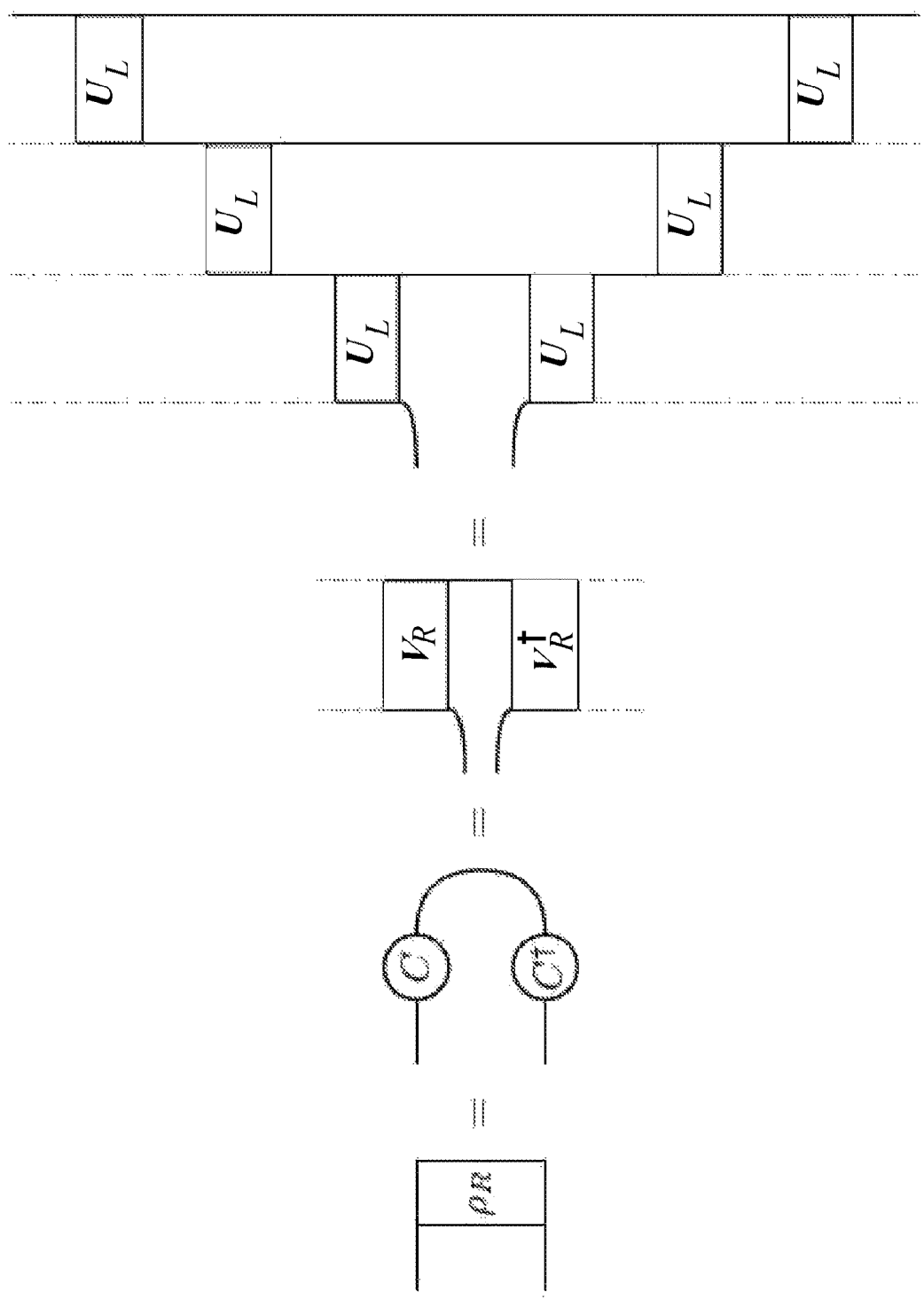
FIG. 22 shows the decomposition of the right-fixed point for a MPS in left canonical form.
Figure 23:
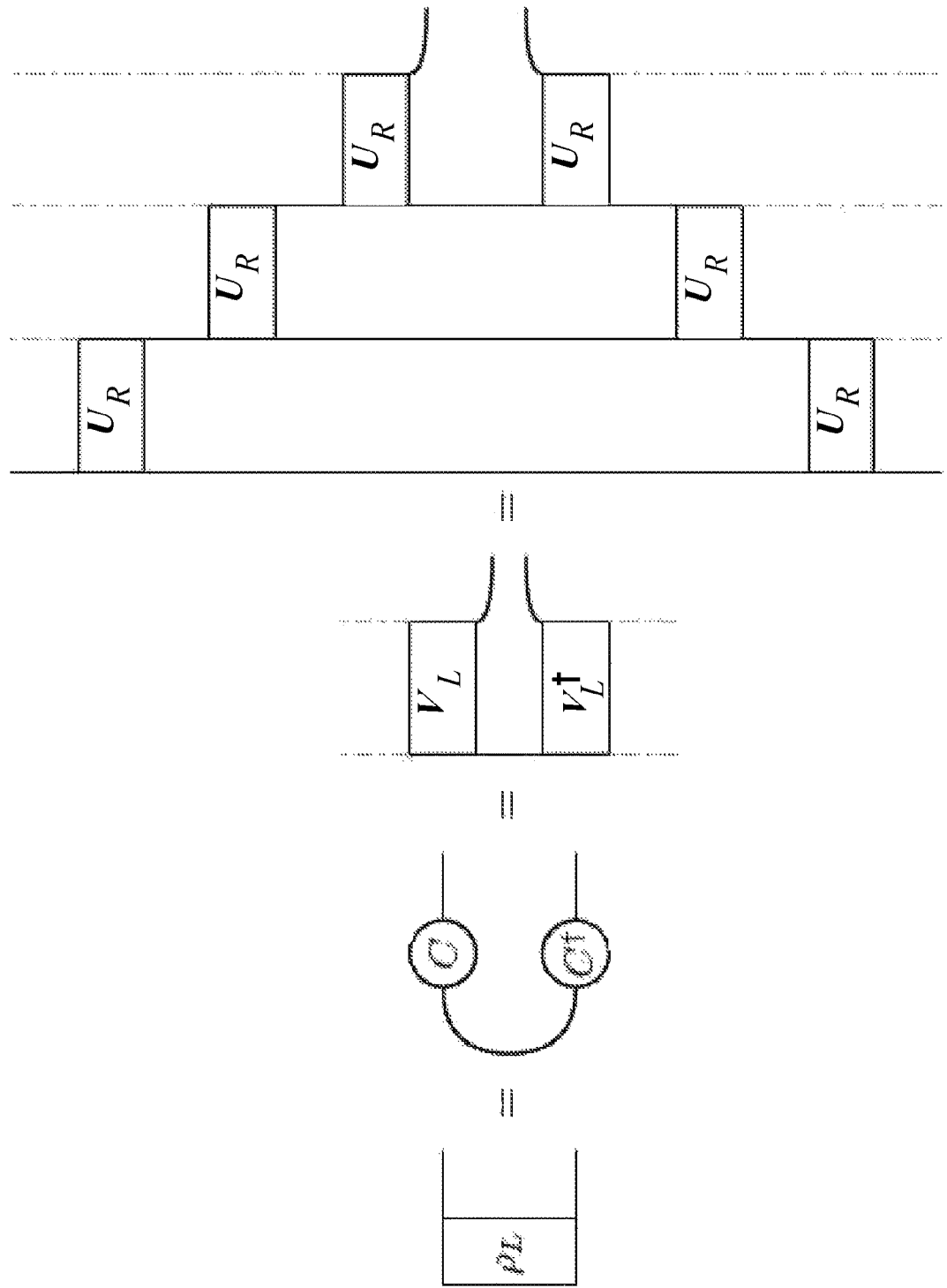
FIG. 23 shows the decomposition of the left-fixed point for a MPS in left canonical form.

With reference to FIGS. 20 and 21, an Ansatz for left and right environment tensors are shown in terms of unitaries $V_L$ and $V_R$ with two legs fixed. Explicitly, the right-fixed point for a MPS in left canonical form can be decomposed as shown in FIG. 22 while the left-fixed point is shown in FIG. 23.

4.1.2 Remarks

Let me now discuss some numerical findings which I did not anticipate from the notes. At the risk of sounding obvious, for random unitaries $U_L$ and $U_R$, the associated MPS tensors $A_R$ and $A_L$ do not represent the left- and right-canonical form of the same state;

they correspond to different states altogether. I am not sure if it's possible to pick $U_L$ and $U_R$ such that $A_L$ and $A_R$ represent different gauges of the same state by merely fixing legs but my guess would be that that is impossible. There's no way to "translate" between the two descriptions since they represent different states not related by gauge transformations. Even for a single random unitary $U \equiv U_L = U_R$, the associated MPS tensors $A_L$ and $A_R$ also represent different states. Swapping auxiliary indices does not change anything about this.

4.1.3 Pulling-Through Equation

Figure 24:
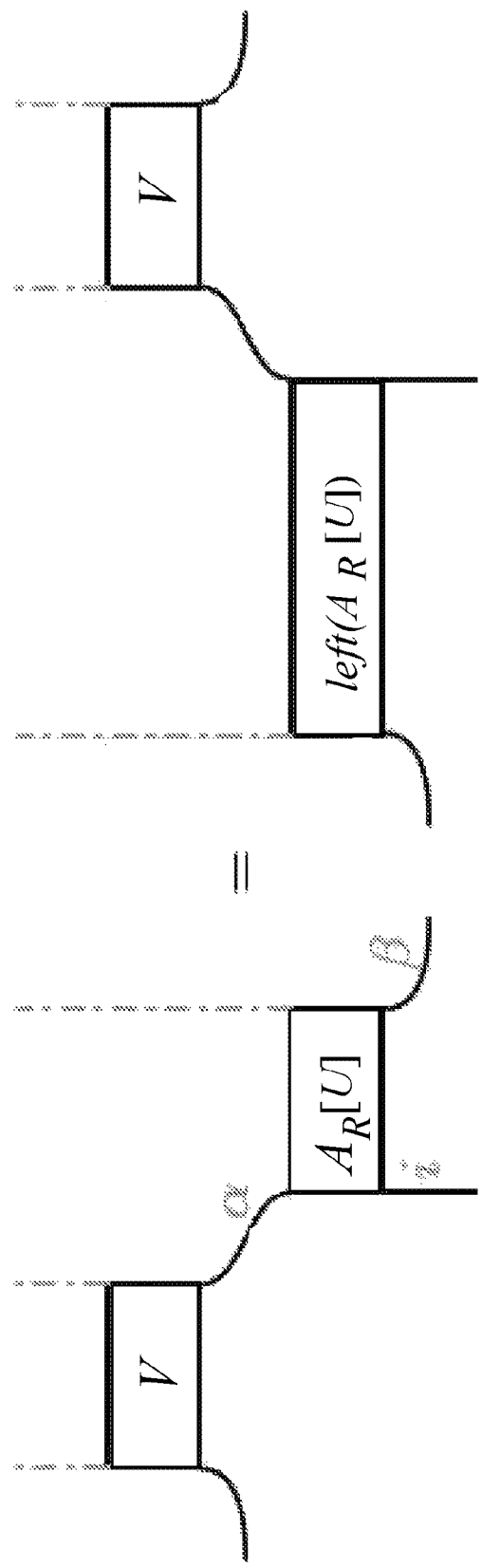
FIG. 24 shows iMPS tensor ($A_R$).

Given the above, we should be very careful when writing down pulling-through equations. With reference to FIG. 24, let's pick a choice of iMPS tensor ($A_R$) try to arrive at the result on the relationship between the environment unitary V and iMPS unitary U from an ever so slightly different angle, starting off with the pulling-through equation (10) for C=V where we interpret U as corresponding to a right-canonical $A_R$ (and only to a rightcanonical $A_R$) on the left-hand side. On the right-hand side we expect to find the left canonical form of the right-canonical $A_R$ built from U, expressed in terms of U. This is the only pulling-through equation which makes sense, together with its equivalent for $A_L[U]$ which represents a different state.

Figure 25:
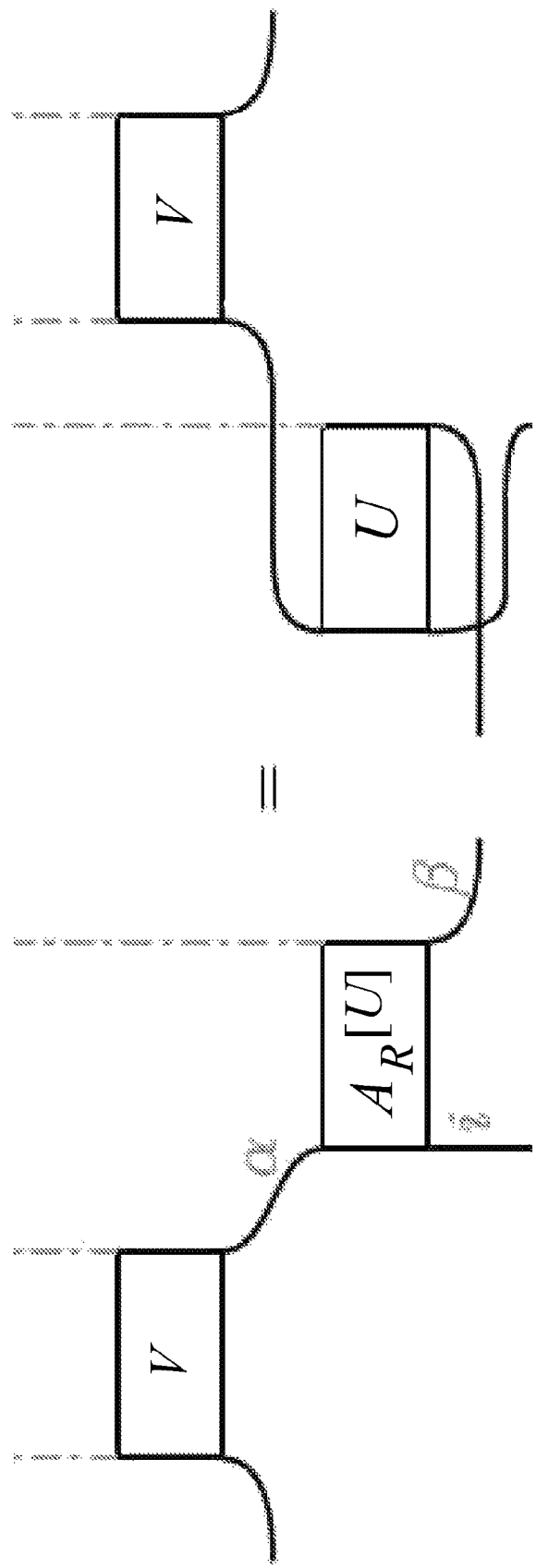
FIG. 25 shows an equation involving U which quickly converges and yields the correct environment.

Numerically, no unitary V can be found when substituting U for left($A_R[U]$) in the above equation. I found that this is the only equation involving U which quickly converges and yields the correct environment when compared to conventional iMPS methods is shown in FIG. 25.

Figure 26:
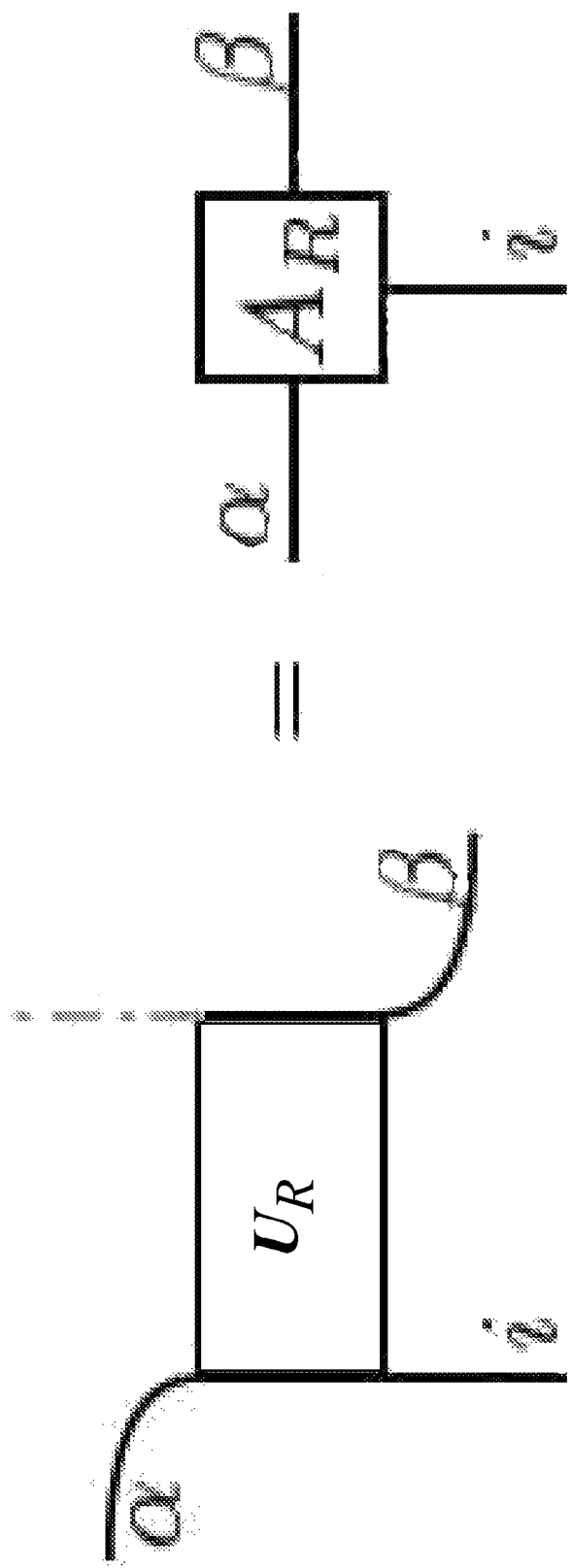
FIG. 26 shows an equation including a Utensor.

With reference to FIG. 26, this works is because the Utensor with swapped legs like that is just $A_R[U]$, but with swapped auxiliary indices, trivially making the right-canonical form $A_R[U]$ left canonical. Note however that this left-canonical form of $A_R[U]$ has nothing to do with $A_L[U]$, since, again, $A_L[U]$ is a different state.

4.1.4 Numerics for D=2

Figure 27:
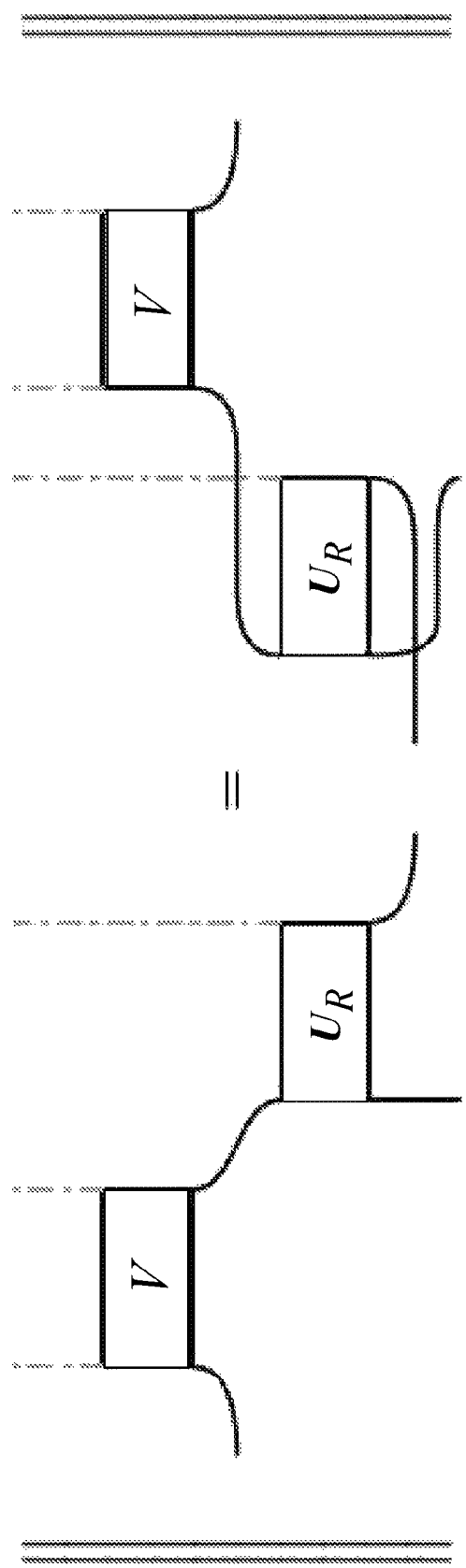
FIG. 27 shows the equation leading to a suitable unitary V.

With reference to FIG. 27, given a random unitary $U_R$ for the $A_R$ equation, minimizing the Frobenius norm on the complex Stiefel manifold using manopt yielded a suitable unitary V. Calculating $\rho_L = C^\dagger C$ as the fixed point of $A_R$ (see FIG. 26) using conventional iMPS methods yields the same (2×2)-matrix as $V^\dagger V$ with V obtained from the optimization.

4.2 The D=4 Case

Since physical and virtual dimensions are equal for D=2, and the swapped right canonical iMPS tensor is just equal to its original one up to a gauge, the results of the previous section work out but are rather trivial. Getting D=4 to work will require to work in this way will require more work. For higher dimensional MPS one can always resort to the general algorithm outlined at the beginning of 2.2.

4.2.1 Tensor Network Drawings

Figure 28:
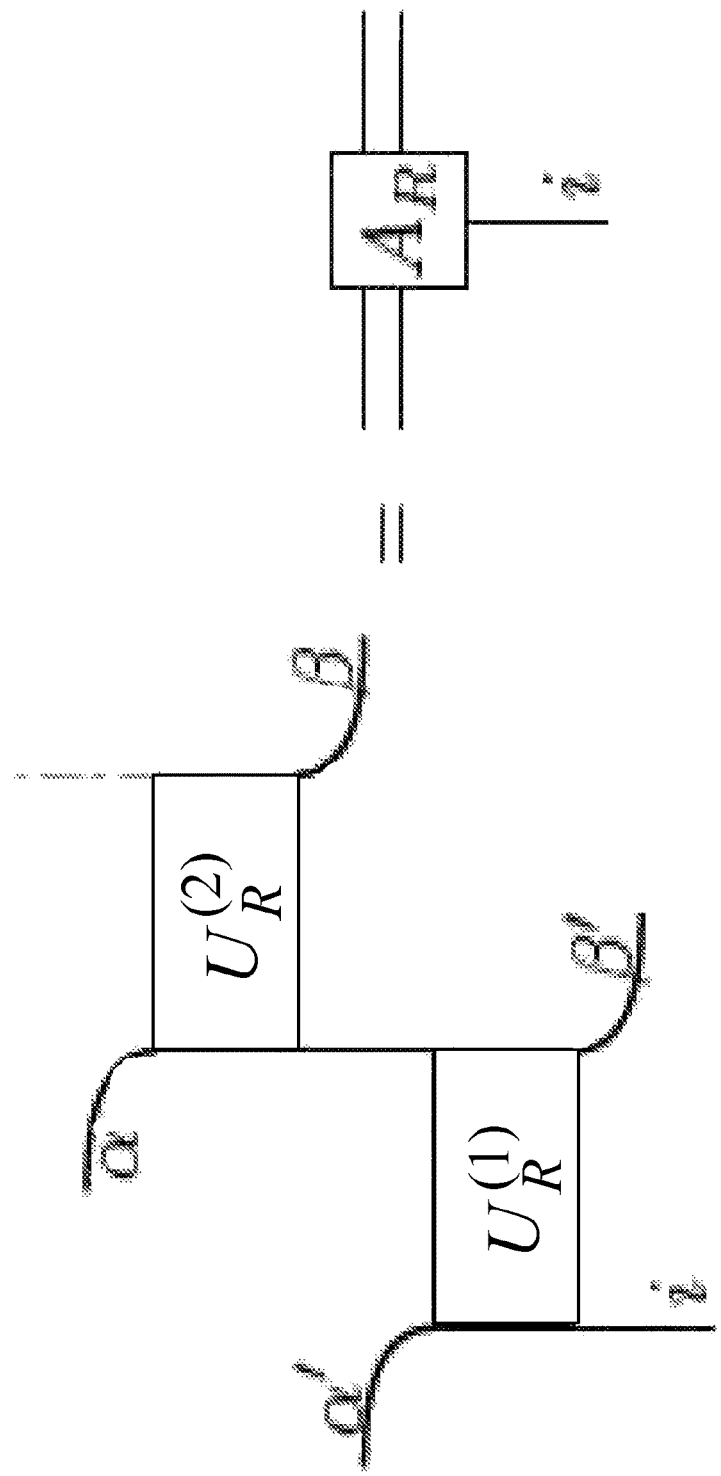
FIG. 28 shows an Ansatz for the case D=2.

With reference to FIG. 28, it is straightforward to check numerically that one no longer has the invariance-under-swapping property like in the D=2 case. You trivially get a tensor which is in the opposite isometric form, but, for random unitaries, this swapped iMPS represents a different state. One needs additional restrictions on $A_R(U_R)$ such that the iMPS representation is in fact swap-invariant. Random iMPS tensors (like those created from random unitaries with fixed legs) just aren't generically invariant under the swapping of virtual indices. If they would be, then their transfer matrix would be Hermitian with a real spectrum. But that's not the generic case: transfer matrices of random iMPS tensors have a blob of complex eigenvalues inside the unit circle on the complex plane, and also tend to be very gapped (see [19]).

4.2.2 Numerics for D=4

Figure 29:
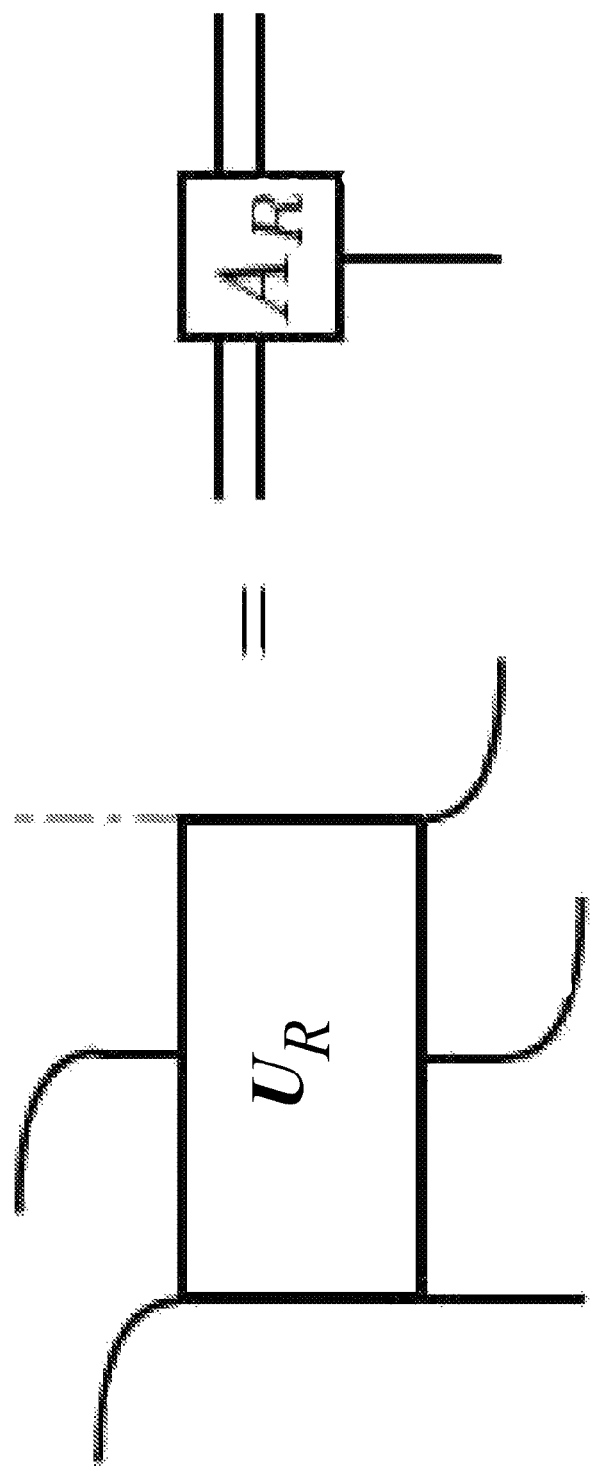
FIG. 29 shows an Ansatz for D=4.

With reference to FIG. 29, to make all of this as explicit as possible, let us focus on the full Ansatz to avoid any representation problems due to the restricted generality of the particular Ansatz in FIG. 28.

Figure 30:
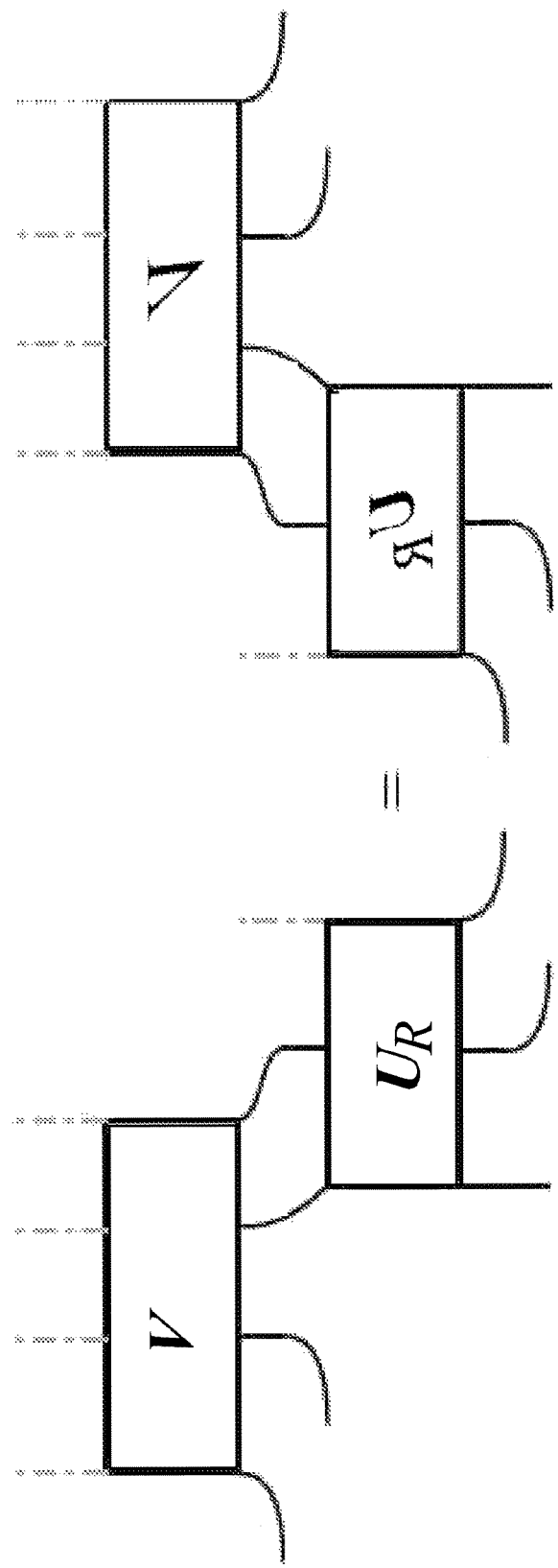
FIG. 30 shows an equation shown where the right-hand side is the horizontal flip of the left-hand side.

The equation shown in FIG. 30, where the right-hand side is the horizontal flip of the left-hand side, is actually not a valid pulling-through equation since $C^T$ features on the right-hand side instead of C. If we denote the swap on the MPS with a transpose operation, this equation essentially amounts to $CA_R=A_R^T C^T$, which, as verified numerically, quickly converges to a matrix C tuned such that $CA_R(C^T)^{-1}=A_R^T$, i.e. it takes the state to its swapped state. This is however not a gauge transformation since $(C^T)^{-1}C\neq 1$.

The cost function for the case $CA_R=A_R^T C$ gets stuck at a value of O(0:1) and does not converge to anything sensible since it corresponds to a pulling-through equation which tries to connect different states.

The only cost function which quickly converges to the correct fixed point is $CA_R=\text{left}(A_R)C$, where $\text{left}(A_R)$ corresponds to the left-canonical form of $A_R$.

To make the pulling-through equation work without having to calculate the left-canonical tensor $\text{left}(A_R)$ of $A_R$, one needs additional restrictions on $A_R(U_R)$ such that is in fact swap-invariant. And this brings me back to a point made in the previous section for D=2: this is not in general possible for D>2.

However, a sufficiently expressive circuit Ansatz for left $(A_R[U])$ enables one to get arbitrarily close to a solution as described at 2.2.

5. Use Cases

5.1 Predicting Quantities that are Closely Related to Crystal Structures

The starting point for our machine learning models are graph-convolutional networks. These represent molecules using an abstract graph, which is defined with 'features' which are values (such as partial charges, species decorated onto the nodes, and similar on the edges covalent bonds, distances, etc). The most simple representation is to directly use the molecular graph, but there are various methods and motivations to use a more abstract representation. It is also quite natural to add environmental information, such as periodic boundary conditions, long range interactions, to this representation. Periodic boundary conditions and quantum systems in the thermodynamic limit can be tackled quite naturally in the formalism of tensor networks.

With this representation, and with our Machine Learning techniques, conformational, molecular dynamic and quantum-chemical calculated features can be used to supplement the dataset.

When we predict solubility directly from molecular structure we achieve state of the art results on some benchmark datasets. On the quite particular and very simple ESOL data set, we achieve R2=0.98 beating the state of the art model, which has R2-0.94. We have also run our baseline models on the PUBCHEM dataset on solubility, and achieved R2>0.4. In principle we could also attempt the prediction of melting point, as the underlying physics are quite similar and heuristically related by the general solubility equation.

Scientific Pipeline

A two-step approach is developed combining de novo and machine learning methods, and incorporating a physically motivated intermediate stage of representation that can benefit from learning on simulated such as crystal structure prediction, and molecular dynamics results. Some of this learning is on entirely artificial data (i.e simulation results), and we also use artificial data to supplement the (fewer, and less rich) experimental data.

Based on a choice of polymorphs for a given molecule, we then run a set of calculations on these crystal structures to obtain features for machine learning. This set includes relevant per atom or per bond features in a graph description of the molecule. More generally, we use a representation that lives in the space of molecular orbitals. Information about the periodic structure including space group and unit cell parameters, and weak intermolecular features between unit cells are used to describe edges (connections) on the graph.

The algorithm described above could significantly improve the prediction of polymorphs for a given molecule, or even enable them to be produced for all cases when classical methods are insufficiently accurate. Predicting possible crystal structures of a solid, and the associated probabilities. Having a way of calculating accurate energies is important for this, as energy differences between different crystal configurations are sometimes very small. If classical methods are expensive or infeasible, quantum computation becomes necessary A lot of the practical challenges are in coming up with a set of suitable features, writing codes to automatically calculate them in a sufficiently fast and automated manner, and constructing the machine learning models to make use of these features.

The final prediction step for the solubility is based on those features, using machine learning and data synthesis as an efficient alternative to otherwise costly de novo computations.

Initially we start with small organic molecules, where structural and solubility data is available. From here, once validated against reality, flexible drug-like molecules relevant for pharma (even if not actual pharmaceuticals) are simulated. We obtain a dataset from the literature as a starting point, and then perform synthesis and lab work iterated over a number of synthesis rounds. In that process we use active learning in order to ensure that the models are maximally generalisable with minimal amount of data. The goal is to capture a pharmaceutically interesting area of chemical space.

The methods described here can also aid in predicting possible crystal structures, since energy differences are often tiny, and accurate predictions are therefore necessary.

5.2 Further Use Cases

Further use cases include, but are not limited to:

Simulating effectively infinite periodic systems, materials in solid state, crystal structures, quantum systems in a gas phase (assuming our approach is applied to a discretisation of the continuum) and other periodic systems.

Calculating accurate energy densities or other properties of effectively infinite periodic systems.

Predicting possible crystal structures of a solid, and the associated probabilities. Having a way of calculating accurate energies is important for this, as energy differences between different crystal configurations are sometimes very small. If classical methods are expensive or infeasible, quantum computation becomes necessary.

Simulating and calculating energies of excited states.

Calculating other properties of infinite periodic systems, such as light absorption properties.

Beyond quantum simulation: ML for effectively infinite systems, such as NLP, audio, stock market prediction.

REFERENCES

[1] See Appendices 1 & 5.
[2] J. Haegeman et al. "Time-Dependent Variational Principle for Quantum Lattices". In: Physical Review Letters 107 (2011), p. 070601. DOI: 10.1103/PhysRevLett.107.070601.
[3] J. Haegeman, T. J. Osborne, and F. Verstraete. "Post-matrix product state methods: To tangent space and beyond". In: Phys. Rev. B 88.7, 075133 (August 2013), p. 075133. DOI: 10.1103/PhysRevB.88.075133. arXiv: 1305.1894 [quant-ph].
[4] J. Haegeman et al. "Geometry of Matrix Product States: metric, parallel transport and curvature". In: ArXiv e-prints (October 2012). arXiv: 1210.7710 [quant-ph].
[5] J. Haegeman et al. "Shadows of anyons and the entanglement structure of topological phases". In: Nature Communications 6, 8284 (October 2015), p. 8284. DOI: 10.1038/ncomms9284. arXiv: 1410.5443 [cond-mat.str-el].
[6] N. Bultinck et al. "Anyons and matrix product operator algebras". In: ArXiv eprints (November 2015). arXiv: 1511.08090 [cond-mat.str-el].
[7] J. Haegeman and F. Verstraete. "Diagonalizing Transfer Matrices and Matrix Product Operators: A Medley of Exact and Computational Methods". In: Annual Review of Condensed Matter Physics 8 (March 2017), pp. 355-406. DOI: 10.1146/annurev-conmatphys-031016-025507. arXiv: 1611.08519 [cond-mat.str-el].
[8] Jutho Haegeman. "Variational renormalization group methods for extended quantum systems". eng. PhD thesis. Ghent University, 2011, pp. XX, 354.
[9] L. Vanderstraeten et al. "Excitations and the tangent space of projected entangled pair states". In: Phys. Rev. B 92.20, 201111 (November 2015), p. 201111. DOI: 10.1103/PhysRevB.92.201111. arXiv: 1507.02151 [cond-mat.str-el].
[10] L. Vanderstraeten et al. "Gradient methods for variational optimization of projected entangled-pair states". In: Phys. Rev. B 94.15, 155123 (October 2016), p. 155123. DOI: 10.1103/PhysRevB.94.155123. arXiv: 1606.09170 [cond-mat.str-el].
[11] M. T. Fishman et al. "Faster Methods for Contracting Infinite 2D Tensor Networks". In: ArXiv e-prints (November 2017). arXiv: 1711.05881 [cond-mat.str-el].
[12] L. Vanderstraeten, J. Haegeman, and F. Verstraete. "Simulating excitation spectra with projected entangled-pair states". In: ArXiv e-prints (September 2018). arXiv: 1809.06747 [cond-mat.str-el].
[13] A. Kandala et al. "Hardware-efficient variational quantum eigensolver for small molecules and quantum magnets". In: Nature 549 (September 2017), pp. 242-246. DOI: 10.1038/nature23879. arXiv: 1704.05018 [quant-ph].
[14] E. Grant et al. "Hierarchical quantum classifiers". In: ArXiv e-prints (April 2018). arXiv: 1804.03680 [quant-ph].
[15] M. Benedetti et al. "Adversarial quantum circuit learning for pure state approximation". In: ArXiv e-prints (June 2018). arXiv: 1806.00463 [quant-ph].
[16] V. Havlicek et al. "Supervised learning with quantum enhanced feature spaces". In: ArXiv e-prints (April 2018). arXiv: 1804.11326 [quant-ph].
[17] E. Miles Stoudenmire and D. J. Schwab. "Supervised Learning with Quantum-Inspired Tensor Networks". In: ArXiv e-prints (May 2016). arXiv: 1605.05775 [stat.ML].
[18] Z.-Y. Han et al. "Unsupervised Generative Modeling Using Matrix Product States". In: Physical Review X 8.3, 031012 (July 2018), p. 031012. DOI: 10.1103/PhysRevX.8.031012. arXiv: 1709.01662 [cond-mat.stat-mech].
[19] V. Zauner et al. "Transfer matrices and excitations with matrix product states". In: New Journal of Physics 17.5, 053002 (May 2015), p. 053002. DOI: 10.1088/1367-2630/17/5/053002. arXiv: 1408.5140 [quant-ph].

APPENDIX 1

Tensor Network Based Machine Learning System

Definitions

The term 'tensor' preferably connotes a multidimensional or multi-rank array (a matrix and vector being examples of rank-2 or rank-1 tensors), where the components of the array are preferably functions of the coordinates of a space.

The term 'tensorial space' is equivalent to a tensor network.

The term 'tensor network' is defined as follows. A tensor network can be thought of as a way of representing a high rank tensor in terms of a 'bag' of small rank tensors, together with a recipe (i.e. a set of contractions along some of the dimensions of the smaller tensors) which is capable of reproducing the original high-rank tensor. In the context of quantum mechanics, given a matrix/tensor description of an observable, a tensor contraction recipe can reproduce the expectation value of that observable with respect to the wave function described by the high rank tensor (depending on the tensor network, an efficient method may or may not be available). See arxiv.org/abs/1306.2164 [A Practical Introduction to Tensor Networks: Matrix Product States and Projected Entangled Pair States Annals of Physics 349

(2014) 117-158] for details. A wave function or a quantum state of a system can be approximated or represented using a tensor network.

The term 'tensor network' is also used broadly and expansively in this specification. Specifically, the definition of a 'tensor network' in terms of a general bag-of-tensors, as given above, is very general. Commonly the term 'tensor network' used in a more restricted sense, for specific tensor networks ansätze used to describe quantum systems at low energies, and where the tensors from which the large-rank tensor is reconstructed (i.e. the building block tensors) are all small rank. Let us call these 'area-law tensor networks' (as they by construction obey the area law, up to perhaps topological corrections, see e.g. Entanglement rates and area laws; Phys. Rev. Lett. 111, 170501 (2013) arxiv.org/abs/1304.5931 and references therein). For example, even though they fit our bag-of-tensors definition above, many physicists would not consider correlator product states as tensor networks, the reason being that these in general contain high rank building-block tensors. Now, these high rank building-block tensors are very special for correlator product states, in that they are highly sparse—and this often enables efficient evaluations of observables of interest (either via a direct contraction or using Monte Carlo methods—see e.g. Time Evolution and Deterministic Optimisation of Correlator Product States Phys. Rev. B 94, 165135 (2016) arxiv.org/abs/1604.07210 and references therein). So the Ansatz is not exponentially expensive, which is the reason why it is commonly used to describe systems with non-local correlations. Nevertheless it's not generally considered a tensor network, as it is not an 'area-law tensor network'. In the context of the present patent, we will use the term tensor network in its fully general definition—not restricted to those networks that are efficiently contractible, and also allowing for tensors defined as superpositions of distinct tensor networks (e.g. a superpositions of different tensors from the same class, e.g. two matrix product states, or a superposition of a rank-n tensor decomposed as and MPS, and as a MERA). In addition, our definition allows for tensor networks describing states with volume law entanglement, which can, for example, provide descriptions of highly excited states present in transition states of small molecules in a reaction or a binding process. We will also allow for tensor networks describing density matrices—both those that obey the area law, and those that do not.

The term 'wave function space' preferably connotes a description of the quantum state of a system and optionally also connotes density matrices, for example those used to describe quantum systems in mixed or thermal states.

The term 'dimensionality' preferably connotes the number of dimensions and/or variables associated with a particular situation.

The term 'novel dataset of (candidate) chemical compounds' preferably connotes a dataset comprising at least one (candidate) chemical compound that is not in an original dataset of chemical compounds.

The term 'mode' or 'rank' preferably connotes the number of constituents of the system.

The dimensionality of a tensor is, in particular, exponentially large in the number of modes.

The term 'entanglement' connotes entanglement entropy as commonly used for bosonic systems (arxiv.org/abs/1306.2164). Our definition includes the application of the concept of entanglement entropy to fermionic systems (e.g. electrons), which requires additional qualifications described e.g. here https://arxiv.org/abs/quant-ph/0203060.

The terms 'chemical compound' and 'molecule' are used interchangeably.

The term 'candidate chemical compounds' or 'candidate molecules' preferably connotes chemical compounds and/or molecules being candidates for a further process, in particular chemical compounds having a particular desired set of properties.

The term 'generative model' preferably connotes a model for generating observable data values, given some hidden parameters. Generative models include the following: generative auto encoder, RNN, GAN, Monte-Carlo tree search model, an Ising model or a restricted Boltzmann machine trained in an unsupervised manner etc. (see Exploring deep recurrent models with reinforcement learning for molecule design Workshop Track—ICLR2018 openreview.net/pdf?id=Bk0xiI1Dz, and A Generative Restricted Boltzmann Machine Based Method for High-Dimensional Motion Data Modeling; Computer Vision and Image Understanding 136 (2015): 14-22 arxiv.org/abs/1710.07831, and references therein).

The term 'cost function' preferably connotes a mathematical function representing a measure of performance of an artificial neural network, or a tensor network, in relation to a desired output. The weights in the network are optimised to minimise some desired cost function.

The term 'autoencoder' preferably connotes an artificial neural network having an output in the same form as the input, trained to encode the input to a small dimensional vector in the latent space, and to decode this vector to reproduce the input as accurately as possible.

The term 'tensorial generative autoencoder' preferably connotes an autoencoder used as part of a generative model which includes tensors, tensor networks, or tensorial decompositions, both for input data, the model itself, or for the latent layers.

It should also be appreciated that particular combinations of the various features described and defined in any aspects of the invention can be implemented and/or supplied and/or used independently.

We organize this appendix as follows.

Section 1 is an overview of the technical problems addressed by the GTN system, and a high-level summary of how the GTN system works.

Section 2 is a more detailed discussion of how the GTN system works.

Appendix 2 is a more formal re-statement of the high-level concepts implemented in the GTN system.

Appendix 3 includes technical background, ideas, details, and preliminary results on how the GTN system adds physically-inspired entanglement features to machine learning graph models, using quantum chemistry methods and tensor network algorithms.

Appendix 4 is a paper (A. Hallam, E. Grant, V. Stojevic, S. Severini, and A. G. Green, ArXiv e-prints (2017), arXiv:1711.03357) that demonstrates the potential of tensorial approaches, as used in the GTN system, to affect major, non-incremental, improvements to machine learning.

Appendix 5 is a detailed description of a method for generating an operator expectation value.

Appendix 6 is a summary of graph generative models.

Section 1. Overview

This Section 1 is a high level description of the GTN system. The GTN system implements various aspects and features of the invention. GTN is an acronym for 'generative tensorial networks'.

1.1 Solving the Representation Problem

The representation problem in quantum mechanics was one of the main motivations that led the famous physicist Richard Feynman to propose quantum computers. Exploring the role of entanglement in quantum chemistry has constituted a major line of research in the field ever since, and is thriving today. Entanglement is a purely quantum mechanical feature of many particle systems, causing them to behave in an astonishingly complex, interdependent (i.e. entangled) manner. The potential of efficient quantum mechanical methods to revolutionise drug discovery has been appreciated for a long time (A. Cavalli, P. Carloni, and M. Recanatini, Chemical Reviews 106, 3497 (2006), pMID: 16967914), with chemistry applications amongst the first to be explored on novel quantum chipsets by Google, D-Wave, and IBM, which are designed specifically to address the most intractable aspects of quantum entanglement. An accurate quantum mechanical description of chemical reactions and binding processes is indispensable, both to achieving accurate predictions of molecular characteristics, and for an efficient search through the space of druglike molecules. The main bottleneck to modelling these processes accurately is the exponential cost of representing quantum entanglement.

This is best encapsulated using a tensorial description of quantum states, where by a tensor we mean a multi-dimensional array common in most programming languages. The quantum state of n electrons is described precisely by such rank-n tensors (in general also as a function of all the electron coordinates). The computational memory cost of working with such tensors is exponential in the number of electrons and makes simulations of large quantum systems in their full generality practically impossible on classical computers, but polynomially efficient on universal quantum computers.

A fully general n-electron state of this kind is highly entangled. Thus, it does not admit an efficient description in terms of quantum states of individual electrons, but only a "collective" description via exponentially costly tensors. However, while states relevant for real world applications are entangled, it turns out that they are usually not maximally entangled—and are thus not maximally complex to represent. Optimal representations are achieved by tensor networks having an architecture (Ansatz) designed to capture the entanglement of the state—thus prior knowledge about the state is required, usually coming from theoretical considerations. Tensor networks are a technology that has been developed over the past 25 years mainly in the physics community The potential of efficient quantum mechanical methods to revolutionise chemistry has been appreciated for a long time that can be handled efficiently, together with a method for reconstructing the full rank tensor and calculating values of physically relevant observables.

Figure 31:
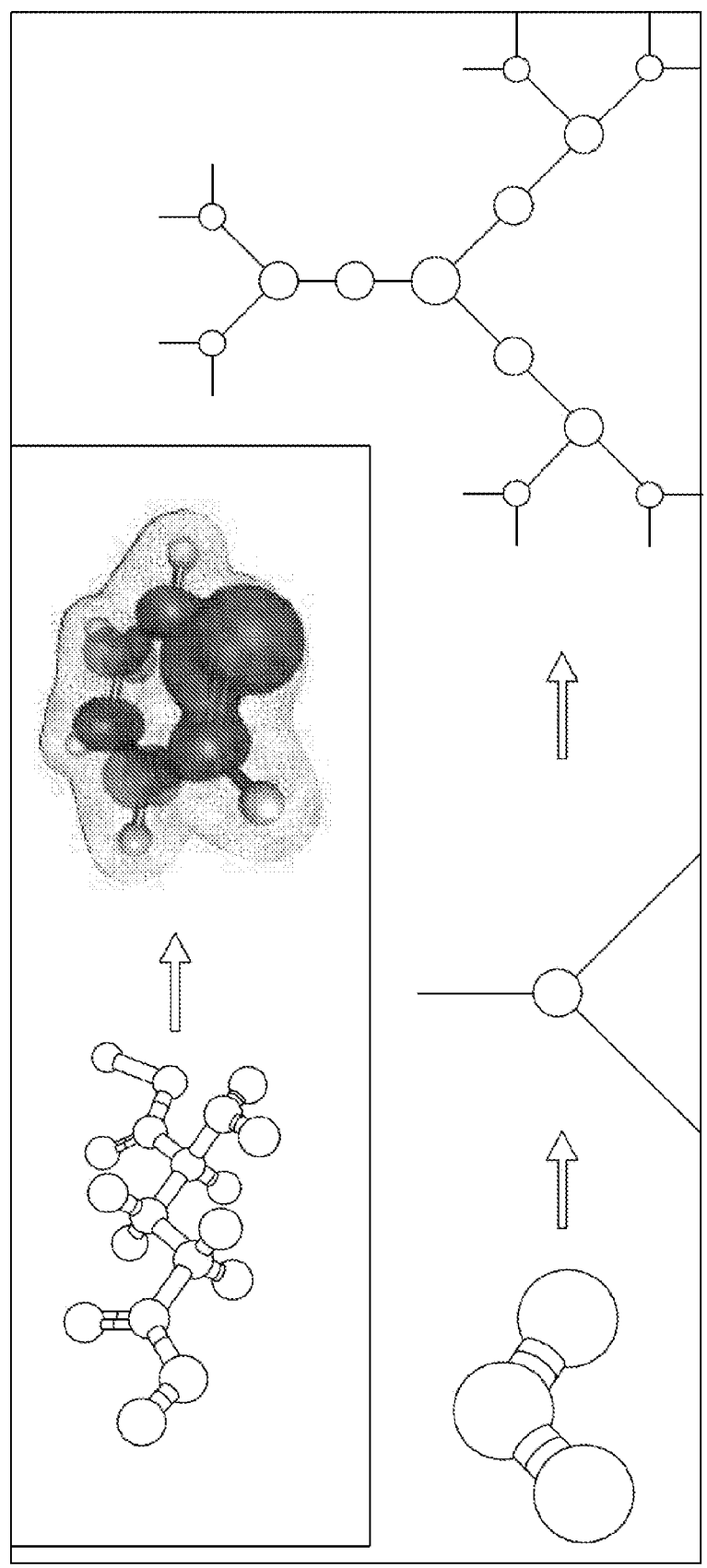
FIG. 31 shows a schematic diagram of a quantum state of a complex molecule and a tree-tensor network representation of the quantum state of $H_2O$.

With reference to FIG. 31, a schematic depiction of a quantum state of a complex molecule (inset), and an example of increasingly complex tree-tensor network representations of the quantum state of H2O are shown.

In the past 2-3 years a surge of interdisciplinary research on the boundary between machine learning and tensor networks has been taking place. It has been realised that tensor networks can be used for standard machine learning problems (E. Miles Stoudenmire and D. J. Schwab, Supervised Learning with Quantum-Inspired Tensor Networks; Advances in Neural Information Processing Systems 29, 4799 (2016) ArXiv e-prints (2016), arXiv:1605.05775), and that deep neural networks can be used to model quantum systems (G. Carleo and M. Troyer, Solving the Quantum Many-Body Problem with Artificial Neural Networks; Science 355, 602 (2017) ArXiv e-prints (2016), arXiv: 1606.02318).

The GTN system is predicated on the realisation that the optimal way to apply machine learning to molecular problems is precisely via the technology of tensor networks.

1.2 Solving the Search Problem

Addressing the search problem requires combining advanced tensor network representations of molecules with deep generative models. The aim is to search the exponentially large search space made up of a set of possible small drug-like molecules (or the space of small molecules considered for other applications) in a meaningful way.

A generative method provides a way of capturing the essence of a certain data set, in order to then generate completely novel, hitherto unseen, data samples. The idea has been around for a long time, and is independent of deep learning (C. M. Bishop, Pattern Recognition and Machine Learning (Information Science and Statistics) (Springer-Verlag New York, Inc., Secaucus, NJ, USA, 2006, N. Shaker, J. Togelius, and M. J. Nelson, Procedural Content Generation in Games, Computational Synthesis and Creative Systems (Springer, 2016)). However, the advance of Generative Adversarial Networks and related models (see Appendix 6) has brought generative methods squarely into the era of deep learning, opening the way to significantly more ambitious applications. Over the past two years this has been impressively demonstrated, enabling the generation of novel images, pieces of music and art, as well as molecular data (R. Gómez-Bombarelli, D. Duvenaud, J. M. Hernández-Lobato, J. Aguilera-Iparraguirre, T. D. Hirzel, R. P. Adams, and A. Aspuru-Guzik, ArXiv e-prints (2016), Automatic chemical design using a data-driven continuous representation of molecules, arXiv:1610.02415). Generative methods are only as good as the quality of the data upon which they are trained. Thus, to generate truly novel molecules, maximally accurate and efficient representations of molecular quantum states need to be employed.

A sophisticated generative method should thus have the capacity to handle advanced tensor network descriptions of molecules as inputs, and to thereby efficiently capture complex properties involving highly entangled quantum mechanical states crucial to drug discovery. GTN is developing the GTN system specifically to address these issues. GTN's models are inspired by standard deep generative models, such as GANs and variational autoencoders (or types of models used to generate graphs, described in Appendix 6), but require custom architectures and tensorial layers to permit compatibility with tensorial inputs.

1.3 the GTN System Technology Pipeline

Figure 32A:
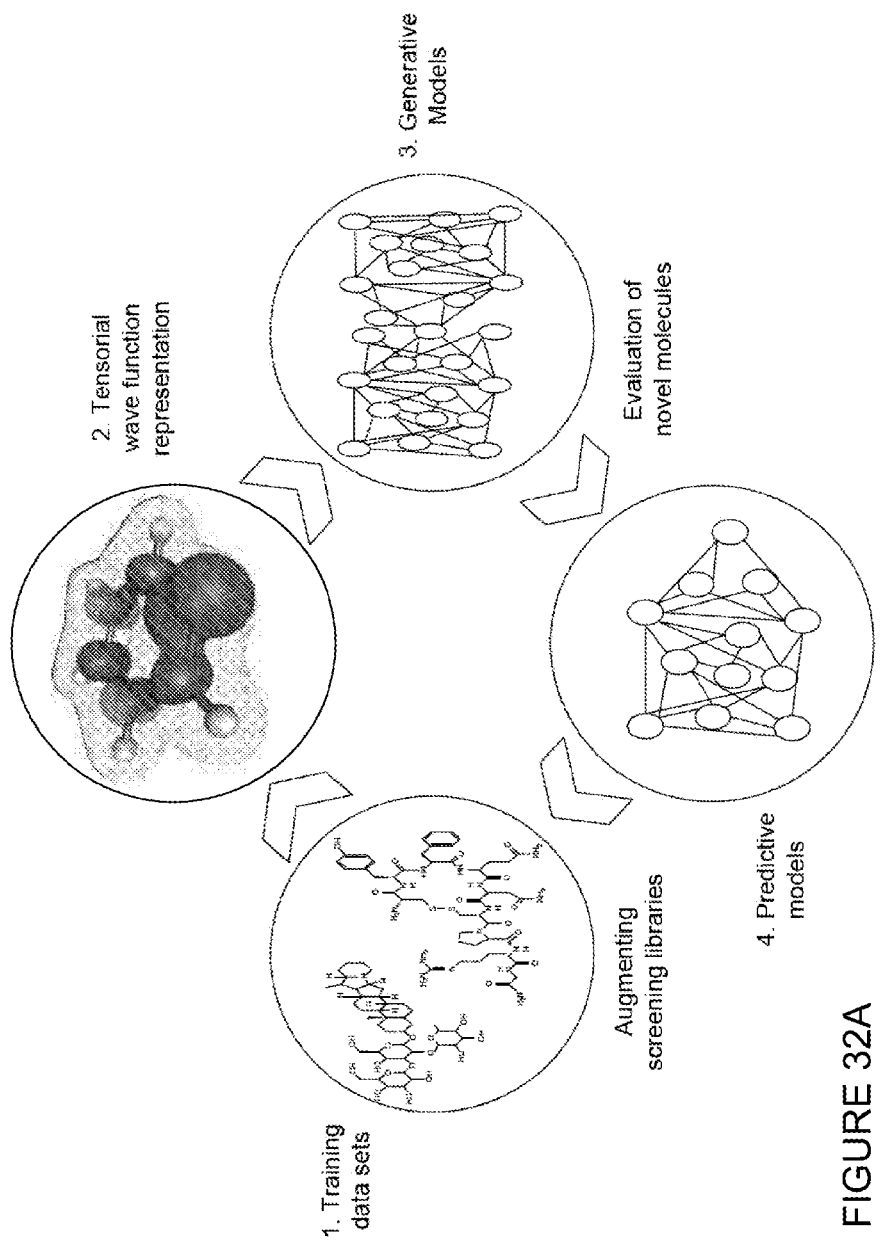
FIG. 32A schematically illustrate the GTN technology pipeline.

With reference to FIG. 32A, the technology pipeline is presented. It starts with a molecular library appropriate for the disease mechanism being addressed (1). Tensorial representations are used to model the molecules in order to capture quantum entanglement, and other quantum and non-quantum correlations (2), and these tensor networks are used as inputs on which the generative network is trained (3). The process is guided by the capacity of the proposed molecules to bind to a target protein (measured by binding affinity Kd, a related assay), as well as any number of relevant optimisation constraints, including absorption, distribution, pKa, log(D), log(P), solubility, permeability and toxicity measures. Predictive models, again utilising tensorial inputs and tensor networks in their construction, are used in order to both screen the generative outputs and add high quality molecules to the original library (4). The iterative cycle is repeated to maximise the quality of proposed molecules.

Figure 32B:
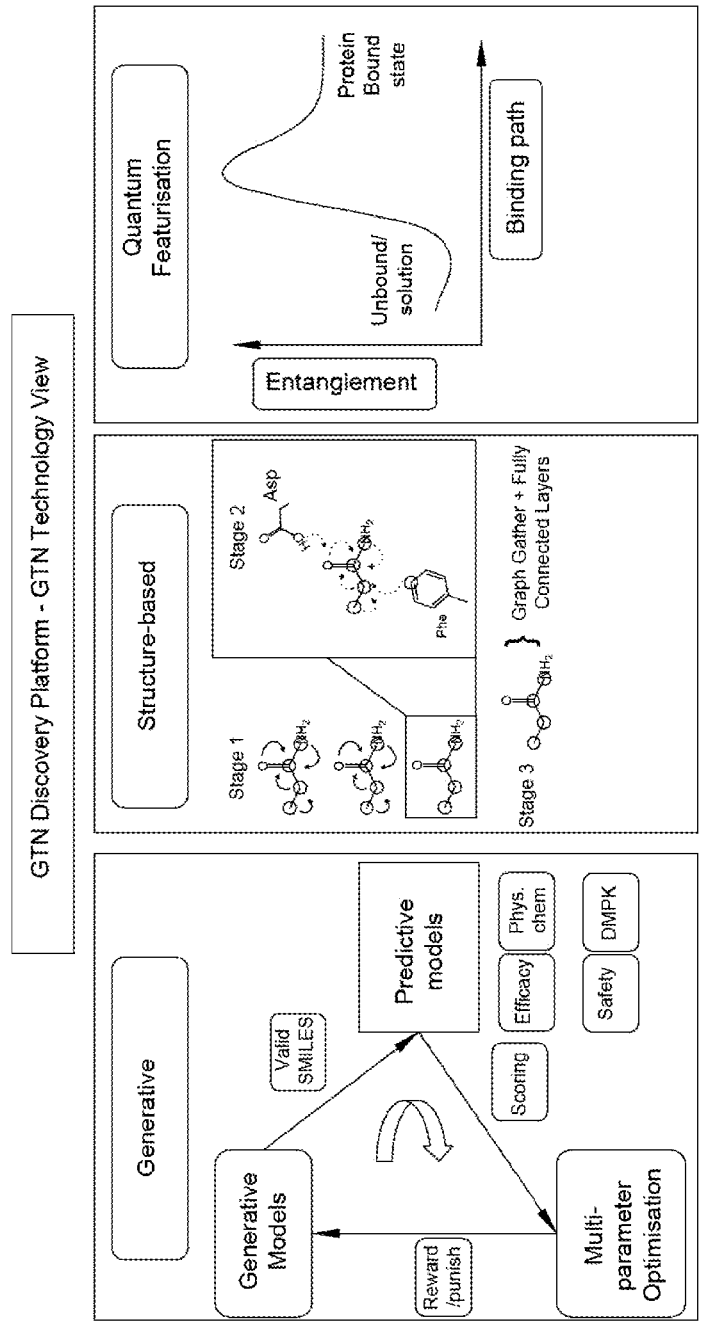
FIG. 32B schematically illustrate the GTN technology platform.

FIG. 32B shows a simple incarnation of the GTN Discovery platform, based on the 'hillclimb' approach, similar to what is described in arXiv:1701.01329. The generative model and predictive models utilise any combination of tensorial methods, both as part of the models and to describe the input data, described in the patent. The output of the generative models is ranked, or the model itself modified to focus on a particular subset of chemical space that satisfies a number of properties. These properties are determined, and the search and/or output of the generative model is guided by the outputs of both structure based models, which incorporate information about the target proteins, as well as ligand based predictive models (i.e. those models that do not utilise target protein information—these can predict e.g. efficacy, physchem properties, binding affinities with respect to some set of proteins), or by similarity with respect to a set of molecules one wants to find close analogues of. Multiparameter optimisation can be performed using any number of standard methods, such as Hillclimb MLE or any number of reinforcement learning variants (see Exploring deep recurrent models with reinforcement learning for molecule design; Workshop Track—ICLR2018; openreview.net/pdf?id=Bk0xiI1Dz).

Structure based machine learning models are sophisticated predictive models that utilise both information about target proteins and small molecules in order to predict binding affinities. Quantum featurisation of input molecules can be used both for ligand based and for structure based models, in the latter case one needs to take into account the quantum mechanical properties both of the binding pocket on the protein and of the ligand. Molecular dynamics methods can be used to improve the results, and also to enlarge the set of data points machine learning models are trained on.

Figure 32C:
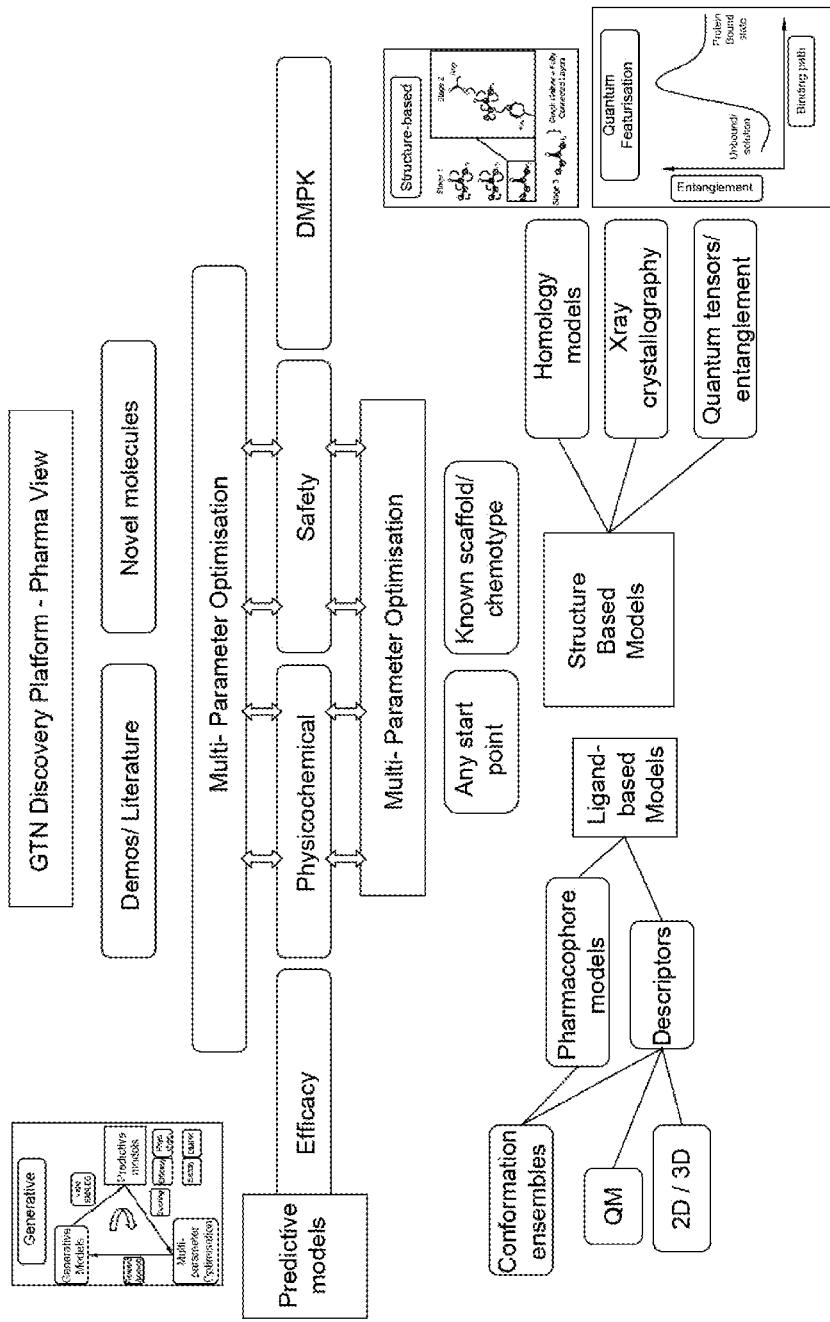
FIG. 32C schematically illustrate the GTN technology platform in the context of the pharma ecosystem.

FIG. 32C is a schematic view of where the technology components described in FIG. 32B fit in to the pharmaceutical industry eco-system.

1.4 GTN vs. Current Approaches

The most sophisticated deep learning approaches for molecular prediction currently utilise graph convolutional networks (D. Duvenaud, D. Maclaurin, J. Aguilera-Iparraguirre, R. Gómez-Bombarelli, T. Hirzel, A. Aspuru-Guzik, and R. P. Adams, Convolutional Networks on Graphs for Learning Molecular Fingerprints ArXiv e-prints (2015), arXiv: 1509.09292; S. Kearnes, K. McCloskey, M. Berndl, V. Pande, and P. Riley, Journal of Computer-Aided Molecular Design 30, 595 (2016), Molecular GraphConvolutions: Moving Beyond Fingerprints J Comput Aided Mol Des (2016), arXiv:1603.00856; T. N. Kipf and M. Welling, Semi-Supervised Classification with Graph Convolutional Networks, ArXiv e-prints (2016), arXiv:1609.02907). At the inputs, molecules are represented in terms of graphs, i.e. two-dimensional ball-and-stick models, together with standard per-atom chemical descriptors. Such inputs already require a significant overhaul of standard neural network techniques, since convolutional or RNN layers designed for image or text data do not respect graph structures. Current generative models for chemistry utilize text input data, in the form of the SMILES representation of molecules (R. Gómez-Bombarelli, D. Duvenaud, J. M. Hernández-Lobato, J. Aguilera-Iparraguirre, T. D. Hirzel, R. P. Adams, and A. Aspuru-Guzik, ArXiv e-prints (2016), arXiv:1610.02415) as this enables many established generative natural language approaches to be used out of the box. However, such approaches are too simplistic to generate truly interesting novel molecules. Some more recent models have attempted graph-to-graph trained generative models (openreview.net/forum?id=SJIhPMWAW), but unresolved issues related to the permutation group gauge symmetry of graph inputs mean that these approaches remain sub-optimal at present. DeepChem, a popular deep learning library for chemistry provides access to many machine learning methods and datasets, including graph convolutional networks, under a unified scalable framework. GTN is interfacing with DeepChem and Tensorflow in order to ensure scalability.

We note also, that graph models can be used in the structure based context, by including both the ligand and the protein binding pocket in a large graph.

Tensorial networks can naturally be used to decompose high rank structures appearing in certain graph models, and this provides a potentially easy way to introduce quantum featurisation and modelling in the context of graph models (see arxiv.org/pdf/1802.08219.pdf) (see Appendix 3).

By implementing tensorial ideas in predictive models, GTN has demonstrated its capacity to consistently beat state-of-the-art predictive models on a number of tasks. A recently publication (A. Hallam, E. Grant, V. Stojevic, S. Severini, and A. G. Green, ArXiv e-prints (2017), arXiv: 1711.03357) provides a proof-of concept demonstration of the disruptive potential of tensor networks, by achieving a compression of deep learning models for image classification by a factor of 160, at less than 1% drop in accuracy.

1.5 GTN System Results

Results are now described where tensorial technology is incorporated in conjunction with two types of graph convolutional networks, the so-called "Weave" and "GraphConv" and "MPNN" networks, and various variants thereof—the current state-of-the-art in predictive models for chemicals ([33] D. Duvenaud, D. Maclaurin, J. Aguilera-Iparraguirre, R. Gómez-Bombarelli, T. Hirzel, A. Aspuru-Guzik, and R. P. Adams, ArXiv e-prints (2015), arXiv: 1509.09292; S. Kearnes, K. McCloskey, M. Berndl, V. Pande, and P. Riley, Journal of Computer-Aided Molecular Design 30, 595 (2016), arXiv:1603.00856). Our current demonstration of the tensorial technology operates at the level of the network, leaving the input data unchanged, and also implements a quantum mechanics inspired machine learning step. The results, displayed in FIG. 33, consistently show incremental improvements of between 1-5% over state-of-the-art approaches.

The implementation of full tensorial molecular inputs may achieve increasingly higher accuracies and begin generating novel molecules for screening. The datasets referenced in FIG. 33, are the following:

ESOL: solubility data for 1,128 compounds.
QM7: 7,165 molecules from the GDB-13 database. Atomization energy for each molecule is determined using ab initio density functional theory.
QM8: 10,000 molecules from the GDB-13 database. 16 electronic properties (atomization energy, HOMO/LUMO eigenvalues, etc.) for each molecule are determined using ab-inito density functional theory.
MUV (Maximum Unbiased Validation): benchmark dataset selected from PubChem BioAssay by applying a refined nearest neighbour analysis. It contains 17 especially challenging tasks for 93,127 compounds and is specifically designed for validation of virtual screening techniques.

Tox21 ("Toxicology in the 21st Century"): contains qualitative toxicity measurements for 8014 compounds on 12 different targets, including nuclear receptors and stress response pathways.

β-Secretase 1 (BACE-1) Inhibitors: Consists of a set of around 1000 molecules inhibiting the BACE-1 protein. IC50 values are available for nearly all of these, and full crystallography ligand-protein structures for a subset. Molecules in the dataset originate from a large variety of sources: pharma, biotechnology and academic labs. The aim is to validate our technology on both classification and regression tasks, on a real-world problem for which the dataset size is relatively small.

"PDBbind: The context is target based design. A curated subset of the PDB database, which has experimentally measured binding affinities for bio-molecular complexes, and provides 3D coordinates of both ligands and their target proteins derived from crystallography measurements. The challenge consists of incorporating both ligand and target space information into the models. The aim is to develop networks that optimally incorporate complex quantum mechanical information, which is crucial to accurately modelling the binding processes, and thereby obtain superior affinity predictions.

In order to achieve a similarly disruptive effect on models relevant to the pharmaceutical industry, the complexity of the molecular input data has to be captured, and compatible networks that effectively deal with such inputs need to be designed.

Section 2. Analysing Exponentially Large Search Spaces

In this section, we will re-frame the discussion of the GTN system in terms of analysing and searching exponentially large spaces, in particular the space of chemical compounds. As noted earlier, the GTN system analyses exponentially large search spaces using tensor networks.

Exponentially large search spaces typically suffer from the 'curse of dimensionality', in that the number of possible solutions increases exponentially with the number of dimensions/modes, making it impractical to analyse such search spaces experimentally.

Exponentially large spaces occur naturally in the context of quantum mechanics. In order to represent the physics of an n-particle system, one needs to in general work with vectors living in Hilbert spaces that are exponentially large in n. Thus, in analysing the search space of say small molecules, one is in general dealing with what could be described as "complexity within complexity": the number of possible molecules is astronomically large simply for combinatorial reasons, and in addition, the description of each of these molecules requires an analysis that uses vectors exponentially large in the number of particles.

The GTN system enables the search, sampling, statistical analysis and visualisation of large search spaces. The method utilises quantum physics inspired tensor networks (from hereon also referred to as tensorial spaces), in the context of generative machine learning models.

The manner in which tensor networks are incorporated into the GTN system can be classified as follows:

Using physics inspired tensor network decompositions within standard machine learning networks, for example to decompose RNNs (recurrent neural networks), convolutional neural networks, graph convolutional neural networks, fully connected layers neural networks, using physics decompositions such as MERA, tree tensor networks, correlated (described in arxiv.org/abs/1711.03357 and references therein). The context here is ML on classical data inputs that utilises tensor decompositions as a mathematical tool, for example to regularise the ML process (by decomposing a fully connected layer as a tensor network), or to introduce priors on the data distribution.

Using tensor networks in place of neural networks, as described here (arxiv.org/abs/1803.09780, arxiv.org/abs/1804.03680 and referees therein). The inputs here need to either be tensor networks themselves, or more generally mathematical objects living in an exponentially large Hilbert spaces. In order for such networks to be applicable to classical data, such as text or image data, it needs to be mapped into a high dimensional Hilbert space using an appropriate feature map. An advantage of this approach is that entanglement measures can be used to design the networks, given the structure of correlations in the training data—something that's virtually impossible with standard neural networks, due to explicit non-linear functions which are fundamental in their construction (sigmoid, ReLU, etc.).

Representing quantum mechanical data (molecules, crystals composed of atoms or molecules, or other physical materials that require accurate quantum mechanical description) using tensor network decompositions.

Using tensor networks to construct machine learning models, specifically so that they are able to optimally work on quantum mechanical input data (review: arxiv.org/abs/1306.2164).

Using tensor decompositions to represent and search through high-rank data, independently of any machine learning or deep learning model (as described here: arxiv.org/abs/1609.00893).

Running pure tensor network based machine learning models on quantum chipsets, by embedding the tensors networks into larger unitary matrices, and performing appropriate measurements (along the lines of methods described here: arxiv.org/abs/1804.03680)

We can generalise the GTN system to a system that analyses exponentially large search spaces using tensor networks.

The GTN system analyses a chemical compound dataset (where the data is either obtained from real world measurements or generated synthetically) so as to determine suitable candidate chemical compounds. The GTN system undertakes the following steps: determining a tensorial space for said chemical compound dataset; correlating the tensorial space with a latent space (and this latent space may itself be a tensor network); and outputting a further dataset, the further dataset comprising a filtered dataset and/or a set of novel chemical compounds (i.e. those not in the original dataset) of candidate chemical compounds. As described above in more detail, tensorial methods could be used here to represent a high rank classical dataset, e.g. graph objects with high rank per-atom descriptors, data living in a multi-dimensional space, or the raw wavefunctions themselves described using tensor networks, and could be used to construct the machine learning network.

Optionally, the machine learning network (which in general contains tensorial components or is a tensor network), operates on a wavefunction space. By way function space we mean, in general, a set of tensor networks each of which describes a quantum state at the input. Thus, the ML network operates on this space, and produces a latent space object. This object is in general a tensor network itself, which in some way compresses the initial wave function data. The latent space object is then applied as input to a decoder ML network (which in general contains tensorial components or is a tensor network itself). The compression procedure could be implemented via a number of renormalisation group steps (such as those described in https://arxiv.org/abs/1509.01522 and in references cited therein), and could include steps that approximate the contraction process, by e.g finding a smaller tensor network, or a tensor network with a smaller bond dimension, in order to approximate the effect of a contraction step. The latter process is performed by minimising the distance in the quadratic form between the state defined in terms of a smaller TN and the full tensor network that results in from the contraction process (an example of such a minimisation procedure see for example eq. (13) in https://arxiv.org/pdf/cond-mat/0409292.pdf, where optimal reduction of bond dimension is achieved for matrix product states).

The latent space may represent a (compressed version) of physically relevant wavefunctions and/or desired properties of candidate chemical compounds. The latent space may represent a (compressed version of a) relevant physical operator decomposed as a tensor network.

The latent space may be chosen and analysed using differential geometry techniques, such as those described in https://arxiv.org/abs/1210.7710.

Optionally, the machine learning network may take samples from a single tensor network as its input data (i.e. the distribution of the input data is determined by a single tensor network).

The further dataset of candidate chemical compounds may be a filtered dataset of candidate chemical compounds and/or a novel dataset of candidate chemical compounds.

The wavefunction space may be represented by tensor networks, which may be one of: complete-graph tensor network state, correlator product state, projected entanglement pair states (PEPS), matrix product states (MPS)/tensor train, and matrix product operator, MERA, or any other type of tensor network or equivalent or generally similar or otherwise useful mathematical object.

The GTN system implements a method that may further comprise mapping a dataset (for example a simple 'classical' image or text dataset) into a higher dimensional tensor. Correlating the tensorial space with a latent space may comprise tensor decomposition or determining an optimal tensor network to describe the mapping of the input data set to a more general description (e.g. a SMILES description to a representation of the molecular electron wavefunction), and/or maximising a cost function, said cost function representing desirable properties of said candidate chemical compounds (as determined by e.g. external predictive machine learning models). Predictive models are also used in the GTN system (see earlier).

Correlating the tensorial space with a latent space may comprise optimising over the latent space (with respect to outputs of predictive models, or similarity with respect to a set of target molecules—e.g. using the Tanimoto index, or other metric) —for example so that it represents desirable properties of said candidate chemical compounds. This can be done in the context of GAN or VAE generative models, with or without the aforementioned tensor network extensions).

Thus, the GTN system uses a suite of models that utilises tensorial decompositions in various forms described above.

Determining the tensorial space for the chemical compounds dataset may comprise encoding the dataset using a generative model, and outputting may comprise decoding using a generative model.

The generative model may comprise an (artificial) neural network, which may be in the form of e.g. a generative auto encoder, RNN, GAN, Monte-Carlo tree search model, an Ising model or a restricted Boltzmann machine trained in an unsupervised manner etc. (see openreview.net/pdf?id=Bk0xiI1Dz, arxiv.org/abs/1710.07831, and references therein) or a model along the lines of those described in Appendix 6. The neural network may comprise, or be replaced by, tensorial decompositions or tensor networks, or may be constructed as a tensor network in its entirety. The tensor network could be a quantum circuit, which could potentially be run on a quantum computer (see arxiv.org/abs/1804.03680)

The method implemented by the GTN system may further comprise outputting a visualisation of the tensorial space (using eigenvalue decompositions, non-linear projections to small and easily visualisable low dimensional manifolds described by tensor network spaces—as described here: arxiv.org/abs/1210.7710).

The candidate chemical compounds may be active elements of a pharmaceutical compound, and/or may be suitable for use in an organic light emitting diode, or any other commercially useful outcome. The chemical compound dataset may be a dataset of possible molecules containing up to a predetermined maximum number of atoms.

We can think of the GTN system as a system for analysing a chemical compound dataset so as to determine suitable candidate chemical compounds, the system comprising: means for receiving a chemical compound dataset; a processor for processing the chemical compound dataset to determine a tensorial space for said chemical compound dataset; a processor for correlating said tensorial space with a latent space; and means for outputting a further dataset of candidate chemical compounds in a desired representation (e.g. SMILES, or a tensor network representation).

We can also think of the GTN system as implementing a method of analysing a dataset so as to determine suitable candidate data points, the method comprising: determining a tensorial space for the dataset; correlating the tensorial space with a latent space; and by optimising over the latent space, outputting a further dataset, the further dataset comprising a filtered dataset and/or a set of novel data points (i.e. those not in the original dataset) of candidate data points (which may be referred to as 'candidate targets').

A generalization is to think of the GTN system as a method of filtering a molecule dataset so as to determine suitable candidate molecules, the method comprising: determining a tensorial space for the molecule dataset; correlating the tensorial space with a latent space, the latent space being used to output physically relevant wavefunctions; and outputting a filtered dataset of candidate molecules.

Another generalization includes a method of using a tensorial generative autoencoder to determine suitable candidate molecules from a dataset.

The GTN system implements a method of restricting a multi-modal search space within a molecule dataset, comprising: representing the molecule dataset in terms of a tensor network; calculating the entanglement entropy using quantum physics methods (for example, as shown in Roman Orus, A practical introduction to tensor networks: Matrix product states and projected entangled pair states, Annals of Physics, Volume 349, p. 117-158) indicative of the correlations in the dataset; and finding an optimal tensor network to capture the amount of entanglement entropy in the dataset (preferably, wherein the term 'optimal' means that the maximal amount of entanglement that can be captured by such a tensor network is close to the actual amount necessary to capture the correlations in the data).

We have noted above that the GTN system enables the search and optimization in large data spaces, and the generation of new hitherto unseen elements via a tensorial generative autoencoder, or another generative method. An example is a space of all possible molecules containing up to a certain maximum number of atoms. The GTN system is designed in particular to analyse spaces plagued by the curse of dimensionality, or equivalently where the data is naturally expressed in terms of tensors (or multi-dimensional arrays) with a large number of modes. In such problems the number of possibilities grows exponentially with the number of modes, e.g. in the present example the number of possible molecules grows exponentially with the number of constituent atoms, and the vector needed to describe the molecular wave function is in general exponentially large for each molecule. The GTN system bypasses the 'curse of dimensionality' by utilizing quantum physics inspired tensor decompositions, which may be constructed in a manner such that the number of parameters grows polynomially in the number of constituents (e.g. atoms or electrons).

In practice the number of such constituents is often of the order of a few hundreds, and by imposing symmetries even much larger systems can be described (including infinitely large systems, by imposing e.g. translation invariance, as described in "Variational optimization algorithms for uniform matrix product states", V. Zauner-Stauber, L. Vanderstraeten, M. T. Fishman, F. Verstraete, J. Haegeman, arXiv: 1701.07035). Tensor networks enable intelligent priors to be picked that, in turn, restrict the search to the space of physically relevant elements ((e.g. electron configurations that occur in configurations corresponding to synthesizable molecules, as opposed to arbitrary electronic wave-functions). The GTN system utilizes these decompositions both by (optionally) applying an appropriate feature map to the input data, and by applying tensor network decompositions in the latent space of the generative autoencoder.

Examples of suitable tensor networks include Complete-Graph Tensor Network States or Correlator Product States, which have been shown to provide extremely accurate description of electron wave functions in molecules, but also multi-scale entanglement renormalization Ansatz (MERA), matrix product states, or tree tensor networks for molecular and other types of data. Matrix product states (DMRG), and tree tensor networks have been used widely for quantum chemistry (see e.g. arxiv.org/abs/1405.1225 and references therein).

Such priors may be picked by considering the details of the physics under study. For example, the theoretical analysis of local massive Hamiltonians has demonstrated that the entanglement entropy of grounds states of such Hamiltonians increases as the area of the boundary of the region under study. Matrix product states (MPS), or projected entanglement pair states (PEPS) in more than one spatial dimension, are designed with these entanglement properties built in, and are thus the suitable tensor networks to study such ground states. MERA tensor networks provide the optimal description for ground states in the massless limit, that is, for critical, or (equivalently) scale-invariant systems. The general structure of correlations of electrons in a molecule is captured by the aforementioned Complete-Graph Tensor network states. As a further example, tree tensor networks have been shown to capture correlations of image data well, and to be closely related to convolutional neural nets with non-overlapping filters (see Levine, Yoav; Yakira, David; Cohen, Nadav; Shashua, Amnon, Deep Learning and Quantum Entanglement: Fundamental Connections with Implications to Network Design, eprint arXiv:1704.01552). The present invention may make use of techniques which capture the correlations in the data as closely as possible.

In the GTN system, we see an optimization with respect to the tensorial space, which can refer to either the space resulting from the feature map of the inputs, or to the latent space (or both). Controlled optimization (a tailored search) is performed in the tensorial space with respect to complex cost functions that quantify the desirable properties, which are to be maximized (or minimized, as appropriate) over the search space. The cost function can be a complex function of the outputs of the tensorial autoencoder. For example, the output may be a tensorial description of the quantum state of the molecule, and one may optimise with respect to complex correlation functions calculated from this output tensor network (using standard physics methods, see Roman Orus, A practical introduction to tensor networks: Matrix product states and projected entangled pair states, Annals of Physics, Volume 349, p. 117-158)).

The GTN system enables the visualization of the high dimensional space with the aim of e.g. (but not restricted to) understanding the neighbourhood of a known point in order to find optimal nearby elements, visualizing projections onto subspaces (sub-manifolds) of the tensorial space, that aids the understanding of which parts of (and directions in) the latent space are the most relevant for the optimization. Examples of visualization techniques include (but are not limited to) projections onto smaller tensorial latent spaces that are more readily visualized, understanding of entanglement entropy (described in Roman Orus, A practical introduction to tensor networks: Matrix product states and projected entangled pair states, Annals of Physics, Volume 349, p. 117-158) or separation rank (described in Levine, Yoav; Yakira, David; Cohen, Nadav; Shashua, Amnon, Deep Learning and Quantum Entanglement: Fundamental Connections with Implications to Network Design, eprint arXiv: 1704.01552) to visualize correlations and optimize the network architecture, visualization via higher order correlation functions and spectra of density matrices and correlation matrices (described in Stojevic, Vid; Haegeman, Jutho; McCulloch, I. P.; Tagliacozzo, Luca; Verstraete, Frank, Conformal data from finite entanglement scaling, Physical Review B, Volume 91, Issue 3, id. 035120), visualisation of tangent directions to the manifold of tensor network states in order to determine for example the best directions for the optimisation of a given quantity of interest (as described in Post-matrix product state methods: To tangent space and beyond, Haegeman, Jutho; Osborne, Tobias J.; Verstraete, Frank, Physical Review B, vol. 88, Issue 7, id. 075133).

The GTN system aims to find an optimal final product that is composed of a large number of constituents (for example an alloy composed of individual constituent metals, a food supplement or a cosmetic product composed of a large number of ingredients). In such a scenario it is assumed that the number of constituents is large enough so that an exhaustive experimental search is not possible due to the 'curse of dimensionality', and the dataset of final products with experimentally measured properties of interest (which are capable of being optimised) is an exponentially small subset of all possible final products. The tensor network used to represent interesting regions of the exponentially large space needs to be determined using an intelligent prior based on available data.

Figure 34:
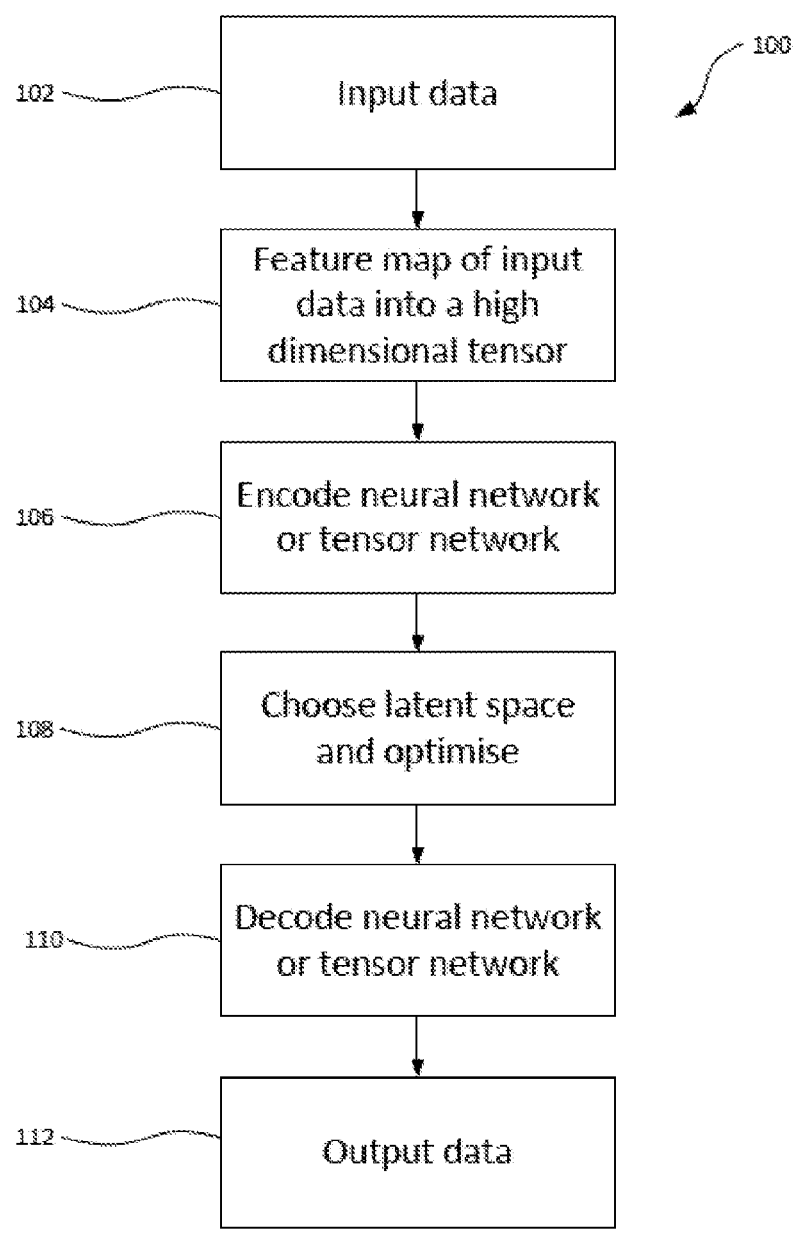
FIG. 34 shows flow diagram of a method of filtering a molecule dataset.

FIG. 34 is a flow diagram of a method 100 of applying a tensorial autoencoder to a dataset. There are two distinct optimisations: the first optimisation corresponding to training the autoencoder, where the cost function aims to, roughly speaking, minimise the difference between the outputs and in input whilst also minimising the amount of information (i.e. compressing the amount of information) that needs to be passed through the latent space (utilising any of the standard cost measures for this difference, see for example Tutorial on Variational Autoencoders, Doersch, Carl, arXiv:1606.05908). Specific steps for the autoencoder optimisation are as follows.

In an initial step 102, input is received. The input data comprises a string, vector, matrix, or higher dimensional array (i.e. a tensor).

In a second step 104, a feature map is applied to the input data to transform it into a high dimensional structure, with the number of modes equal to the number of input data points. This step is optional, and may not be performed if the input data is already a high dimensional tensor. A suitable feature map is shown in Miles Stoudenmire, E.; Schwab, David J., Supervised Learning with Quantum-Inspired Tensor Networks, Advances in Neural Information Processing Systems 29, 4799 (2016).

In a third step 106, the data is encoded using a neural network (or optionally a tensor network), in particular an autoencoder.

In a fourth step 108, a latent space, obtained in terms of the action (i,e, contraction) of a tensor network/neural network combination on the inputs. The network is chosen to fit the problem under investigation in a manner that is compatible with the inputs. The latent space forms a compressed representation of any input. In the case of a molecule dataset, complete-graph tensor network latent spaces (shown in Marti, Konrad H.; Bauer, Bela; Reiher, Markus; Troyer, Matthias; Verstraete, Frank, *Complete-graph tensor network states: a new fermionic wave function ansatz for molecules*, New Journal of Physics, Volume 12, issue 10, article id 103008, 16 pp. (2010)) or correlator product state latent spaces (shown in Vid Stojevic, Philip Crowley, Tanja Đurić, Callum Grey, Andrew Green, *Time evolution and deterministic optimization of correlator product states*, Physical Review B, Volume 94, Issue 16, id. 165135) may be used to represent input molecules, both of which show accurate descriptions of electron wave functions in molecules. Matrix product states, and tree tensor networks often give very accurate descriptions of molecular electron wavefunctions (see arxiv.org/abs/1801.09998 and references therein)

In a fifth step 110, the data is decoded using the neural network (or tensor data).

In a sixth step 112, output data is produced, in the form of a string, vector, matrix, tensor, or a tensor network.

The above compression procedure could be implemented via a number of renormalisation group steps (such as those described in https://arxiv.org/abs/1509.01522 and in references cited therein), and could include steps that approximate the contraction process, by. e.g finding a smaller tensor network, or a tensor network with a smaller bond dimension, in order to approximate the effect of a contraction step. The latter process is performed by minimising the distance in the quadratic form between the state defined in terms of a smaller TN and the full tensor network that results in from the contraction process (an example of such a mimisation procedure see for example eq. (13) in https://arxiv.org/pdf/cond-mat/0409292.pdf, where optimal reduction of bond dimension is achieved for matrix product states).

Figure 35:
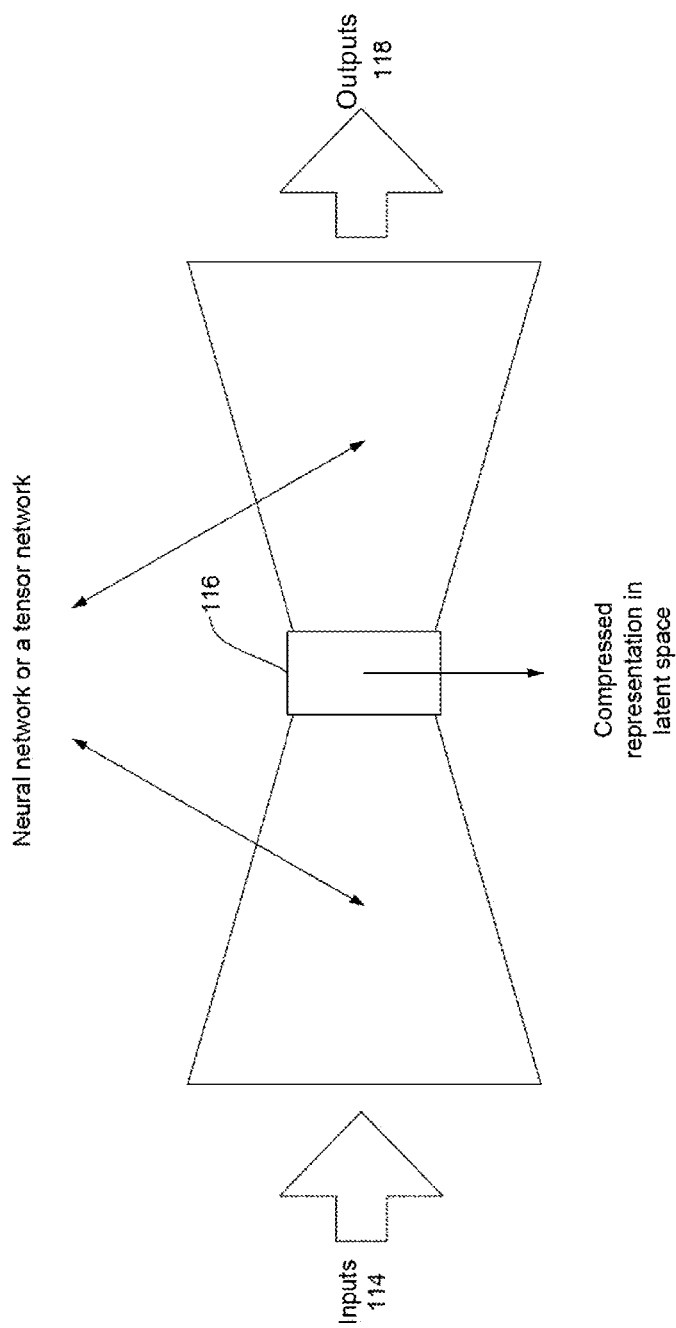
FIG. 35 shows a schematic diagram showing how data is processed to train an autoencoder.

FIG. 35 is a schematic diagram showing how data is processed in the method 100 to train the autoencoder. Input data 114 is encoded into a chosen latent space 116 using a neural network or tensor network. The compressed representation of the data in the latent space is then decoded using the neural network or tensor network, thereby producing outputs 118. The weights in the neural network, or constituent tensors in a tensor network, are optimised to minimise the difference between outputs 118 and inputs 114.

In one embodiment, input data in the form of a tensor is received. A tensor network provided as an autoencoder is used to encode the input data into a complete-graph tensor network latent space, which is used to capture a compressed representation of the inputs. The tensor network is then used to decode the data in the latent space, producing an output also in the form of a tensor.

A second possible optimisation aims to determine an optimum in the latent space with respect to a cost function representing some desired property. For example, the desired properties may comprise water-octanol partition coefficient in drug design (or can be any of the descriptors listed in for example Quantitative Structure-Activity Relationship (QSAR) Models of Mutagens and Carcinogens, Romualdo Benigni, CRC Press, 26 Feb. 2003, or other standard quantum mechanical quantities that one can calculate directly from the molecular wavefunction). Depending on details of the steps described above, the latent space might be a tensorial object, or a simple vector (which is the usual setup in an autoencoder), or some other mathematical construct such as a graph. The output determined by a given element of the latent space (and in particular the optimal element of the latent space) will in general not be a part of the original dataset. For this reason the approach is termed 'generative', and the novel elements may lie anywhere in an exponentially large space. In particular, in the context of searching through spaces of possible chemical compounds, which is exponentially large in the number of constituent atoms in the compound, the generative tensorial approach described here will explore regions of the huge space of possible compounds not accessible to other methods. The output data may alternatively or additionally be a filtered version of the input data, corresponding to a smaller number of data points.

A further possible optimisation would work on a type of latent space that is used to sequentially produce a molecule, as in the case of the GCPN model described in Appendix 6.

Figure 36:
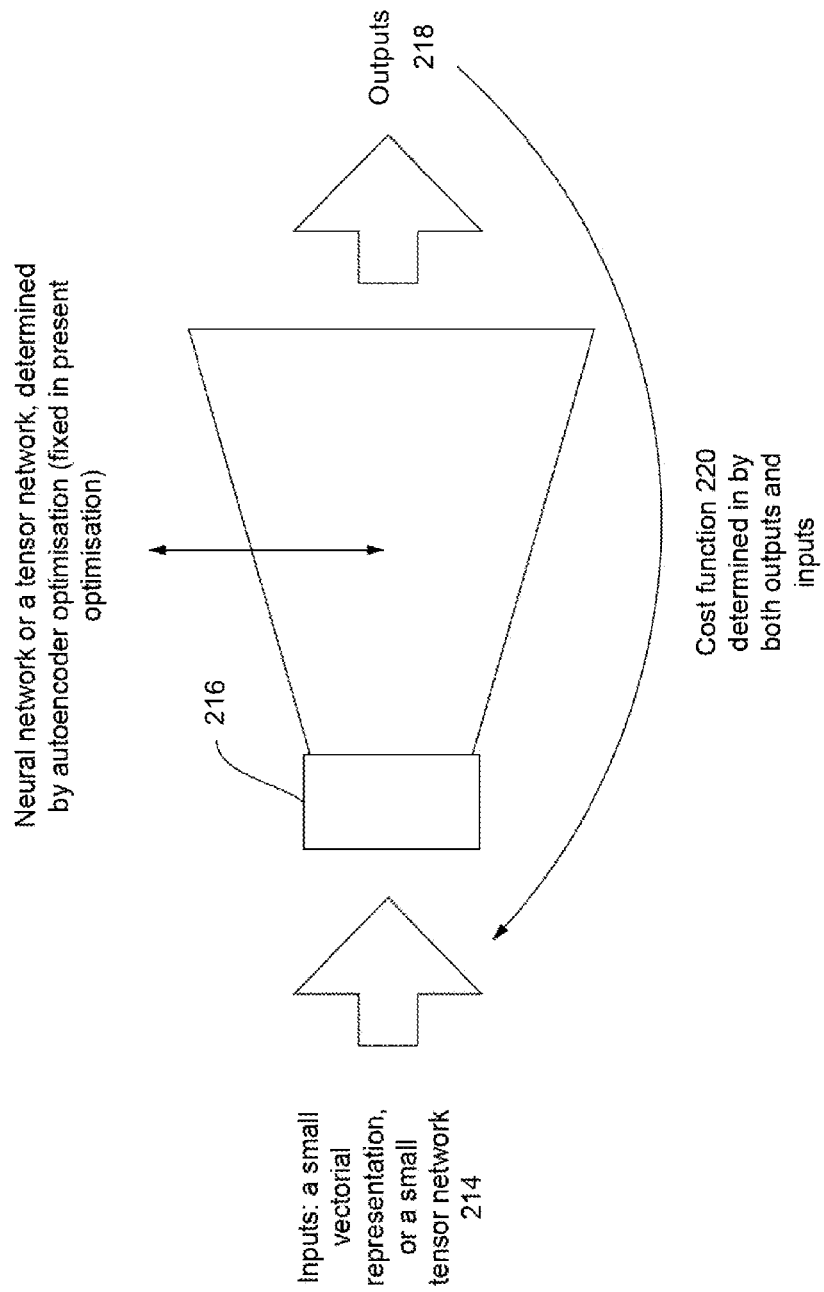
FIG. 36 shows a schematic diagram showing how data is processed to determine an optimum in the latent space.

FIG. 36 is a schematic diagram showing how data is processed to determine an optimum in the latent space, which is represented by some small tensor network (which captures a compressed representation space for input molecules). Inputs 214 (in the form of a small vectorial representation or a small tensor network) are applied to a chosen latent state 216. The neural network or tensor network (determined by the particular optimisation of the autoencoder, as shown in FIG. 2) is applied to the elements in the latent space to produce outputs 218. The inputs are optimised by minimising (or maximising, as appropriate) a cost function 220.

In one embodiment, a tensor network is applied to a space of chemical compounds described as complete-graph tensor. Upon contraction this yields the latent representation. The optimisation is performed over the small tensor network representing the latent space to find an optimum with respect to the water-octanol partition coefficient of a compound is then applied to the latent space, generating an output in the form of a dataset of novel chemical compounds (redecoded to a tensor network).

Figure 37A:
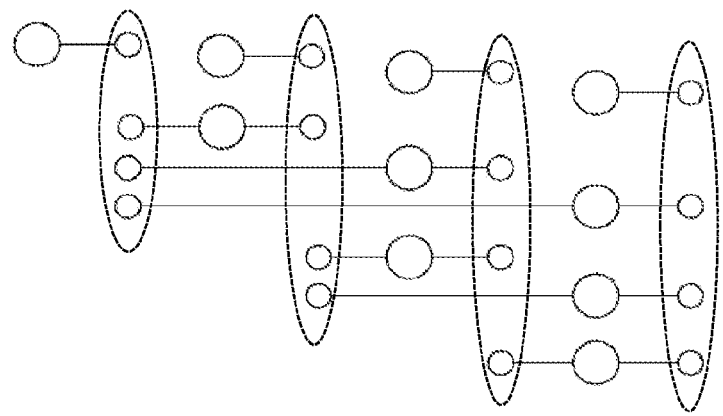
FIG. 37 show schematic representations of suitable tensor networks for use with the method.
Figure 37B:
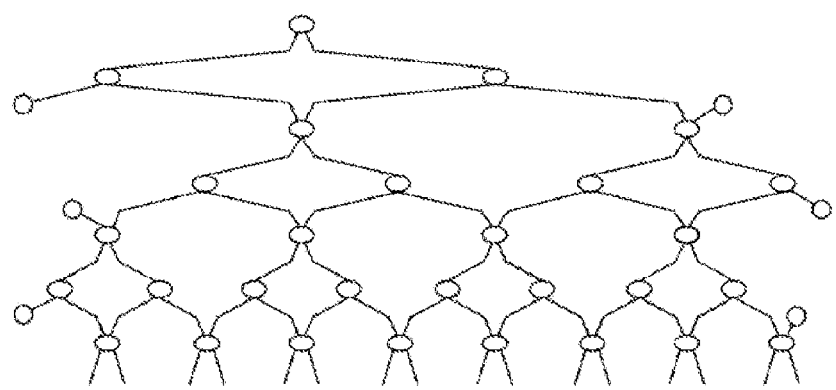
Figure 37C:
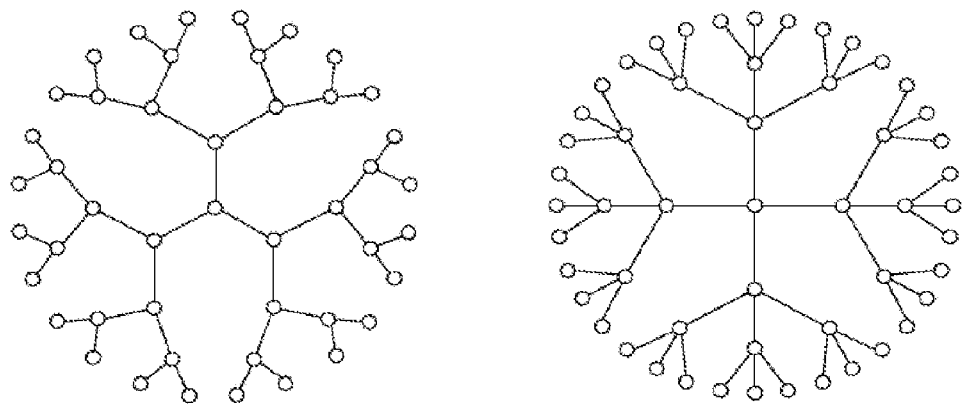

FIGS. 37a-c show schematic representations of suitable tensor networks for use with the method 100. FIG. 4a shows a schematic representation of a complete graph tensor network state (CGTN) (from Vid Stojevic, Philip Crowley, Tanja Đurić, Callum Grey, Andrew Green, Time evolution and deterministic optimization of correlator product states, Physical Review B, Volume 94, Issue 16, id. 165135), which also corresponds to a specific restricted type of a correlator product state. Circles and dotted ovals represent different kinds of tensorial mappings. As mentioned, both of these tensor networks show accurate descriptions of electron wave functions in molecules. FIG. 4b shows a schematic representation of the MERA tensor network (from "Tensor Network States and Geometry", Evenbly, G.; Vidal, G.; Journal of Statistical Physics, Volume 145, Issue 4, pp. 891-918) which may provide an optimal description for ground states in the massless limit. FIG. 4c shows schematic representations of tree tensor networks (from "Efficient tree tensor network states (TTNS) for quantum chemistry; Generalizations of the density matrix renormalization group algorithm", Nakatani, Naoki; Chan, Garnet Kin-Lic, Journal of Chemical Physics, Volume 138, Issue 13, pp. 134113-134113-14 (2013)), which capture correlations of image data well.

Figure 38:
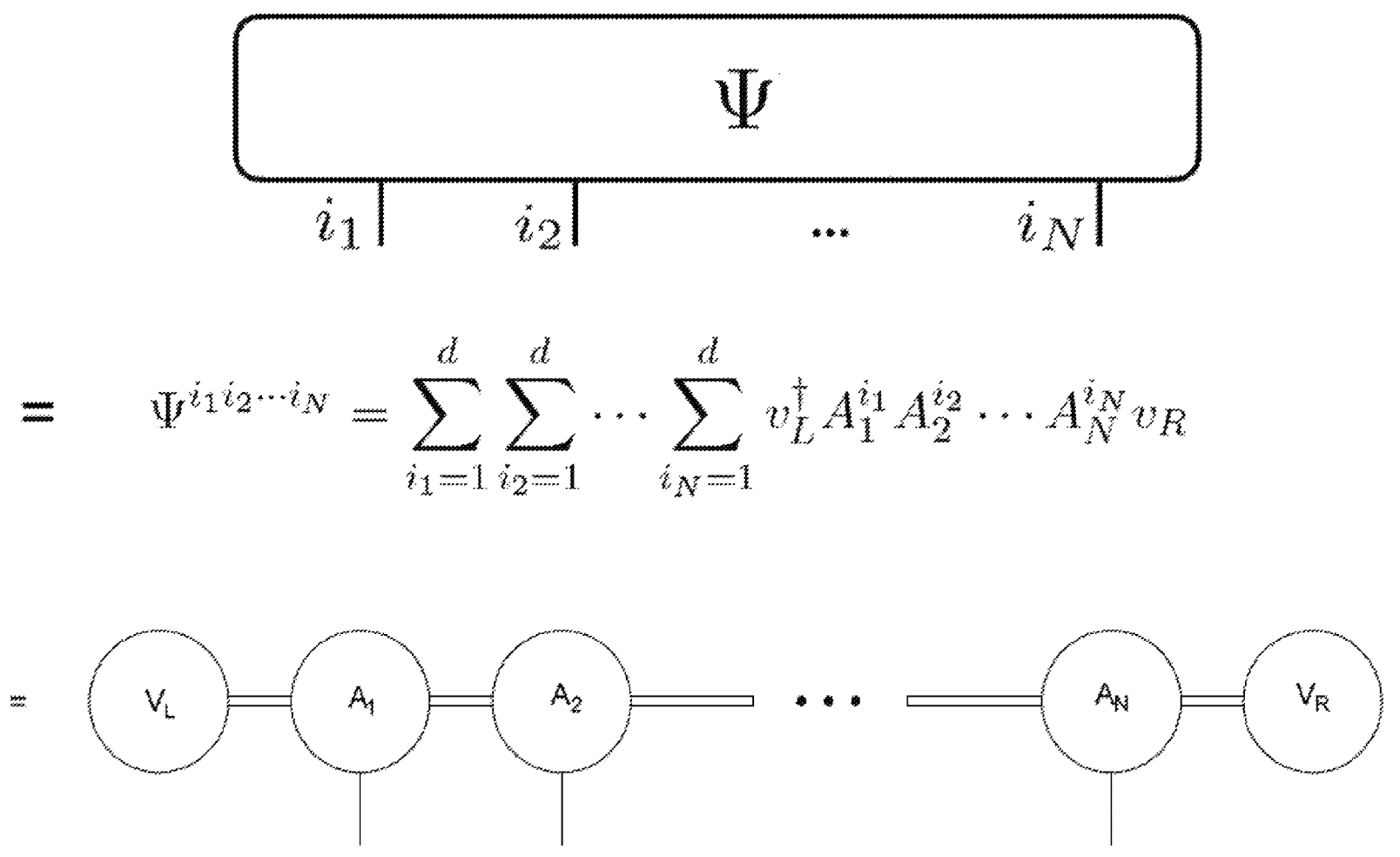

FIG. 38 is a diagram showing an example of a decomposition of a tensor into a matrix product state. Such an operation is performed in the fourth step 108 of the method 100. The matrix product state shown is also known as a 'tensor train'. Examples of possible decompositions are shown in Roman Orus, A practical introduction to tensor networks: Matrix product states and projected entangled pair states, Annals of Physics, Volume 349, p. 117-158 and Cichocki, A.; Lee, N.; Oseledets, I. V; Phan, A-H.; Zhao, Q.; Mandic, D., Low-Rank Tensor Networks for Dimensionality Reduction and Large-Scale Optimization Problems: Perspectives and Challenges, eprint arXiv:1609.00893.

d is the size of each of the modes of the order N tensor $\Psi$ (which is assumed to be the same for all modes in this case, however, this need not be the case. For every value of $i_\alpha$, $A^{i_\alpha}$ is a d×d matrix.

FIG. 39 shows a schematic decomposition of a mode-5 tensor as a matrix product state (or 'tensor train').

Figure 40:
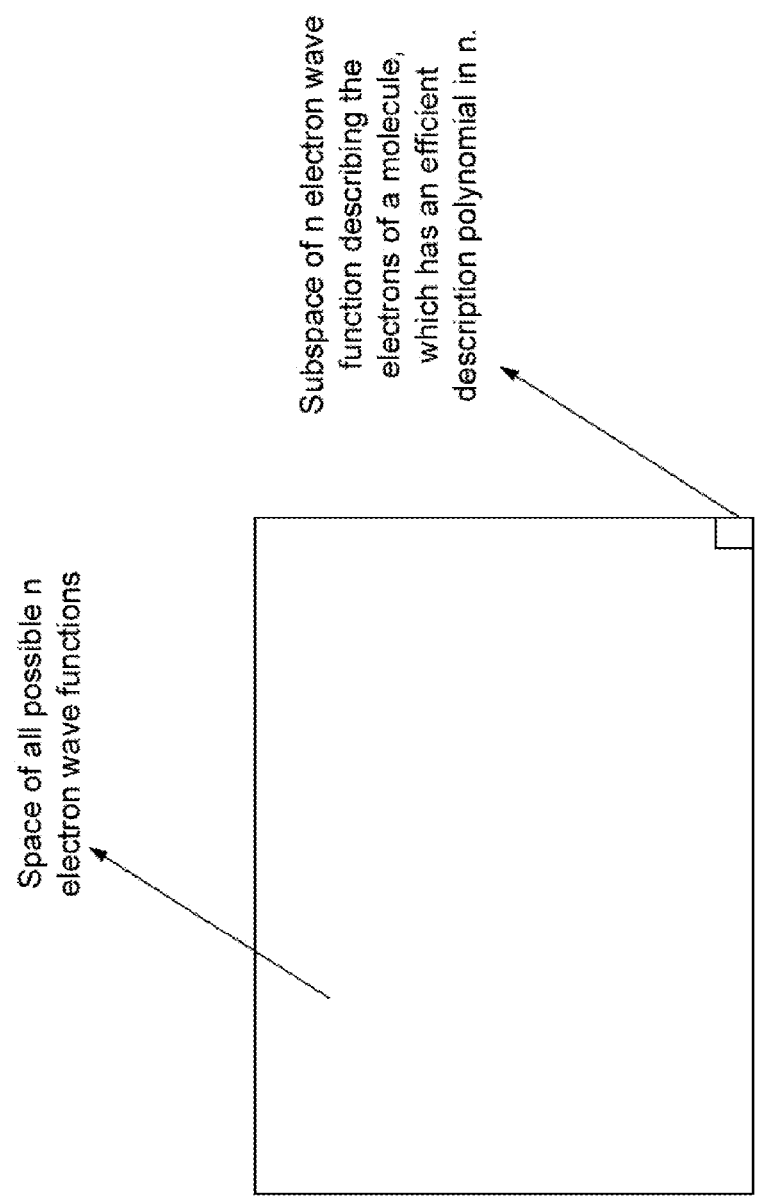
FIG. 40 shows a schematic drawing depicting the effect of a quantum physics tensor decomposition.

FIG. 40 is a schematic drawing depicting the effect of a quantum physics tensor decomposition, reducing a state that is exponentially expensive, in the number of modes, to store and manipulate, to one which imposes a prior and whose representation is polynomial in the number of modes. The exponentially expensive state forms part of the 'curse of dimensionality', in that the size of the quantum wave function is exponential in the number of particles.

APPENDIX 2

Re-Statement of Core Concepts

We will start with schematic illustrations FIG. 46-51.

Figure 46:
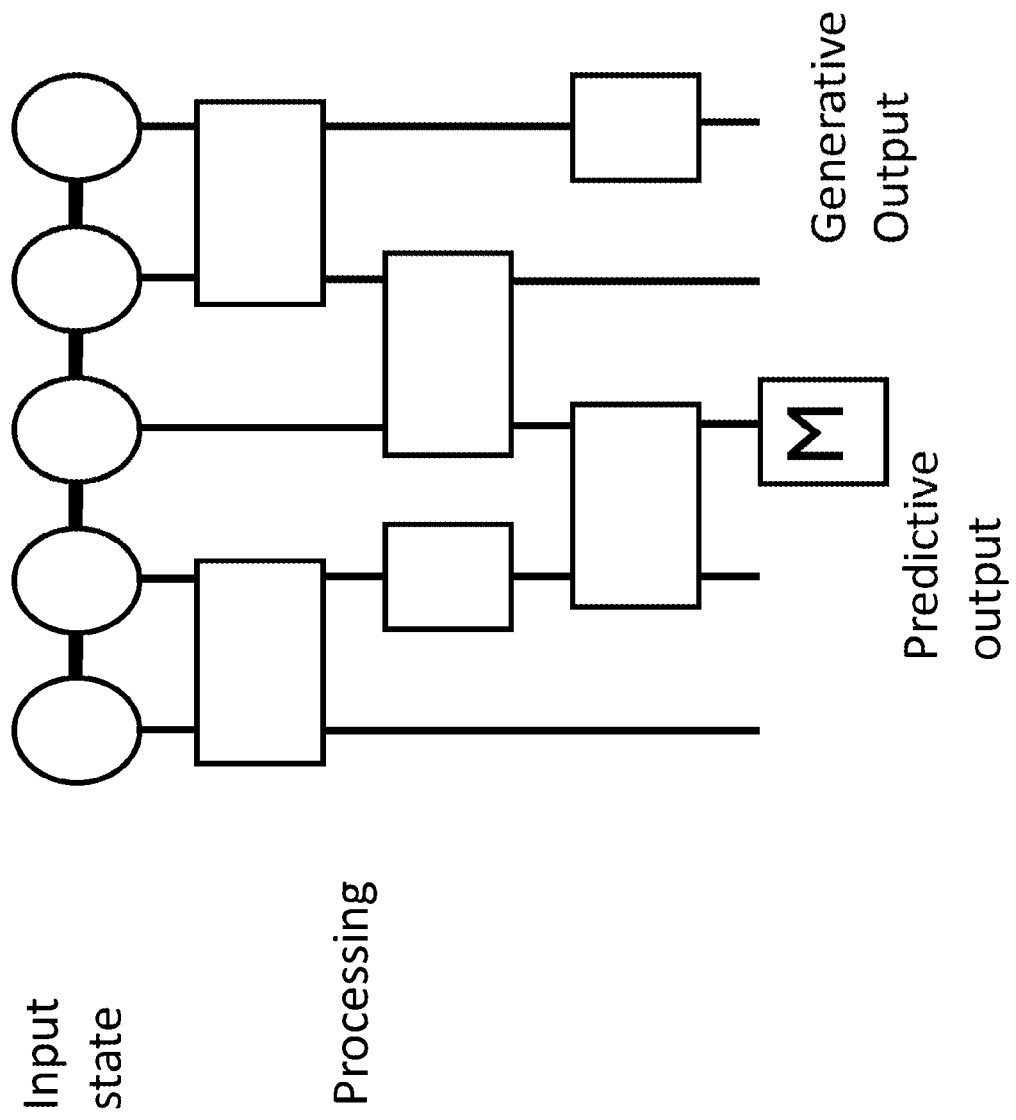
FIG. 46 schematically represents processing tensor network input states to produce a predictive output and a generative output.

FIG. 46 shows an Input state: a general tensor network state—in this example a matrix product state. In the Processing stage, the input is processed by a general tensor network (or, in full generality, a neural network/tensor network hybrid) —in this example a quantum circuit consisting of 1- and 2-qubit unitary gates. If the transformation is to be computable classically, every contraction in the tensor network has to be storable as an efficiently computable tensor network state. The quantum circuit example might constitute a feasible computation only on a quantum chipset. The Processing stage outputs a Predictive output: in order to obtain a regression or classification output, one can perform a quantum measurement on a desired number of qubits, specified by M here, (this can be a real quantum measurement, or a classically simulated version thereof, see arxiv: 1804.03680), or, classically, pass a subset from the output layer, through an e.g. fully connected set of neural network layers, or e.g. a softmax classifier.

Generative Output: the circuit can itself generate samples. Or, classically, the output vector (or an element of some vector subspace thereof), can be used to reproduce the input via a decoder network, in e.g. a variational autoencoder setting.

Figure 47:
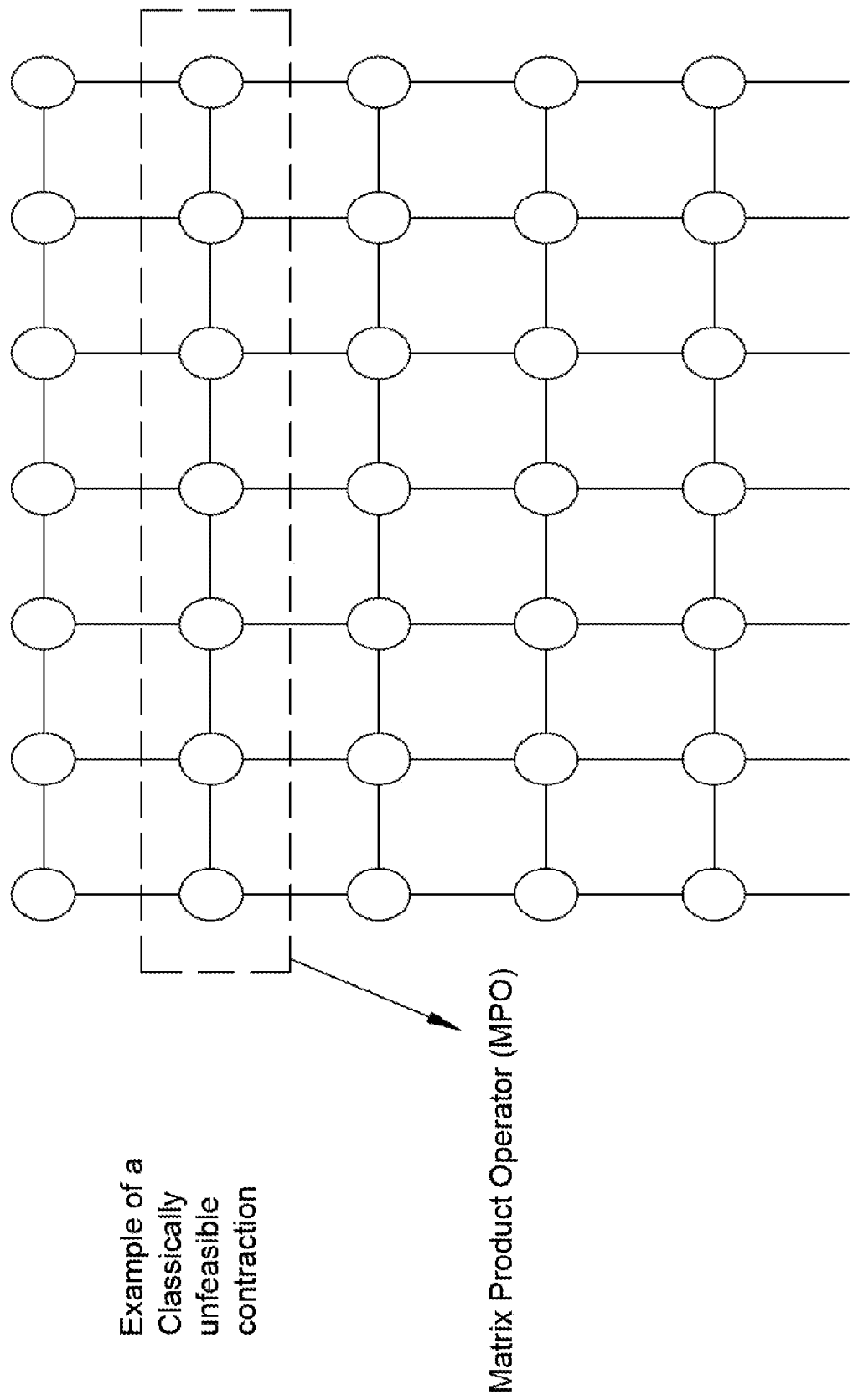
FIG. 47 schematically represents a tensor network of matric product operators.

FIG. 47 is an example of a classically unfeasible contraction: following on from FIG. 46, this is an example of an application of a tensor network of N matrix product operators (MPOs) (in this diagram 4) to an input MPS in succession. This contraction is in general exponential in N. For example, the naive matrix product bond dimension, of the result of the MPO applied to the initial MPS is $D^{(N+1)}$. For a classical contraction of this network to be feasible in general, one therefore has to apply an approximation scheme, for example, a projection to a lower dimensional MPS after every application of an MPO. If the approximation scheme is sufficiently accurate, a classical scheme is possible, otherwise, for a class of MPOs that can be mapped to a quantum circuit, a quantum computing solution becomes necessary. Methods for projecting to smaller MPS, using e.g. singular value decomposition are described here arxiv.org/abs/1306.2164, and in cited references.

Figure 48:
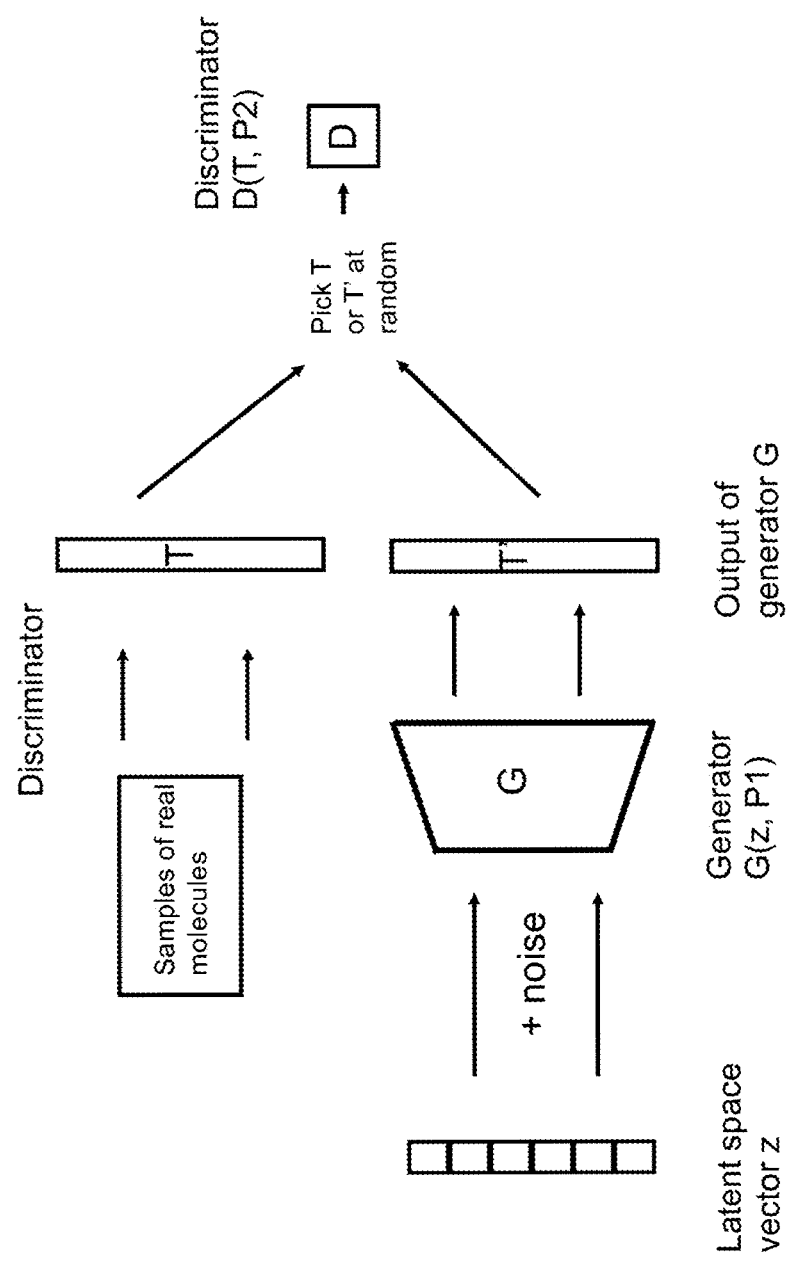
FIG. 48 schematically represents the overall scheme of tensor networks outputting to a generative adversarial network.

In FIG. 48 we show the overall schematic for a generative tensorial adversarial network. For the top limb, samples of real molecules are fed to Discriminator D; molecules are represented as tensor networks T, using quantum mechanics/quantum chemistry methods.

For the lower limb, we start with latent space vector z: traditionally a small dimensional vector (small compared to the dimensionality of the data), but can itself be represented by a 'small' tensor network, is combined with noise and fed to Generator G(z, P1) —in general a neural network/tensor network hybrid, taking z as input, and a function of internal tensors/weight matrices P1. The output of generator G: in general the generator G outputs a tensor network T' description of a molecule.

The system picks T or T' at random and then discriminator D(T, P2) decides whether T/T' is a 'real' or a 'fake' sample. Discriminator network contains internal tensor/weight matrix parameters P2.

Training is a min-max game: Maximise D(T), and minimise D(T') for P2, and maximise D(T') for P1. For details on GANs in general, see medium.com/ai-society/gans-from-scratch-1-a-deep-introduction-with-code-in-pytorch-and-tensorflow-cb03cdcdba0f and references therein.

Figure 49:
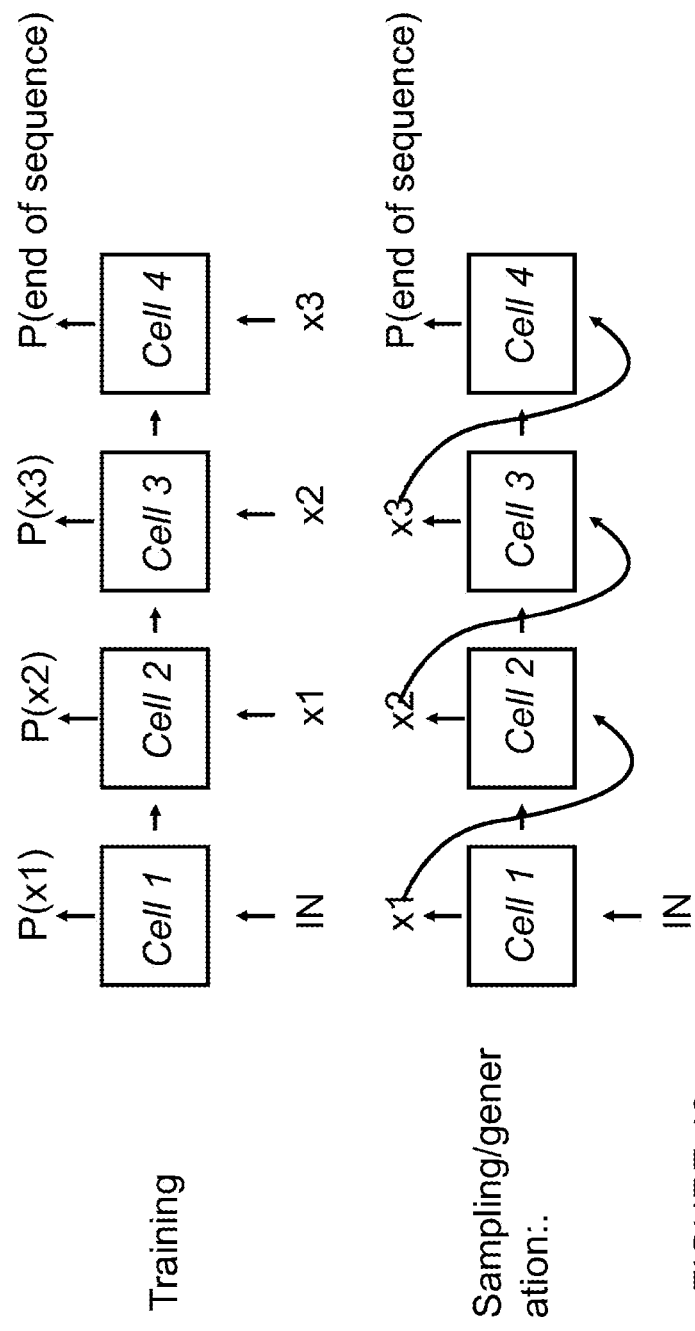
FIG. 49 schematically represents a RNN generative model.

In FIG. 49, we have a schematic of a RNN generative model. The standard RNN approach works on sequences, and is not straightforwardly amenable to working on tensor network data, which is not generally sequential. Nevertheless, a general tensorial RNN can be composed in a manner where each cell is built up from any of the listed combinations of neural networks/tensor networks. A generalised RNN can be trained to predict a sequence of tensors in a linear tensor network.

The system trains the model on sequences (here: {x1, x2, x3, eos}, to predict the next element of a sequence.

Sampling/generation: initialised randomly at IN, the outputs of the model are fed into the next cell along, until EOS (end of sequence) is reached.

Figure 50:
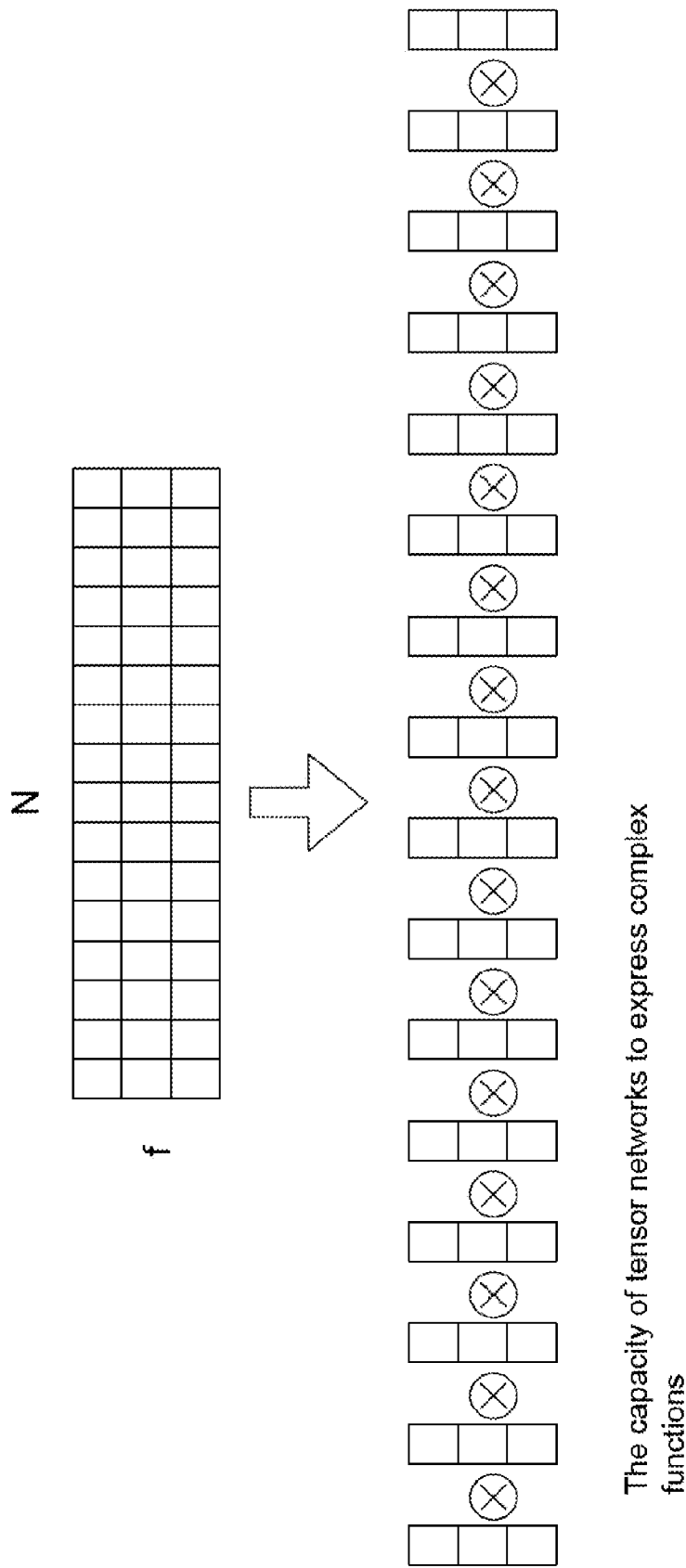
FIG. 50 schematically represents the capacity of tensor networks to express complex functions.

In FIG. 50, we show the capacity of tensor networks to express complex functions. Classical data is represented by a small rank tensor: in this example a matrix of dimensions f×N. This data is first mapped into a huge Hilbert space, in this example by taking a tensor product of all the individual f×1 vectors in the data matrix. The size of this object is $f^N$. Tensor networks are constructs involving multi-linear operations, meaning that the reconstruction of the original high rank tensor is obtained by contractions. Unlike for neural networks, there are no explicit applications of non-linear functions (such as ReLU or sigmoid functions). The power of tensor networks lies in the fact that these multi-linear operations are applied in an exponentially large Hilbert space (see e.g. arxiv.org/abs/1803.09780 for an explanation of an aspect of these ideas), as a trade-off for an explicit non-linearity. Whilst classical data needs this somewhat artificial feature map in order to be inputted into tensor networks, quantum data is naturally expressed in terms of high rank tensors, and associated tensor networks (see arxiv.org/abs/1306.2164 and references therein).

Figure 51:
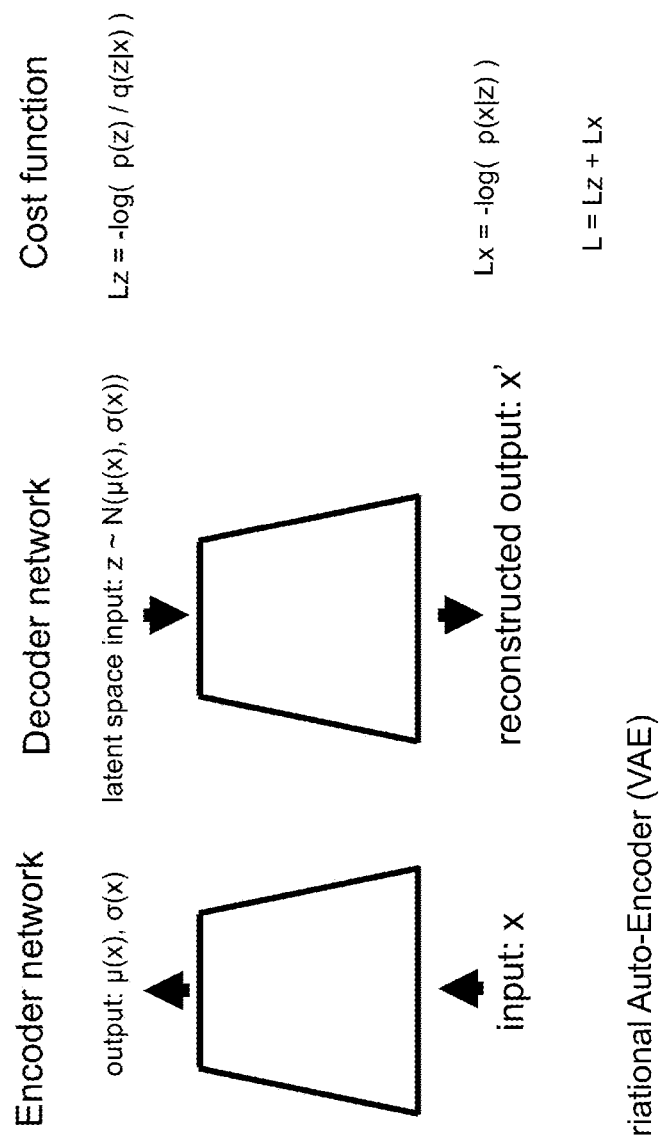
FIG. 51 schematically represents a variational auto-encoder.

In FIG. 51, we show the operation of a Variational Auto-Encoder (VAE): The standard VAE first encodes an input x into a set of latent variables $\mu(x)$, $\sigma(x)$. The decoder network samples the latent space from a prior distribution p(z), usually a Gaussian, and decodes to an output x'. The network is optimised to reproduce the inputs x maximally well, given a small latent space z. Thus the difference between x and x' has to be minimised, as does the amount of information passing through the latent layer. This is encapsulated by minimising the cost function L. A tensorial VAE allows for the inputs, the networks themselves, and the latent space to either include tensor network components, or be fully constructed using tensor networks.

We will now formally re-state the high-level concepts underlying the GTN system that have been discussed in this specification, as well as a large number of implementation features. Note that any high-level concept may be combined with any other high level concept and any one or more features.

Concept A

Providing a tensor network representation of molecular quantum states of small drug-like molecules as an input to a machine learning system, e.g. a neural network system.

Concept B

Providing a tensor network representation of molecular quantum states of small drug-like molecules as an input to a machine learning system, e.g. a neural network system, where the machine learning system is itself configured as a tensor network or includes tensor decompositions in its components.

Concept C

Creating a training dataset for a machine learning system, where the training dataset is a tensor network representation of the molecular quantum states of small drug-like molecules.

Concept D

A machine learning system, e.g. a neural network system, that takes as its input, tensor network representations of the molecular quantum states of small drug-like molecules and provides, as its output, tensor network representations of the molecular quantum states of small drug-like molecules to a predictive model that screens the output from the machine learning system.

Concept E

A machine learning based process for identifying small drug-like molecules including the following steps:
- (i) using tensor networks to efficiently represent a set of molecular quantum states of small drug-like molecules;
- (ii) providing that tensor network representation as an input to a machine learning system, e.g. a neural network system;
- (ii) the machine learning system efficiently searching through, sampling or otherwise analyzing this tensor network representation to identify candidate small drug-like molecules with required properties (e.g. prediction of binding to a target protein).

Subsidiary Features for Concepts A-E

Tensor Networks

- the tensor networks contain direct information about quantum correlations and entanglement properties
- the tensor network representations include one or more of: matrix product state (MPS), multi-scale entanglement renormalization Ansatz (MERA), and projected entangled-pair states (PEPS), correlator product states, tree tensor networks, complete graph network states, tensor network states.
- the tensor network representations include networks describing states with volume law entanglement, which can, for example, provide descriptions of highly excited states present in transition states of small molecules in a reaction or a binding process. It also allows for tensor networks describing density matrices—both those that obey the area law, and those that do not, and arbitrary superpositions of tensor networks, containing elements in general from distinct types of architectures (e.g. a superposition of two MPS tensor networks with a MERA network).
- the tensor networks efficiently represent a set of molecular quantum states of small drug-like molecules
- the set of molecular quantum states of small drug-like molecules is an exponentially large search space, e.g. a part or a significant part of the $10^{60}$ small drug-like molecules.
- A feature map is applied to input data to transform that input into a high dimensional tensor network structure
- A graph feature map is applied to input data to transform that input into a high dimensional tensor network structure
- featurization of graph models is by introducing entanglement features or other quantum mechanically features, derived from approximate molecular wave functions (e.g. from their tensor network descriptions, as obtained by minimising the tensor network components with respect to energy).

Training Datasets the tensor network representations are or include a training data set of small drug-like molecules the tensor network represents a set of simple descriptions of a molecule, so that a large set of molecules=1 tensor network the training dataset is tensor network representation of the molecular quantum states of small drug-like molecules the tensor network representations include a training data set of small drug-like molecules and a target, in which the small drug-like molecules are known to bind to the target.

the training dataset is tensor network representation of the molecular quantum states of small drug-like molecules and also a tensor network representation of the molecular quantum states of one or more targets, e.g. a protein to which a drug-like molecule may potentially bind, the protein binding pocket, or the description of the protein and small molecule as one large graph or tensor network.

the training dataset is used to train a generative model.

the training dataset is used to train a predictive model.

the predictive model is configured to predict whether a candidate small drug-like molecule is appropriate to a specific requirement The specific requirement is guided in terms of similarity to a particular molecule, using standard chemistry comparison methods, e.g. Tanimoto similarity, or using the latent space of a trained model, similarity measures between tensor network descriptions of the outputs (e.g. norm of the overlap between the candidate and target molecules).

the predictive model is configured to guide the generative model in determining whether a candidate small drug-like molecule is appropriate to a specific requirement a specific requirement is the capacity of a small drug-like molecule to bind to a target protein a specific requirement is one or more of the following: absorption; distribution; metabolism; toxicity, solubility, melting point, log(P).

a specific requirement is another biological process, such as an output of an assay designed to capture a specific phenotype. As an example, eczema results from continuous and unresolved inflammatory responses mediated by cytokines, leading to skin irritation and inflammation. The inflammation can be observed at the molecular level by the overexpression of CCL5, and a machine learning model can be trained to predict results of the assay.

The training dataset is used to train a generative model, which in turn feeds the predictive model The training dataset is fed high-quality molecules by a predictive model predictive model is a feed-forward system

Machine Learning the machine learning system is configured to handle tensor network inputs the machine learning system is configured to handle tensor network inputs by applying (tensorial) layers to the input, and using a mechanism to decrease the complexity of the resulting tensor network, so that it can be feasibly run on classical computers. For example, if the input network is a matrix product state (MPS), and the machine learning network consists of N applications of a matrix product operator (MPO), the bond dimension of the resulting MPS that needs to be stored in intermediate points in the calculation grows exponentially with N. A method to reduce the bond dimension (using e.g. standard DMRG SVD style projections), needs to be introduced to keep the calculation feasible on classical computers.

the machine learning system has been trained on a training dataset the machine learning system is supervised, semi-supervised or unsupervised machine learning system is a generative network, or an autoencoder, or RNN, or Monte-Carlo tree search model, or an Ising model or a restricted Boltzmann machine trained in an unsupervised manner.

machine learning system is a generative adversarial network the generative adversarial network is configured to receive a training dataset and to train (a) a generative model G that captures the training dataset distribution and (b) a discriminative model D that estimates the probability that a sample came from the training dataset rather than G.

machine learning system is a neural network that comprises tensorial decompositions or tensor networks.

machine learning system is a neural network constructed as a tensor network.

machine learning system is a quantum computer with quantum circuits configured as a tensor networks machine learning system is a quantum machine learning circuit (optionally based on a tensor network, and obtained by embedding the tensors in the networks into unitary gates). Such a circuit could take a machine learning computation that is classically not feasible, such as the MPO example above without SVD projections, and run it efficiently.

Predictive Model the machine learning system outputs tensor network representations of the molecular quantum states of small drug-like molecules to a predictive model the predictive model screens the output from the machine learning system.

the predictive model screens the output from the machine learning system by assessing the capacity of each sampled molecule to meet a specific requirement the predictive model is a feed-forward system that adds high-quality molecules to a source training dataset.

The predictive model is based on graph input data, or on graph input data enhanced by quantum features (as described in Appendix 3).

Concept F

A method of analysing a chemical compound dataset so as to determine suitable chemical compounds, the method comprising:
(i) determining a tensorial space for said chemical compounds dataset;
(ii) correlating the tensorial space with a latent space (and which may itself have a tensorial description); and
(iii) outputting a further dataset of candidate chemical compounds.

A system for analysing a chemical compound dataset so as to determine suitable candidate chemical compounds, the system comprising:
- (i) means for receiving a chemical compound dataset;
- (ii) a processor for processing the chemical compound dataset to determine a tensorial space for said chemical compound dataset;
- (iii) a processor for correlating said tensorial space with a latent space; and
- (iv) means for outputting a further dataset of candidate chemical compounds A method of analysing a chemical compound dataset so as to determine suitable chemical compounds, the method comprising:
- (i) generate tensor networks for a dataset of small drug like molecules, or other chemical compounds;
- (ii) correlate the tensor network description of chemical compounds, with machine learning models, where the machine learning models may themselves contain tensor network components, or be tensor networks in their entirety;
- (iii) in the context of generative models, correlate the inputs and models with a latent space or weight objects of a variational autoencoder model, or in the context of other generative models (such as GANs or other sequential latent space models such as GCPN; see Appendix 6, correlate the inputs with weights or latent space of the model. The latent space is usually a small vector space, and weight objects are matrices, but both may have a more general tensor network structure;
- (iv) output a further dataset of candidate small drug like molecules, or other chemical compounds, via generative models.
- (v) use a combination of tensorial predictive and generative molecules to guide the search through the space of small chemical compounds.

Subsidiary Features for Concept F the tensorial space is a wave function space.
latent space represents physically relevant wave functions.
latent space represents physically relevant wave functions in conjunction with a decoder network.
the further dataset of candidate chemical compounds is a filtered dataset of candidate chemical compounds.
the further dataset of candidate chemical compounds is a novel dataset of candidate chemical compounds.
Wave functions describing elements in some (e.g. molecular) datasets are each represented by an appropriate tensor network. A whole set of wave functions could be described by an appropriate tensor network as well.
the tensor network is one of: complete-graph tensor network state, correlator product state, projected entanglement pair states (PEPS), matrix product states (MPS)/tensor train, tree tensor network, and matrix product operator.
the dataset is mapped into a higher dimensional tensor.
the correlating process includes optimising over the latent space.
the correlating process includes determining an optimal tensor network to describe the mapping of the input data set to a more general description
the latent space represents desired properties of a set of candidate chemical compounds.
the correlating process includes maximising a cost function, said cost function representing desirable properties of the candidate chemical compounds.
determining the tensorial space for the chemical compounds dataset comprises encoding said dataset using a generative model.
The outputting process includes the process of decoding using a generative model.
the generative model comprises a neural network.
the generative model comprises a graph variational auto encoder or graph based GAN, with enhanced featurisation based on separate quantum mechanical calculations (perhaps done using tensor network methods, or other quantum chemistry methods).
the neural network is in the form of an autoencoder.
the autoencoder is a variational autoencoder.
the neural network is any of the following: generative auto encoder, RNN, GAN, Monte-Carlo tree search model, an Ising model or a restricted Boltzmann machine trained in an unsupervised manner etc. (see openreview.net/pdf?id=Bk0xiI1Dz, arxiv.org/abs/1710.07831, and references therein]
the neural network comprises tensorial decompositions or tensor networks, or is constructed as a tensor network in its entirety.
the tensor network comprises a tensorial generative autoencoder.
A visualisation of the tensorial space is generated and output.
candidate chemical compounds are active elements of a pharmaceutical compound.
candidate chemical compounds are suitable for use in an organic light emitting diode.
The chemical compound dataset is a dataset of possible molecules containing up to a predetermined maximum number of atoms.

System

A system configured to perform any of the preceding methods.

Molecules

A molecule or class of molecules identified using any of the above processes or systems.

Some Formal Points on the Scope of the Invention

The invention extends to methods, system and apparatus substantially as herein described and/or as illustrated with reference to the accompanying figures. The invention also provides a computer program or a computer program product for carrying out any of the methods described herein, and/or for embodying any of the apparatus or system features described herein, and a computer readable medium having stored thereon a program for carrying out any of the methods described herein and/or for embodying any of the apparatus features described herein. The invention also provides a signal embodying a computer program or a computer program product for carrying out any of the methods described herein, and/or for embodying any of the apparatus features described herein, a method of transmitting such a signal, and a computer product having an operating system which supports a computer program for carrying out the methods described herein and/or for embodying any of the apparatus features described herein.

Any feature in one aspect of the invention may be applied to other aspects of the invention, in any appropriate combination. In particular, method aspects may be applied to apparatus aspects, and vice versa. As used herein, means plus function features may be expressed alternatively in terms of their corresponding structure, such as a suitably programmed processor and associated memory. Furthermore, features implanted in hardware may generally be implemented in software, and vice versa. Any reference to software and hardware features herein should be construed accordingly. It will be appreciated that although the present invention has been described principally in the field of filtering molecule datasets for drug development (and the like), the described methods may also be used in any field in which a large, multi-dimensional search space exists. It will be understood that the invention has been described above purely by way of example, and modifications of detail can be made within the scope of the invention. Each feature disclosed in the description, and (where appropriate) the claims and drawings may be provided independently or in any appropriate combination. Reference numerals appearing in the claims are by way of illustration only and shall have no limiting effect on the scope of the claims. Inclusion of a reference or citation in this specification is neither acceptance nor implication that it is valid or relevant prior art; for example, in light of the fast moving field of this invention, references have been included in this specification that post-date the priority date, but precede its filing date, and these references should be assumed to be non-citable prior art.

APPENDIX 3

Primer on Graph Featurization and Tensor Networks

This Appendix 3 contain background, ideas, details, and preliminary results on how we go about adding physically-inspired entanglement features to the GTN system's machine learning graph models using well-established quantum chemistry methods and tensor network algorithms.

1. High Level Overview

According to some, the holy grail of rational drug design would be the advent of large scale quantum computers capable of aiding and guiding scientists at every step in the drug discovery process. These devices would exploit our understanding of quantum mechanics to directly simulate nature. Since quantum computing in its current form is very much a toy project in its infancy, decades away from any applications, one feels obliged to come up with other strategies in the meantime.

One such strategy involves combining machine learning algorithms with computational chemistry, leveraging recent advances in computational infrastructure. Let us focus on ligand-based drug design for now since structure-based drug design comes with its additional set of complications, assumptions, and approximations. Ideally, from a physics perspective, one would like to feed the molecule's wave function (or its tensor network representation) as input to a machine learning (ML) pipeline. The intuitive reason for this is that you want to make the algorithm focus on calculating properties and not on finding the ground state by already providing it with the wave function as input data. Not doing so arguably makes the learning much harder, since, by refusing to input anything interesting on the structure of the wave function, machine learning algorithms can get confused when trying to build a statistical model of the data. Given oversimplified proxies of the wave function like fingerprints and SMILES strings, the model has to learn how to run (what is measurable property X calculated from the wave function?) before it can even walk (what is a wave function?). One can argue that it is naive to think that a ML algorithm implicitly has to first solve the Schrödinger equation and calculate the ground state before calculating properties like humans do, but it is equally questionable to assume that it finds a set of magical weights which bypass quantum mechanics altogether. Machine learning is far from a black box and it is advisable to find a delicate balance between letting the algorithm figure out things on its own and steering the learning process.

Since inputting the full wave function (or its tensor network representation) is intractable at the moment, one can input SMILES or graphs or other proxies for the wave function data, together with a list of observed or measured global properties of the molecule. But there's more to chemistry than SMILES strings and atom connectivity. In the short-term, the idea would be to improve the ad hoc featurization of graph models by introducing features derived from approximate molecular wave functions, supplying fine-grained information about the underlying chemistry/physics. The expectation is that this should lead to stronger learning capabilities, better generalization, and improved latent representations without overfitting, which is important for both predictive and generative models. Starting from a molecule's composition, ab initio quantum chemistry methods try to approximate the molecular wave function in some appropriately chosen orbital basis set. The properties/features we extract from these methods should in some sense be raw, i.e. independent of the method or basis used and as close as possible to the wave function data. It is important to stress that our goal is not to obtain the best possible ground state energies for every particular conformation of the molecules in a dataset. That would be silly and also quite impossible for the sizes of the datasets we are interested in. We need something quick and reasonably accurate to deduce qualitatively correct information about the electronic correlations, under the implicit assumption that any information on quantum correlations and actual chemistry will be better than just inputting SMILES.

2. Quantum Chemistry 101 (for Physicists)

We will focus on ab initio quantum chemistry methods for the electronic structure of small molecules within the Born-Oppenheimer approximation of the time-independent non-relativistic quantum many-body Schrodinger equation.

$$H(R,r)\Psi(R,r)=E(R)\Psi(R,r), \quad (1)$$

with the molecular Hamiltonian $$H(R, r) = -\frac{1}{2}\sum_{i=1}^{N} \nabla_i^2 - \frac{1}{2}\sum_{A=1}^{M} \frac{1}{M_A}\nabla_A^2 - \sum_{i=1}^{N}\sum_{A=1}^{M} \frac{Z_A}{r_{iA}} + \sum_{i=1}^{N}\sum_{j>i}^{N} \frac{1}{r_{ij}} + \sum_{A=1}^{M}\sum_{B>A}^{M} \frac{Z_A Z_B}{R_{AB}}, \quad (2)$$

where $Z_A$, $M_A$, M, and N denote respectively nuclear charges, nuclear masses relative to the electron's mass, the number of nuclei, and the number of electrons. The electronic part of the Schrödinger equation looks like $$H_{elec}(R, r)\chi(R, r) = E_{elec}(R)\chi(R, r) \quad (3)$$

where $$H_{elec}(R, r) = -\frac{1}{2}\sum_{i=1}^{N}\nabla_i^2 - \sum_{i=1}^{N}\sum_{A=1}^{M}\frac{Z_A}{r_{iA}} + \sum_{i=1}^{N}\sum_{j>i}^{N}\frac{1}{r_{ij}}, \quad (4)$$

so that the total energy is simply $$E_{tot} = E_{elec} + E_{nucl}$$

FIG. 52 reproduces equations (1) to (4).

In practice, one uses a finite set of basis functions to turn the above partial differential equations into algebraic equations amenable to numerical simulation. In electronic structure calculations for condensed-matter physics plane waves are natural whereas in quantum chemistry people are fond of atomic orbitals. Note that basis functions are most often not true atomic orbitals, apart from hydrogen and other one-electron systems. It is important to remember that orbitals, like anything in physics, are just mathematical constructs which approximate reality. Common basis sets are Gaussian-type orbitals, Slater-type orbitals, or other numerically obtained orbitals. While atomic orbitals contain the electrons of a single atom, molecular orbitals, which surround a number of atoms in a molecule, are said to describe valence electrons shared between atoms. To understand bonding, molecular orbital theory thus approximates the molecular orbitals (which, essentially, correspond to delocalized electrons) as linear combinations of atomic orbitals (LCAO).

2.1 Hartree-Fock Method

The Hartree-Fock (HF) method is a variational procedure which approximates energy eigenfunctions of the electronic Schrödinger equation (3) by a single Slater determinant, i.e. an anti-symmetrized product of one-electron wave functions (orbitals), $$\Psi(x_1, x_2, \ldots, x_N) = \frac{1}{\sqrt{N!}}\begin{vmatrix} \chi_1(x_1) & \chi_2(x_1) & \cdots & \chi_N(x_1) \\ \chi_1(x_2) & \chi_2(x_2) & \cdots & \chi_N(x_2) \\ \vdots & \vdots & \ddots & \vdots \\ \chi_1(x_N) & \chi_2(x_N) & \cdots & \chi_N(x_N) \end{vmatrix} \quad (5)$$

$$= |\chi_1, \chi_2, \ldots, \chi_N\rangle, \quad (6)$$

where the $$\chi_i(x), \forall i \in \{1, 2, \ldots N\}$$

are a set of one-electron spin-orbital wave functions. FIG. 53 reproduces equations (5) to (6). These are products of a spatial orbital $\psi_i(r)$ and a spin function $\alpha$ or $\beta$. Note that each electron is actually associated with every orbital (the electrons are indistinguishable) and that the number of electrons N is taken to be equal to the number of orbitals L.

The Fermi correlation due to electron exchange (Pauli exclusion principle) is accounted for via the explicit anti-symmetrization. Electrons move independently within molecular orbitals, each of which describes the probability distribution of a single electron. On top of that, the HF approximation also resorts to a mean-field treatment of the interactions among electrons, neglecting the instantaneous electron-electron correlations. Every electron only feels an average contribution of all other electrons.

2.1.1 Self-Consistent Field Algorithm

The starting point of HF calculations is the molecular geometry (3D coordinates) and a finite set of approximate one-electron wave functions (spin-orbitals). For a molecular orbital calculation, the initial one-electron wave functions are typically already a linear combination of atomic orbitals (LCAO). One obtains the optimum set of molecular orbitals by variationally minimizing the energy in what is called a "self-consistent field" or SCF approximation to the many-electron problem. Given a set of molecular orbitals, the energy expectation value is minimized by solving one-particle eigenvalue equations (Hartree-Fock-Roothan generalized eigenvalue equations) for the molecular orbitals. These new eigenfunctions can then be used to recalculate the average field felt by each electron, after which the procedure is repeated until the set of molecular orbitals converges to the so-called Hartree-Fock molecular orbitals.

In practice, there's a number of methods. Restricted Hartree-Fock (RHF) is used for closed-shell molecules at their equilibrium geometry, where electrons occupy orbitals in pairs. Restricted open-shell Hartree-Fock (ROHF) is used for open-shell molecules where the spin parts $\alpha$ and $\beta$ of the orbitals are constrained to be identical, leading to proper eigenfunctions of the total spin operator but lacking a unique set of molecular orbitals since the form of the Fock matrix is often not unique. Unrestricted Hartree-Fock (UHF) is used for open-shell molecules and uses different molecular orbitals for the $\alpha$ and $\beta$ electrons, leading a ground state which can be contaminated by excited states since spin is not conserved.

2.1.2 Hartree-Fock Wave Functions and Entanglement

Since the HF algorithm is variational, the HF energy is an upper bound to the true ground state energy of a given molecule, corresponding to the minimal energy for a single Slater determinant. The best possible solution is called the HF limit, where the basis set approaches completeness. On the other hand, dropping the HF approximations of a single Slater determinant and mean-field interactions, we arrive at the full-CI (configuration interaction) limit, which corresponds to the exact solution up to the Born-Oppenheimer approximation. The energy difference between the HF solution and the exact ground state is sometimes called the electron correlation energy. The exact ground state corresponding to the full-CI limit will be important to connect quantum chemistry methods to tensor networks (see Section 3.2 below).

In physics, we would call the wave function obtained from Hartree-Fock a mean-field solution, or a product state, or quite simply a boring state without any entanglement. The probability $P(r_1, r_2)$ of finding an electron at $r_1$ and $r_2$ is not simply $p(r_1)p(r_2)$. To deal with this weakness, a lot of post-Hartree-Fock methods have been devised, correcting for the neglected electron-electron correlation in different ways. Still, because HF is so cheap and often qualitatively correct, many types of calculations are initialized with a HF calculation.

2.2 Post-Hartree-Fock Methods

In general, the exact ground state wave function of the electronic Hamiltonian Equation (4) entails a superposition of all possible distributions of N electrons over L orbitals, i.e. a linear combination over all possible Slater determinants, which blows up factorially. In this sense, HF boils down to the simplest possible approximation by picking only a single Slater determinant. The occupancy of the HF orbitals is fixed: occupied orbitals are filled with probability 1 and virtual orbitals are empty with probability 1. Post-Hartree-Fock methods improve upon the HF-SCF method by adding the effects of electron correlation, which HF completely neglects apart from the exchange energy resulting from the explicit anti-symmetrization of the wave function. Note that there are many more post-Hartree-Fock methods than the ones we will mention below, including subtle variations and combinations with other methods.

2.2.1 Intuition

In second quantization (Fock space), orbitals are either doubly, singly, or unoccupied by an electron. We can conceptually regard Hartree-Fock with mostly paired electrons as optimizing occupied (lower 4 lines—red) and virtual (upper 4 lines—blue) orbital spaces such that the energy expectation value is minimized (also shown in FIG. 54):

$$|\Psi_{HF}\rangle = \begin{array}{c} \underline{\phantom{xx}} \\ \underline{\phantom{xx}} \\ \underline{\phantom{xx}} \\ \underline{\phantom{xx}} \\ \underline{\uparrow \downarrow} \\ \underline{\uparrow \downarrow} \\ \underline{\uparrow \downarrow} \\ \underline{\uparrow \downarrow} \end{array} \quad (7)$$

The configuration interaction (CI) method is a post-Hartree-Fock variational method which accounts for electron correlation by using a variational wave function that is a linear combination of configuration state functions (CSFs) built from spin orbitals. A configuration state function is a symmetry-adapted linear combination of Slater determinants.

$$|\Psi_{CI}\rangle = C_0 \begin{array}{c}\underline{\phantom{xx}}\\\underline{\phantom{xx}}\\\underline{\phantom{xx}}\\\underline{\uparrow\downarrow}\\\underline{\uparrow\downarrow}\\\underline{\uparrow\downarrow}\\\underline{\uparrow\downarrow}\end{array} + \sum_{ia} C_i^a \begin{array}{c}\underline{\phantom{xx}}\\\underline{\phantom{xx}}\\\underline{\uparrow a}\\\underline{\uparrow\downarrow}\\\underline{\uparrow i}\\\underline{\uparrow\downarrow}\\\underline{\uparrow\downarrow}\end{array} + \sum_{ijab} C_{ij}^{ab} \begin{array}{c}\underline{\uparrow b}\\\underline{\phantom{xx}}\\\underline{\downarrow a}\\\underline{\uparrow\downarrow}\\\underline{\uparrow i}\\\underline{\uparrow\downarrow}\\\underline{\downarrow j}\end{array} + \dots \quad (8)$$

or $$|\Psi_{CI}\rangle = (1 + T_1 + T_2 + \dots)|\Psi_{HF}\rangle. \quad (9)$$

Figures 54, 55:
FIG. 54 schematically represents paired electrons as optimizing occupied orbital spaces, referenced as (7) in the Appendix 3.
FIG. 55 schematically represents configuration interaction, referenced as (8) and (9) in Appendix 3.

FIG. 55 reproduces (8) to (9). The first term in the expansion is usually the HF determinant $|\Psi_{HF}\rangle$ and this reference state is assumed to be qualitatively correct and dominant. If the expansion includes all possible CSFs of the appropriate symmetry by exciting all possible electrons to all possible virtual orbitals, then this is a full configuration interaction procedure which exactly solves the electronic Schrodinger equation within the space spanned by the one-particle basis set. Usually though, the series is truncated to single and double excitations, leading to problems with size-consistency. Other methods like coupled cluster (CC) use an exponential trial wave function $|\Psi_{CC}\rangle = e^{T_1+T_2+\dots}|\Psi_{HF}\rangle$ as an Ansatz, which is size-consistent. On the other hand, coupled cluster is not variational since the normalisation of the wave function cannot be enforced. In practice that doesn't really matter though, since, for properties such as energy, it is known how to truncate the Ansatz when examining expectation values (but not for the wave function itself!). The gold standard of quantum chemistry is often said to be CCSD(T), i.e. coupled cluster which includes singles, doubles, and perturbative triples corrections. Recent advances to improve computational costs of CCSD(T) and to counter the requirements for large basis sets have led to the development of DLPNO-CCSD(T) methods which exploit locality of correlations using strong pair approximations and pair natural orbitals.

For nearly degenerate states contributing to the ground state Eq. 8 one should use multi-configurational self-consistent field (MC-SCF) methods (see Section 2.2.3). In that case, the Hartree-Fock determinant reference state is qualitatively wrong, since the weight $|C_0|$ is not dominant, and so are the resulting CI wave functions and energies. This can happen when the ground state is strongly-correlated and static correlations have to be taken into account.

2.2.2 Static and Dynamic Correlations

Electron correlations are often rather artificially divided into two contributions: static and dynamic correlations. The former corresponds to configurations which are nearly degenerate with respect to the reference Slater determinant, while the latter arises from the need of mixing the Hartree-Fock state with a bunch of higher-order excited states. In systems with (strong) static correlation the wave function is said to differ qualitatively from the reference Slater determinant, while strong dynamic correlation implies a wave function which includes a large number of excited determinants, all with comparable, small occupations. An example of a method that recovers primarily dynamic correlation is Møller-Plesset perturbation theory (MPn), while multi-configurational self-consistent field (MC-SCF) methods primarily take care of static correlations. It is almost impossible to keep dynamic and static correlation effects separated since, from a physical point of view, they both arise from the very same interaction.

Dynamic correlation can also be captured with ab initio post-Hartree-Fock methods. These start from the optimized HF orbitals and the corresponding Slater determinant and build in dynamic correlation on top of that single reference state. Examples include the aforementioned MPn perturbation theory, the configuration interaction (CI) expansion, and coupled cluster (CC) theory. Because these post-Hartree-Fock methods start from a single Slater determinant reference, they have difficulty building in static correlation. It is therefore better to resort to multi-configurational self-consistent field (MC-SCF) methods for systems with pronounced static correlation, e.g. for molecular ground states which are quasi-degenerate with low-lying excited states or in bond breaking situations.

2.2.3 Multi-Configurational Methods

Figure 56:
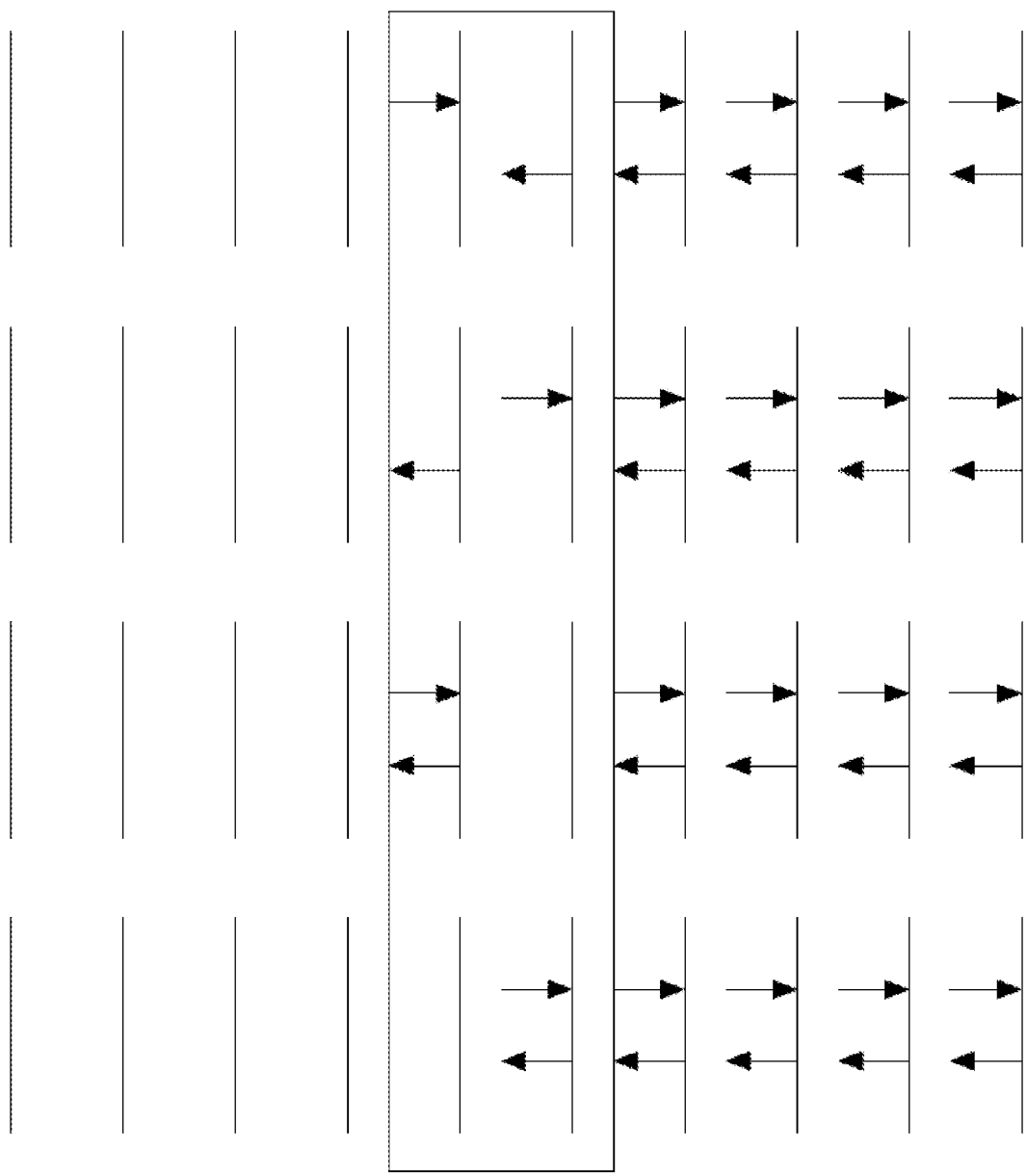
FIG. 56 schematically represents occupied, active and virtual orbitals.

Multi-configurational self-consistent field (MC-SCF) methods come into play when a single electron configuration does no longer provide an adequate description of the electronic structure. An important MC-SCF approach is the complete active space SCF (CAS-SCF) method which can be used to obtain an approximation of the static correlation. In this framework, orbitals can be classified as either occupied (always containing two electrons), active (partially occupied and relevant for the chemistry), and virtual (always empty). Intuitively, this is shown in FIG. 56.

From a HF solution, a subset of occupied and virtual orbitals is selected to act as active space. The remaining occupied and virtual orbitals are kept frozen at HF level and the electronic structure in the active space is solved for exactly. The notation CAS(N, L) refers to an active space containing N electrons distributed between all configurations that can be constructed from L molecular orbitals. A CAS-SCF simulation is a two-step process where the energy can be iteratively minimized by doing a full-CI calculation only in the active space (CAS-CI). That information is then used to rotate the occupied and active orbital spaces to minimize the energy even further. Because the many-body Hilbert space grows exponentially with the number of single-particle states, only small active spaces up to 18 electrons in 18 orbitals can be treated with CAS-CI (cf. exact diagonalization). Dynamic correlation is usually small and can be recovered with good accuracy by means of perturbative methods on top of the CAS solution which should contain the proper static correlation.

2.3 Remarks for Confused Physicists

2.3.1 Density Matrices

Density matrices are fundamental objects in quantum mechanics. To avoid confusion with the notion of a density matrix as used by physicists, let us explicitly state what is meant by the term in quantum chemistry and electronic structure calculations. In particular, the N-particle density matrix refers to:

$$\rho = |\Psi(x_1, x_2, \ldots, x_N)\rangle\langle\Psi(x_1, x_2, \ldots, x_N)|, \quad (10)$$

which specifies everything there is to know about the wave function of the system since it gives the probability of the state with a given set of coordinates xi (space and spin) for all electrons in the system. Since most physical operators are not N-electron operators (e.g. the kinetic energy operator is a one-electron operator and the Coulomb interaction is a two-electron operator), we do not require the full N-particle density matrix to calculate energies and local properties. If we trace out all coordinates except for x1, we arrive at the one-particle reduced density matrix (1PDM, ODM, 1RDM, ... )

$$\rho^{(1)}(x_1, x'_1) = N \int \Psi^*(x'_1, x_2, \ldots, x_N) \Psi(x_1, x_2, \ldots, x_N) dx_2 \ldots dx_N, \quad (11)$$

which is a generalization of the one-electron density $$\rho^{(1)}(x_1) = N \int \Psi^*(x_1, x_2, \ldots, x_N) \Psi(x_1, x_2, \ldots, x_N) dx_2 \ldots dx_N. \quad (12)$$

Integrating the one-electron density over the spin of the first electron yields the following spin-free first-order reduced density matrix, $$P^{(1)}(r_1) = \int \rho^{(1)}(r_1; s_1) ds_1. \quad (13)$$

Similarly, we can also define a two-particle reduced density matrix $$\rho^{(2)}(x_1, x_2; x'_1, x'_2) = N(N-1) \int \Psi^*(x'_1, x'_2, \ldots, x_N) \Psi(x_1, x_2, \ldots, x_N) dx_3 \ldots dx_N, \quad (14)$$

which is a generalization of the two-electron density $$\rho^{(2)}(x_1, x_2) = N(N-1) \int \Psi^*(x_1, x_2, \ldots, x_N) \Psi(x_1, x_2, \ldots, x_N) dx_3 \ldots dx_N. \quad (15)$$

FIG. 57 reproduces equations (10) to (15). Determining the one- and two-particle RDMs is enough for the electronic structure problem. In the Hartree-Fock approximation, the one-particle RDM is enough since the two-particle, three-particle, ... density matrices can all be expressed in terms of direct products of the one-particle RDM. For correlated methods however, the $\rho^{(i)}$ density matrices have to be determined separately

2.3.2 Orbitals

The one-particle RDM Eq. (11) can be written in terms of a complete set of spin-orbitals $$\rho^{(1)}(x_1, x'_1) = \sum_{i,j} \rho^{(1)}_{ij} \phi_i(x_1) \phi_j^*(x'_1). \quad (16)$$

The diagonal elements $\rho^{(1)}$ are called orbital occupation numbers. Since a unitary transformation on the set of spin-orbitals leaves the wave function invariant, the matrix $\rho^{ij}$ can be transformed into diagonal form with diagonal elements $0 \leq n_i \leq 1$ corresponding to the occupation numbers of the natural spin-orbitals (NSOs), satisfying $$\Sigma_i n_i = N.$$

The one-particle RDM then becomes $$\rho^{(1)}(x_1, x'_1) = \sum_i n_i \phi_i^{NSO}(x_1) \phi_j^{*NSO}(x'_1). \quad (17)$$

Diagonalizing the spin-free first-order RDM yields so-called natural orbitals (NOs), which constitute an orthonormal set of eigenorbitals intrinsic to the N-electron wave function, $$P^{(1)}(r_1, r'_1) = \sum_i n_i \phi_i^{NO}(r_1) \phi_j^{*NO}(r'_1). \quad (18)$$

where now $0 \leq n_i \leq 2$.

FIG. 58 reproduces equations (16) to (18).

Molecular orbitals are completely fictitious constructs used to piece together a wave function of the molecule. As we have seen above, solving an energy eigenvalue equation using a set of basis orbitals (orthogonal or non-orthogonal) yields so-called canonical molecular orbitals (CMOs), which represent specific electrons and can generically be completely delocalized over the entire molecule. For our purposes, it may prove fruitful to consider localized molecular orbitals (LMOs), which are concentrated in a limited spatial region of a molecule and relate MO calculations back to theory of chemical bonding. These LMOs are obtained from a unitary transformation on a set of delocalized CMOs (a linear combination) by optimizing the expectation value of some operator. For closed-shell molecules, the localized and delocalized orbital descriptions are equivalent and represent the same physical state. Different prescriptions (Foster-Boys, Edmiston-Ruedenberg, Pipek-Mezey) optimize different quantities and can thus lead to different localized orbitals.

Another approach to localization of molecular orbitals is given by natural bond orbitals (NBOs) which represent electron density and stay closer to the intuitive picture of chemical bonding (on the other hand, NBOS can have any occupancy since this property is no longer well defined). These orbitals are constructed to have maximum electron density, corresponding to the best possible Lewis structure, and are part of a sequence of orbital sets related by similarity/unitary transformations (also shown in FIG. 58):

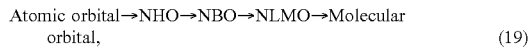

$$\text{Atomic orbital} \rightarrow \text{NHO} \rightarrow \text{NBO} \rightarrow \text{NLMO} \rightarrow \text{Molecular orbital}, \quad (19)$$

which includes natural atomic orbitals (NAO), natural hybrid orbitals (NHO), natural bonding orbitals (NBO) and natural (semi-)localized molecular orbitals (NLMO). These natural localized sets of orbitals are in between atomic orbitals and molecular orbitals. Natural atomic orbitals (NAOs) correspond to the effective natural orbitals of an atom in the molecular environment, with core and valence-shell NAOs having significant occupancies. Natural bond orbitals (NBOs) are optimized linear combinations of NAOs which attempt to give the best possible valence bond-type description of the wave function. They are said to be insensitive to variations of basis sets or approximation methods and to reflect the character of the wave function uniquely. Finally, the natural localized molecular orbitals (NLMOs) are LMOs which are obtained by optimizing for minimal delocalization of NBOs.

2.3.3 Wave Functions and Relaxed Density Matrices

For wave functions which are exact solutions of the Schrödinger equation, obtaining one-particle RDMs boils down to a pretty straightforward application of quantum mechanics.

But quantum chemistry uses incomplete basis sets and a whole host of approximations, invalidating this naive physicists' picture. Computational methods like HF, CI, MC-SCF, and QC-DMRG do have approximate wave functions associated to them in the sense that their expressions for the energy correspond to the expectation value of the Hamiltonian operator calculated using those approximate wave functions. The one particle RDM derived from these approximate wave function methods is well-defined and the expectation value of any one-electron property is simply the trace of the density matrix multiplied by the operator representing that property.

However, it is important to stress that other methods (DFT, MPn, and coupled cluster) do not have wave functions at all, not even approximate ones. What this means is that the approximate "wave function" simply does not exist (like in DFT where the quantity of interest is an effective density), or that the energy evaluated in these methods using the corresponding approximate "wave function" does not at all correspond to the expectation value of the Hamiltonian using this same "wave function" (MPn and CC methods). To appreciate this, let us define a response-type density matrix D, defined such that the derivative of the energy E with respect to any one-electron perturbation is xV is E'=Tr(DV); which leads to identical results for methods which optimize the energy with respect to molecular orbitals (HF, MC-SCF, full-CI). For approximate solutions (like CISD), they can differ and one can define both expectation value and response-type density matrices with different properties. Calculating quantities like dipole moments then gives two different answers for the two kinds of density matrices, namely the expectation value of the dipole operator and the derivative of the energy with respect to the applied electric field. The response-type density matrix is often called the relaxed density matrix and does not require a wave function to be defined. For methods without an approximate wave function, one can still construct approximations to the expectation value density matrix, which are then called unrelaxed densities.

3. Tensor Networks and Quantum Chemistry

Applying tensor network ideas to quantum chemistry has been initiated in the group of White [cite 3 Wouters 2014] and has been subsequently developed in the groups of Legeza, Chan, Reiher, and Van Neck during the past 15 years. For a more extensive overview of ab initio DMRG in quantum chemistry, we refer to the introductory chapters of the PhD dissertations of Sebastian Wouters [cite 4: Wouters 2014] and Johannes Hachmann [cite 5: Hachmann 2010].

3.1 What is a Tensor Network?

Tensor networks are entanglement-based ansätze for ground and excited states of quantum many-body systems. There exist lots of different tensor networks tailored to different kinds of entanglement structure, but they all boil down to the same idea: efficient ways of exploring the 'physical' part of an exponentially large many-body Hilbert space. The reason this even works at all can be understood in terms of entanglement area laws and the local nature of interactions. Put differently, a tremendous amount of information in the 'mathematical" exponential Hilbert space is completely redundant and superfluous if you are interested in 'physical' ground states and low-lying excited states of local Hamiltonians.

3.2 Matrix Product States: QC-DMRG

Figures 59, 60, 61:
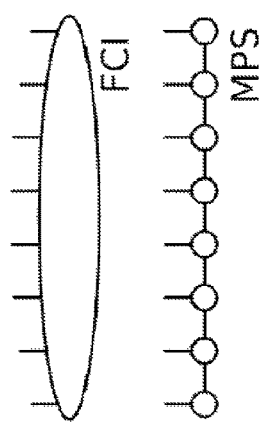
FIG. 59 shows equations (20) from Appendix 3.
FIG. 60 pictorially represents MPS tensors
FIG. 61 shows equations (11) from Appendix 3.

For our purposes, we will focus on matrix product states (MPS), which is the particular kind of linear Ansatz underlying the influential density matrix renormalization group (DMRG) algorithm. The quantum chemistry version of DMRG (QC-DMRG) naturally emerges when trying to construct a tensor decomposition of the full-CI wave function. Recall that in the CAS-SCF approach, we select an active space of N electrons in L orbitals, on which a full-CI expansion is applied [cite 6].

$$|\Psi_{CAS-CI}\rangle = \sum_{n_1,\ldots,n_L} C_{n_1,\ldots,n_L} |n_1 n_2 \ldots n_L\rangle, \quad (20)$$

where $|n_1 n_2 \ldots n_L\rangle$ is an occupation number vector (Fock space). FIG. 59 reproduces equation (20). This Ansatz scales exponentially since the calculations of the full-CI tensor is limited to CAS(18,18) spaces (cf.~exact diagonalization). By doing successive singular value decompositions (SVDs) on the rank-n tensor C, we arrive at an Ansatz in terms of local tensors. Pictorially, this is shown in FIG. 60 [cite 7].

This leads to an Ansatz for the wave function where the FCI tensor is rewritten as a contracted matrix product. Unlike most wave function methods in quantum chemistry, the MPS wave function is not parametrized by excitations from an underlying reference state but built directly from these local variational objects (tensors). Rather than truncating the number of excitations on top of some single reference state, QC-DMRG truncates in a virtual space of bond dimension D (the horizontal legs) containing entanglement degrees of freedom with no preferences towards any particular state, which makes it a natural candidate to study multi-configurational systems where static correlations are important. The error in the MPS wave function can be quantified by the truncation error $$\epsilon = \|\|\Psi\rangle - |\tilde{\Psi}\rangle\|^2 = 1 - \sum_{\alpha=1}^{D} \omega_\alpha, \qquad (21)$$

where the target wave function $|\Psi\rangle$ is approximated by $|\tilde{\Psi}\rangle$ and the $w_\alpha$ are the eigenvalues of the local reduced density matrix which you throw away. FIG. 61 reproduces equation (21). The DMRG is an iterative algorithm which optimizes over MPS wave functions to converge to the exact solution of the electronic Schrodinger equation in a given active orbital space with polynomial rather than exponential cost. Unlike traditional CAS-based approaches, DMRG is a local multi-configurational approach which, thanks to its polynomial scaling, can deal with active spaces comprising up to 50 orbitals. In terms of the number of orbitals L (corresponding to the number of lattice sites) and the bond dimension D, the QC-DMRG algorithm has an overall scaling per sweep of $\mathcal{O}(L^4D^2+L^3D^3)$ in CPU time, $\mathcal{O}(L^2D^2)$ in memory, and $\mathcal{O}(L^3D^2)$ in disk.

The correlations among the orbitals are characterized by the bond dimension D which sets the number of variational parameters (for D→∞, the wave function would become exact for a given active space). The one-dimensional nature of the Ansatz suggests that it is important to order orbitals along the chain such that strongly-correlated ones are close to each other (otherwise, correlations would have to travel "through" many sites of the chain to communicate). The QC-DMRG algorithm has been combined with CAS-SCF methods to optimize the orbitals themselves, using the QC-DMRG method as an approximate solver in the active space instead of CI. Dynamical correlations can be added on top of the MPS reference wave function by resorting to N-electron valence perturbation theory to second-order (NEVPT2) and complete-active space perturbation theory to second order (CASPT2) [Cite 6: Knecht 2015].

Recent applications of QC-DMRG are listed in the review article [Cite 7: Wouters 2014a]. For more details, we recommend the very same review article [cite 7: Wouters 2014a] by Sebastian Wouters since he uses modern MPS notation rather than old-fashioned DMRG-block style notation. Other reviews are included in the references [Cite 6: Chan 2008; Cites 8-10: Chan 2011, Olivares-Amaya 2015, Knecht 2015] and another extensive list of references can be found at quattro.phys.sci.kobe-u.ac.jp/dmrg/prop4.pdf. A great introductory talk is the one by Chan [Cite 11: Chan2015].

3.3 Software Packages for QC-DMRG

Since it takes an entire PhD to develop a decent QC-DMRG code which implements symmetries and supports parallelization through OpenMP and MPI, we should use an already developed package. Considering freely available packages: There's QuMaquis by the Eihert group but the code is stored on a private repository which you have to request access to. There's Block by the Chan group and CheMPS2 by Sebastian Wouters, both of which are written in C++ with Python wrappers.

3.4 Entanglement Measures

One reason to try QC-DMRG is that the one-orbital von Neumann entropy $$S_i = -\sum_{\alpha=1}^{4} \omega_{\alpha,i} \ln \omega_{\alpha,i}, \qquad (22)$$

the two-orbital von Neumann entropy $$S_{ij} = -\sum_{\alpha=1}^{16} \omega_{\alpha,ij} \ln \omega_{\alpha,ij}, \qquad (23)$$

and the mutual information between a pair of orbitals $$I_{ij} = \tfrac{1}{2}(S_i + S_j - S_{ij})(1 - \delta_{ij}) \qquad (24)$$

can be calculated in a straightforward way from the tensor network representation of the molecular wave function in orbital space (see also Question 1 below). FIG. 62 reproduces equations (22) to (24). These bipartite entanglement measures reveal a lot about the correlations in the quantum state. In particular, calculating these quantities using QC-DMRG, for a given choice of orbitals and orbital order, leads to complex diagrams where the linear, one-dimensional MPS chain has been plotted as a circle. Every dot in corresponds to an style of the lines connecting the orbitals denote the value of the mutual information for those two orbitals.

Note that a correlated wavefunction is required to have non-zero orbital entanglement and correlation. In the case of an uncorrelated wavefunction (for instance, a single Slater determinant) the (orbital) entanglement entropy is zero.

Stein and Reiher have proposed to use these measures to automate the selection of active orbital spaces in CAS-DMRG by exploiting the capability of QC-DMRG to include up to about one hundred orbitals in the active space to systematically assess and select active orbitals [Cite 16: Stein 2016].

3.5 Other QC-TNS Ansätze

Apart from the linear matrix product state (MPS) Ansatz, people have also considered using tree tensor networks (TNS) [Cites 12-14: Nakatani 2013, Murg 2015, Gunst 2018] and other tensor product states like complete graphs [Cite 15: Marti 2010a]. Even though these alternative ansätze might seem more appealing because trees kind of look like molecules, we should go with DMRG (see also Question 2 in the FAQ section) since we want a workhorse that does its job More importantly, there is no code available for these alternative ansätze which comes anywhere near the level of performance we require.

4. Integration into GTN Pipeline: Featurization

4.1 Featurization and Generalization of Graph Models

As mentioned in the overview, a short-term application would be to enhance 2D molecular graphs of deep learning models with quantum features derived from ab initio quantum chemistry simulations. Rather than familiar, global molecular descriptors, these features ought to be sufficiently indicative of the electronic correlations and serve as a proxy for the information contained in the wave function. Localized features would facilitate the transformation to atoms (nodes) and bonds (edges) and could be incorporated in the feature descriptions of known graph models. Delocalized features would require generalizing graph models to include additional structure capable of accommodating quantum correlations.

4.2 Challenges, Questions, and Remarks 4.1.1 Quantum Chemistry

What QC method to use? One reason to pick QC-DMRG is its natural connection to tensor networks, quantum information, and entanglement theory. Additionally, people have observed that cheap calculations at low bond dimensions already incorporate qualitatively okay entanglement features, in the sense that orbital entanglement entropies calculated at low bond dimension already give a measure of the entanglement in the wave function which generically survives when going to higher bond dimensions [Cite 16-18: Keller 2015, Stein 2016, Stein 2017]. That's a great observation for our purposes: this means we can get away with low bond dimensions to extract qualitatively okay information on the correlations.

If QC-DMRG turns out to not be optimal, we can resort to other more well-known ab initio quantum chemistry methods, for which we would need additional input from experienced computational chemists to decide on what is feasible and what is not. It is important to stress that our goal is not to obtain the best possible ground state energies for every particular conformation of the molecules in a dataset. That would be silly (and infeasible for the sizes of the datasets we're interested in). We need something quick and reasonably accurate.

Choice of Orbitals and Active Space?

As mentioned by the ORCA user guide
[ref: orcaforum.cec.mpg.de/OrcaManual.pdf]:
Let us stress again: it is strongly recommended to first LOOK at your orbitals and make sure that the ones that will enter the active space are really the ones that you want to be in the active space! Many problems can be solved by thinking about the desired physical contents of the reference space before starting a CASSCF. A poor choice of orbitals results in poor convergence or poor accuracy of the results! Choosing the active orbitals always requires chemical and physical insight into the molecules that you are studying!}
There's also these snippets from the MOLCAS manual:
molcas_org/documentation/manual/mode60.html
molcas.org/documentation/manual/
node61.html#SECTION04327400000000
The bottom-line appears to be that 'chemical intuition" is required.

For QC-DMRG specifically, there is also the issue of the ordering of the orbitals on the one-dimensional chain. Finding the optimal ordering is in general NP-hard, so people use heuristics, chemical intuition, or a Fiedler vector ordering obtained from the Laplacian matrix of the graph [Cite 6, 7, 9, 10, 19: Chan 2011, Wouters 2014a, Olivares-Amaya 2015, Ghosh 2008, Knecht 2015].

Irrespective of the underlying quantum-chemical method and the mapping to the atomic graphs, at least the following steps will need to be (semi-)automated when dealing with thousands of molecules (and their different confirmations):

Choice of orbitals: determines basis for the QC-DMRG calculation but is also required and extremely important for every other quantum chemistry method. We could design a heuristic scheme which takes into account a list of recommendations and proposes molecular orbitals/active spaces, plots the orbitals in real-time, and have a chemist monitor the plots to intervene when something weird is going on, preferably before doing any more time-consuming (and wrong) calculations.

Conformations: In reality, different possible conformations contribute to what is actually measured in the lab. From the point of view of the input to ab initio QC methods, one would just view every different conformation as a different problem (since it is a different geometrical configuration) and sample/average out before the conversion to the graph features.

According to Chan [cite 11: Chan 2015], DMRG is part of a wider ecosystem—except in the smallest molecules, DMRG cannot treat all degrees of freedom.

Parallelization and scaling: Computationally, the QC(-DMRG) calculations for different molecules can obviously be parallelized. For every molecule, the optimization of the wave function and subsequent calculation of all the one- and two-orbital reduced density matrices are independent. However, scaling this up will require considerations on what data we do and do not store on disk since the explicit wave functions and RDMs can get very big for a large amount of orbitals. If the calculations turn out to be sufficiently cheap, we just might want to store the correlation information and forget about the wave.

Frequently Asked Questions

1. Is it Possible to Calculate Entanglement Entropies of Orbitals and Mutual Information Between Pairs of Orbitals Using Methods Other than QC-DMRG?

Yes, sure, it's just some operation on a bunch of eigenvalues of density matrices. Even though the one-orbital and two-orbital RDMs can be naturally calculated from a QC-DMRG simulation, they can also be derived from any other method which yields N-representable one-, two-, three-, and four-particle RDMs (so you have to be very careful with methods like coupled cluster which arrive at these operators using response theory). In particular, the one-orbital RDM is given in terms of a subset of elements of the one- and two-particle RDMs and the two-orbital RDM in terms of specific elements of the one-, two-, three-, and four-particle RDMs. See Refs [Cite 20-26: Rissler 2006, Barcza 2010, Boguslawski 2012, Boguslawski 2012a, Boguslawski 2013a, Boguslawski 2015, Barcza 2015] for more details.

Why Bother Using MPS Wave Functions with a 1D Entanglement Structure for Something as Complex as Molecules? Don't these Ansätze Limit the Molecules we can Study to 1D Topologies, with Orbitals Arranged in Chains or Rings?

In the tensor network community, people often study strongly-correlated 2D quantum systems using DMRG/MPS by curling up the 1D Ansatz like a snake to cover the 2D lattice, thereby introducing unnatural long-range interactions between neighbouring sites. In many cases, the computational efficiency of MPS [due to the existence of isometric, canonical forms of the tensors which simplify the contractions (number of matrix multiplications) and also stabilize the eigenvalue problems (conditioning)] outweighs the additional complexity of 2D extensions of the MPS Ansatz such as Projected-entangled Pair States (PEPS). Actually, the development of fast and accurate numerical PEPS algorithms for 2D quantum lattice systems is still very much an active area of research.

APPENDIX 3 REFERENCES

1. C. Riplinger, and F. Neese, "An efficient and near linear scaling pair natural orbital based local coupled cluster method", Journal of Chemical Physics 138, 34106 (2013).
2. C. Riplinger, B. Sandhoefer, A. Hansen, and F. Neese, "Natural triple excitations in local coupled cluster calculations with pair natural orbitals", Journal of Chemical Physics 139, 134101 (2013).
3. S. R. White, and R. L. Martin, "Ab initio quantum chemistry using the density matrix renormalization group", Journal of Chemical Physics 110, 4127-4130 (1999).
4. S. Wouters, "Accurate variational electronic structure calculations with the density matrix renormalization group", Ghent University (2014).
5. J. Hachmann, "Ab initio density matrix renormalization group methodology and computational transition metal chemistry", Cornell University (2010).
6. S. Knecht, E. D. Hedegård, S. Keller, A. Kovyrshin, Y. Ma, A. Muolo, C. J. Stein, and M. Reiher, "New Approaches for ab initio Calculations of Molecules with Strong Electron Correlation", CHIMIA International Journal for Chemistry 70, 244-251 (2015).
7. S. Wouters, and D. Van Neck, "The density matrix renormalization group for ab initio quantum chemistry", European Physical Journal D 68 (2014) 10.1140/epjd/e2014-50500-1.
8. G. K.-L. Chan, J. J. Dorando, D. Ghosh, J. Hachmann, E. Neuscamman, H. Wang, and T. Yanai, "An Introduction to the Density Matrix Renormalization Group Ansatz in Quantum Chemistry", Progress in Theoretical Chemistry and Physics 18, 49-65-65 (2008).
9. G. K.-L. Chan, and S. Sharma, "The Density Matrix Renormalization Group in Quantum Chemistry", Annual Review of Physical Chemistry 62, 465-481 (2011).
10. R. Olivares-Amaya, W. Hu, N. Nakatani, S. Sharma, J. Yang, and G. K. L. Chan, "The ab-initio density matrix renormalization group in practice", Journal of Chemical Physics 142, 34102 (2015).
11. G. K.-l. Chan, Ab initio DMRG and beyond for realistic systems, 2015.
12. N. Nakatani, and G. K. L. Chan, "Efficient tree tensor network states (TTNS) for quantum chemistry: Generalizations of the density matrix renormalization group algorithm", Journal of Chemical Physics 138, 134113 (2013).
13. V. Murg, F. Verstraete, R. Schneider, P. R. Nagy, and Legeza, "Tree tensor network state with variable tensor order: An efficient multireference method for strongly correlated systems", en, Journal of Chemical Theory and Computation 11, 1027-1036 (2015).
14. K. Gunst, F. Verstraete, S. Wouters, Ö. Legeza, and D. Van Neck, "T3NS: Three-Legged Tree Tensor Network States", Journal of Chemical Theory and Computation 14, 2026-2033 (2018).
15. K. H. Marti, B. Bauer, M. Reiher, M. Troyer, and F. Verstraete, "Complete-graph tensor network states: A new fermionic wave function Ansatz for molecules", New Journal of Physics 12, 103008 (2010).
16. C. J. Stein, and M. Reiher, "Automated Selection of Active Orbital Spaces", Journal of Chemical Theory and Computation 12, 1760-1771 (2016)
17. C. J. Stein, and M. Reiher, "Measuring multi-configurational character by orbital entanglement", Molecular Physics 115, 2110-2119 (2017).
18. S. Keller, K. Boguslawski, T. Janowski, M. Reiher, and P. Pulay, "Selection of active spaces for multiconfigurational wavefunctions", eng, Journal of Chemical Physics 142, 244104 (2015).
19. D. Ghosh, J. Hachmann, T. Yanai, and G. K. L. Chan, "Orbital optimization in the density matrix renormalization group, with applications to polyenes and β-carotene", Journal of Chemical Physics 128, 144117 (2008).
20. K. Boguslawski, P. Tecmer, Ö. Legeza, and M. Reiher, "Entanglement measures for single- and multireference correlation effects", en, Journal of Physical Chemistry Letters 3, 3129-3135 (2012).
21. K. Boguslawski, P. Tecmer, G. Barcza, Ö. Legeza, and M. Reiher, "Orbital entanglement in bond-formation processes", Journal of Chemical Theory and Computation 9, 2959-2973 (2013).
22. K. Boguslawski, K. H. Marti, Ö. Legeza, and M. Reiher, "Accurate ab initio spin densities", Journal of Chemical Theory and Computation 8, 1970-1982 (2012).
23. G. Barcza, R. M. Noack, J. Sólyom, and Ö. Legeza, "Entanglement patterns and generalized correlation functions in quantum many-body systems", Physical Review B 92, 125140 (2015).
24. J. Rissler, R. M. Noack, and S. R. White, "Measuring orbital interaction using quantum information theory", Chemical Physics 323, 519-531 (2006).
25. G. Barcza, Ö. Legeza, K. H. Marti, and M. Reiher, "Quantum information analysis of electronic states at different molecular structures", Physical Review A 83 (2010) 10.1103/PhysRevA.83.012508.
26. K. Boguslawski, and P. Tecmer, "Orbital entanglement in quantum chemistry", International Journal of Quantum Chemistry 115, 1289-1295 (2015).
27. G. K. L. Chan, "Low entanglement wavefunctions", en, Wiley Interdisciplinary Reviews: Computational Molecular Science 2, 907-920 (2012).
28. S. Szalay, G. Barcza, T. Szilvási, L. Veis, and Ö. Legeza, "The correlation theory of the chemical bond", en, Scientific Reports 7, 2237 (2017).
29. E. Fertitta, B. Paulus, G. Barcza, and Ö. Legeza, "Investigation of metal-insulator like transition through the *ab initio* density matrix renormalization group approach", Physical Review B 90, 245129 (2014).
30. C. Duperrouzel, P. Tecmer, K. Boguslawski, G. Barcza, Ö. Legeza, and P. W. Ayers, "A quantum informational approach for dissecting chemical reactions", Chemical Physics Letters 621, 160-164 (2015).
31. G. K. L. Chan, and M. Head-Gordon, "Highly correlated calculations with a polynomial cost algorithm: A study of the density matrix renormalization group", Journal of Chemical Physics 116, 4462-4476 (2002).
32. R. J. Bartlett, and M. Musial, "Coupled-cluster theory in quantum chemistry", Reviews of Modern Physics 79, 291-352 (2007).

33 D. Zgid, and M. Nooijen, "Obtaining the two-body density matrix in the density matrix renormalization group method", The Journal of Chemical Physics 128, 144115 (2008).
34 Y. Ma, and H. Ma, "Assessment of various natural orbitals as the basis of large active space density-matrix renormalization group calculations", Journal of Chemical Physics 138, 224105 (2013).
35 Z. Li, H. Li, B. Suo, and W. Liu, "Localization of molecular orbitals: From fragments to molecule", Accounts of Chemical Research 47, 2758-2767 (2014).
36 S. F. Keller, and M. Reiher, "Determining Factors for the Accuracy of DMRG in Chemistry", en, CHIMIA International Journal for Chemistry 68, 200-203 (2014).
37 S. Wouters, T. Bogaerts, P. Van Der Voort, V. Van Speybroeck, and D. Van Neck, "Communication: DMRG-SCF study of the singlet, triplet, and quintet states of oxo-Mn(Salen)", en, Journal of Chemical Physics 140 (2014) 10.1063/1.4885815.
38 A. Kovyrshin, and M. Reiher, "Self-adaptive tensor network states with multi-site correlators", en, Journal of Chemical Physics 147, 214111 (2017).
39 M. Reiher, Three Lectures on DMRG in Quantum Chemistry Three Lectures on DMRG in Quantum Chemistry, en, edited by M. Reiher, 2014.
40 M. Reiher, DMRG in Quantum Chemistry: From its relation
41 G. Moritz, B. A. Hess, and M. Reiher, "Convergence behavior of the density-matrix renormalization group algorithm for optimized orbital orderings", Journal of Chemical Physics 122, 24107 (2005).
42 Y. Ma, J. Wen, and H. Ma, "Density-matrix renormalization group algorithm with multi-level active space", Journal of Chemical Physics 143, 34105 (2015).
43 K. Boguslawski, "How quantum entanglement can promote the understanding of electronic structures of molecules", en, 37 (2013).
44 M. Reiher, ed., The first second-generation DMRG program for quantum chemistry, en, 2014.
45 S. Sharma, and G. K.-L. Chan, "Spin-adapted density matrix renormalization group algorithms for quantum chemistry", The Journal of Chemical Physics 136, 124121 (2012).
46 C. Krumnow, L. Veis, Legeza, and J. Eisert, "Fermionic orbital optimization in tensor network states", Physical Review Letters 117 (2016) 10.1103/PhysRevLett.117.210402.
47 F. Liu, Y. Kurashige, T. Yanai, and K. Morokuma, "Multireference ab initio density matrix renormalization group (DMRG)-CASSCF and DMRG-CASPT2 study on the photochromic ring opening of spiropyran", Journal of Chemical Theory and Computation 9, 4462-4469 (2013).
48 K. H. Marti, and M. Reiher, "The density matrix renormalization group algorithm in quantum chemistry", Zeitschrift fur Physikalische Chemie 224, 583-599 (2010).
49 C. J. Stein, V. Von Burg, and M. Reiher, "The Delicate Balance of Static and Dynamic Electron Correlation", Journal of Chemical Theory and Computation 12, 3764-3773 (2016).
50 M. W. Schmidt, and M. S. Gordon, "the Construction and Interpretation of Mcscf Wavefunctions", Annual Review of Physical Chemistry 49, 233-266 (1998).
51 F. Neese, Local Correlation Approaches, en, edited by F. Neese,
52 J. B. Parkinson, and D. J. J. Farnell, "The Coupled Cluster Method", arXiv:1506.06914 [math-ph, physics: quant-ph], 109-134 (2010).
53 G. K.-L. Chan, A. Keselman, N. Nakatani, Z. Li, and S. R. White, "Matrix Product Operators, Matrix Product States, and ab initio Density Matrix Renormalization Group algorithms", arXiv:1605.02611 [cond-mat, physics:physics, physics:quant-ph] (2016) 10.1063/1.4955108.
54 Legeza, and J. Sólyom, "Optimizing the density-matrix renormalization group method using quantum information entropy", Physical Review B—Condensed Matter and Materials Physics 68, 195116 (2003).
55 D. A. Mazziotti, "Structure of Fermionic density matrices: Complete N-representability conditions", Physical Review Letters 108, 263002 (2012).
56 D. Ma, G. Li Manni, and L. Gagliardi, "The generalized active space concept in multiconfigurational self-consistent field methods", Journal of Chemical Physics 135, 44128 (2011).
57 D. Zgid, and M. Nooijen, "The density matrix renormalization group self-consistent field method: Orbital optimization with the density matrix renormalization group method in the active space", Journal of Chemical Physics 128, 144116 (2008).
58 L. Veis, A. Antalik, J. Brabec, F. Neese, Ö. Legeza, and J. Pittner, "Coupled Cluster Method with Single and Double Excitations Tailored by Matrix Product State Wave Functions", Journal of Physical Chemistry Letters 7, 4072-4078 (2016).
59 S. Wouters, W. Poelmans, P. W. Ayers, and D. Van Neck, "CheMPS2: A free open-source spin-adapted implementation of the density matrix renormalization group for ab initio quantum chemistry", Computer Physics Communications 185, 1501-1514 (2014).
60 A. Kovyrshin, and M. Reiher, "Tensor network states with three-site correlators", en, New Journal of Physics 18, 113001 (2016).

APPENDIX 4

Compact Neural Networks Based on Multiscale Entanglement Renormalization Ansatz. (A. Hallam, E. Grant, V. Stojevic, S. Severini, and A. G. Green, ArXiv e-prints (2017), arXiv:1711.03357.)

This Appendix 4 describes a method for tensorizing neural networks based upon an efficient way of approximating scale invariant quantum states, the Multi-scale Entanglement Renormalization Ansatz (MERA). We employ MERA as a replacement for the fully connected layers in a convolutional neural network and test this implementation on the CIFAR-10 and CIFAR-100 datasets. The proposed method outperforms factorization using tensor trains, providing greater compression for the same level of accuracy and greater accuracy for the same level of compression. We demonstrate MERA layers with 14000 times fewer parameters and a reduction in accuracy of less than 1% compared to the equivalent fully connected layers, scaling like O(N).

1 Introduction

The curse of dimensionality is a major bottleneck in machine learning, stemming from the exponential growth of variables with the number of modes in a data set (Cichocki et al. (2016)). Typically state-of-the-art convolutional neural networks have millions or billions of parameters. However, previous work has demonstrated that representations stored in the network parameters can be highly compressed without significant reduction in network performance (Novikov et al. (2015), Garipov et al. (2016)). Determining the best network architecture for a given task remains an open problem. Descriptions of quantum mechanical systems raise a similar challenge; representing n d-dimensional particles requires a rank-n tensor whose memory cost scales as $d^n$. Indeed, it was the promise of harnessing this that led Richard Feynman to suggest the possibility of quantum computation. In the absence of a quantum computer, however, one must use compressed representations of quantum states.

A level of compression can be achieved by factorizing the tensorial description of the quantum wavefunction. Many such factorizations are possible, the optimal structure of the factorization being determined by the structure of correlations in the quantum system being studied. A revolution in quantum mechanics was made by realizing that the best way to characterize the distribution of correlations and information in a state is by a quantity known as entanglement— loosely the mutual quantum information between partitions of a quantum system (Eisert et al. (2010)).

This has led to many successful applications of tensorial approaches to problems in solid state physics and quantum chemistry over the past 25 years (Orus (2014), Kin-Lic Chan et al. (2007)).

Intriguing ideas have also emerged over the past few years attempting to bridge the successes of neural networks in machine learning with those of tensorial methods in quantum physics, both at a fundamental level (Lin et al. (2017), Mehta & Schwab (2014)), and as a practical tool for network design (Levine et al. (2017)). Recent work has suggested that entanglement itself is a useful quantifier of the performance of neural networks (Levine et al. (2017), Liu et al. (2017)).

The simplest factorization employed in quantum systems is known as the matrix product state (Orus (2014)). In essence, it expresses the locality of information in certain quantum states. It has already been adopted to replace expensive linear layers in neural networks—in which context it has been independently termed tensor trains (Oseledets (2011)). This led to substantial compression of neural networks with only a small reduction in the accuracy (Novikov et al. (2015), Garipov et al. (2016)). Here we use a different tensor factorization—known as the Multi-scale Entanglement Renormalization Ansatz (MERA) —that encodes information in a hierarchical manner (Vidal (2008)). MERA works through a process of coarse graining or renormalization. There have been a number of papers looking at the relationship between renormalization and deep learning. MERA is a concrete realization of such a renormalization procedure (Vidal (2009)) and so possesses a multi-scale structure that one might anticipate in complex data. A number of works have utilized tree tensor network models that possess a similar hierarchical structure. However, they do not include the disentangler tensors that are essential if each layer of the MERA is to capture correlations on different length scales (Liu et al. (2017)).

In this work we employ MERA as a replacement for linear layers in a neural network used to classify the CIFAR-10 and CIFAR-100 datasets. Our results show that this performs better than the tensor train decomposition of the same linear layer, and gives better accuracy for the same level of compression and better compression for the same level of accuracy. In Section 3.2 we introduce factorizations of fully connected linear layers, starting with the tensor train factorization followed by a tree-like factorization and finally the MERA factorization. In Section 3.3 we discuss how this is employed as a replacement for a fully connected linear layer in deep learning networks. Section 3.4 gives our main results and we note connections with the existing literature in Section 3.5. Finally, in Section 3.6 we discuss some potential developments of the work.

2 Tensor Factorization of Linear Layers

In this report we have replaced the linear layers of the standard neural network with tensorial MERA layers. The first step in achieving this involves expressing a linear layer as a tensor. This can be accomplished by taking a matrix $w$ and reshaping it to be a higher dimensional array. For example, suppose $w$ is $d^n$ by $d^n$ dimensional with components $w_{AB}$. It can be transformed into a rank 2n tensor by mapping A to n elements $A \rightarrow i_1, i_2, \ldots, i_n$ and B to another n elements $B \rightarrow j_1, j_2, \ldots, j_n$. In this case each of the elements of the new tensor will be of size d.

Figure 41:
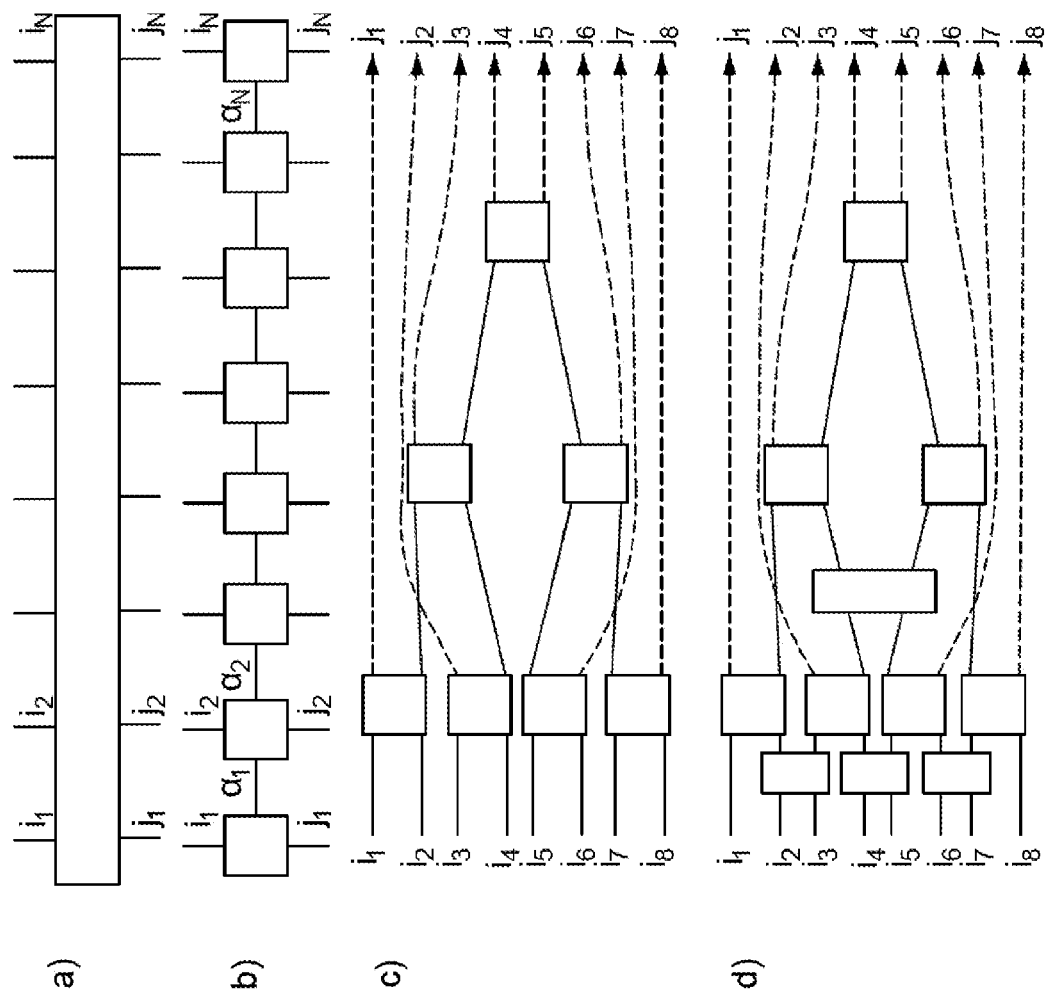
FIG. 41 shows schematic diagrams of various tensor factorizations of linear layers.

FIG. 41 shows schematic diagrams of various tensor factorizations of linear layers: a) a general linear layer, b) its tensor train factorization. The squares represent smaller tensors. Connections represent contractions as indicated in Equation 1 (as seen in FIG. 42) c) Tree network factorization. d) MERA factorization.

FIG. 41a gives a graphical representation of this rank $2_n$ tensor $$W^{i_1,i_2,\ldots,i_n}_{j_1,j_2,\ldots,j_n}.$$

It is important to note that in this representation, the lines represent the indices of the tensors rather than weights. FIG. 41b illustrates the tensor train decomposition of $w$. This consists of writing the larger tensor as the contraction of a train of smaller tensors, as shown in Equation 1 (FIG. 42).

$$W^{i_1,i_2,\ldots,i_n}_{j_1,j_2,\ldots,j_n} = \sum_{\alpha_1,\alpha_2,\ldots,\alpha_{n-1}} A^{i_1}_{j_1,\alpha_i} A^{\alpha_1,i_1}_{j_1,\alpha_2} \ldots A^{\alpha_{n-1},i_n}_{j_n}. \quad (1)$$

In the tensor graphical notation, closed legs represent indices being summed over and free legs represent indices that aren't being summed over. For example, in equation 1 the $\alpha_i$ indices are being summed over and in FIG. 41b the $\alpha_i$ lines are connected to tensors at both ends.

If each index runs over values from 1 to d, this represents an exponential reduction from $d^{2n}$ parameters to $n(Dd)^2$, where the indices a run over values from 1 to D (known as the bond order or Schmidt rank in the quantum context). As noted above, this type of tensor factorization works well in physics when the information has a local structure (Eisert et al. (2010), Verstraete & Cirac (2006)); tensor trains capture correlations effectively up to length scales of order log D (Schollwock (2011)). This means that while useful for many tasks, the learned representations will be highly local. Tensors at either end of a tensor train decomposition of a linear layer will not be strongly correlated with one another.

A hierarchically structured tensor network can better represent correlations across the linear layer.

The tree tensor network shown in FIG. 41c represents one possible hierarchical factorization. Each element of this network is a rank 4 tensor. The two tensors on the top left would have the form:

$$M_{i_1,i_2}^{j_1,\alpha_1} \text{ and } \mathcal{N}_{i_3,i_4}^{j_2,\alpha_2}.$$

The $i_n$ elements being represented by the lines on the left of the figure, the $j_n$ elements represented by the dotted lines on the right of the figure and the $\alpha_n$ lines being those connected with the tensor immediately to the right of $\mathcal{M}$ and $\mathcal{N}$.

Reading from left to right FIG. 41c can be interpreted as follows: the tree-like connectivity imbues the network with a causal structure whereby a given linear element and its outputs are influenced by inputs in a region determined by its height in the tree.

For example, the rightmost element in FIG. 41c is influenced by all of the inputs, whereas the top element in the middle column is influenced by inputs $i_1$ to $i_4$. Elements other than the rightmost tensor have one dashed output (that connects directly to the overall output) and one solid output (that ties it to the branching tree structure). These dashed lines are controlled by representations occurring on a particular scale in the data.

Notice that removing these dashed lines, the network has a true tree structure and represents a coarse graining or renormalization of the network. In this case, the linear elements are the isometries of the original MERA's definition (Vidal (2008; 2009)).

The simple tree network, which has been studied before in the context of neural networks, has a major deficiency. At each branching, it partitions the system in two, so that in extremis, the correlations between neighbouring inputs—for example i4 and i5 in FIG. 41c—are only controlled by the element at the end of the network. Requiring the higher elements in the tree-structure to capture correlations between neighbouring inputs restricts their ability to describe the longer length scale correlations you would hope to capture by using a hierarchical structure.

The MERA (Vidal (2009)) factorization was introduced in order to solve this problem. As can be seen in FIG. 41d it adds an additional set of rank 4 tensors called disentanglers. The MERA is constructed by taking a tree network and placing one of these rank 4 tensors $\mathcal{D}_{\gamma_1,\gamma_2}^{\beta_1,\beta_2}$ such that its right-going legs $\beta_1$ and $\beta_2$ connect to two adjacent tensors of the tree network. For example, if we consider the top left-most disentangler in FIG. 41d it has elements $\mathcal{D}_{i_2,i_3}^{\beta_1,\beta_2}$ and connects to the tree and $\mathcal{N}'^{j_2,\alpha_2}_{\beta_2,i_4}$ with $\beta_1$ and $\beta_2$ then being summed over.

The role of the disentanglers is to cause all correlations on the same length scale to be treated similarly. For example, correlations between any two neighbouring input indices $i_n$ and $i_{n+1}$ will be captured by either the first row of tree elements or the disentanglers. This allows the later elements in the network to work at capturing longer range correlations.

In summary, a rank-N MERA layer can be constructed in the following manner:
1. Create a tree tensor layer. For example, an N=$2^\tau$ tree can be constructed from $2^{\tau-1}$ rank-4 tree tensors $\mathcal{M}_{\gamma_1,\gamma_2}^{\beta_1,\beta_2}$ in the first layer, followed by $2^{\tau-2}$ tree tensors in the second layer until after $\tau$ layers there is only a single tree tensor.
2. A set of disentanglers are introduced. These are rank-4 tensor $\mathcal{D}_{\gamma_1,\gamma_2}^{\beta_1,\beta_2}$ which are placed such that every disentangler is contracted with two neighbouring tree tensors in an upcoming layer of the tree tensor.

3 Experiments and Network Structure

We have considered the performance of a neural network with the two penultimate fully connected layers of the model replaced with MERA layers, similar to the Novikov et al. (2015) study of compression of fully connected layers using tensor trains. We have quantified the performance of the MERA layer through comparisons with two other classes of networks: fully connected layers with varying numbers of nodes and tensor train layers with varying internal dimension. The three types of network are otherwise identical. The networks consisted of three sets of two convolutional layers each followed by max pooling layers with 3×3 kernels and stride 2. The convolutional kernels were 3×3. There were 64 channels in all of the convolutional layers except for the input, which had three channels, and the last convolutional layer, which had 256 channels. The final convolutional layer was followed by two more hidden layers, these were either fully connected, MERA layers or TT-layers depending upon the network. The first of these layers was of size 4096×x, the second is of size x×64. For the MERA and TT networks, these layers were 4096×4096 and 4096×64.

The final layer had 10 or 100 nodes corresponding to the image classes in CIFAR-10 and CIFAR-100. Leaky rectified linear units (LReLU) were used on all layers except the final layer, with leak=0:2 (Maas et al. (2013)).

During training, nodes in the final convolutional layer and the two first fully connected layers were dropped with probability 0:5. The penultimate convolutional layer nodes were dropped with probability 0:2 (Srivastava et al. (2014)). Batch-normalization was used on all layers after dropout and max pooling (Ioffe & Szegedy (2015)). We did not use bias units. Gaussian weight initialization was employed in the fully connected models with standard deviation equal to $$\frac{1}{\sqrt{n_{in}}},$$

where $n_{in}$ was the number of inputs (He et al. (2015)).

In this report we considered networks with two varieties of fully-connected layers. The first of these networks had a 4096×4096 fully connected layer followed by one which was 4096×64; this network was used as a benchmark against which the other models could be compared. The second network instead had a 4096×n fully connected layer followed by a n×64 layer where n=5 for the CIFAR-10 network and n=10 for the CIFAR-100 network. We trained these network to compare the MERA and tensor train layers to a fully connected model with a comparable number of parameters, in order to evaluate how detrimental naive compression is to accuracy.

Figure 43:
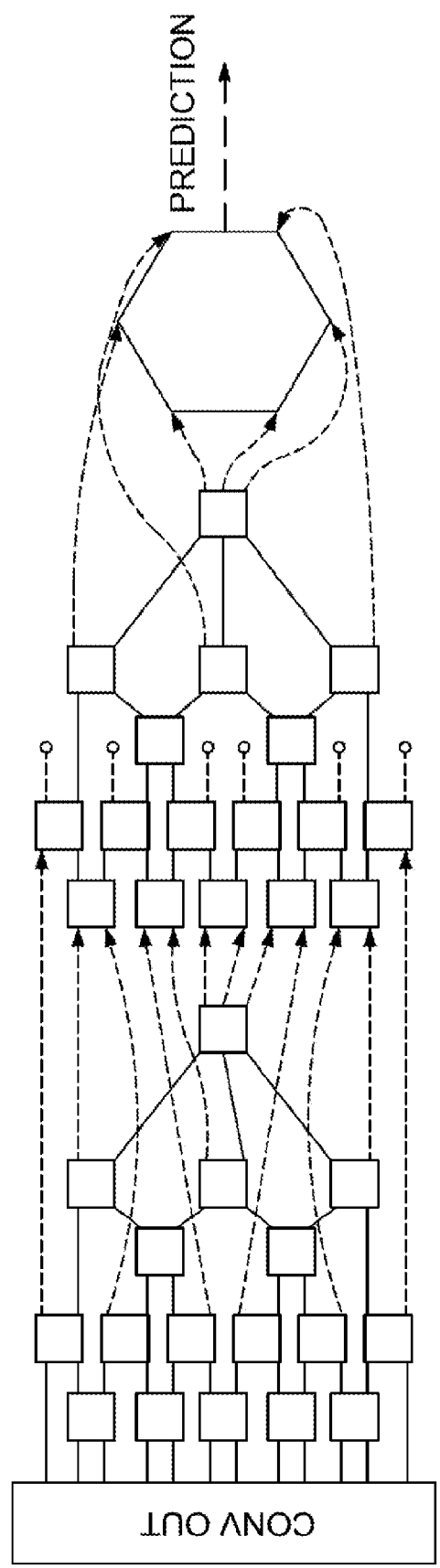
FIG. 43 shows a schematic of the MERA layers of the model.

A schematic of the two MERA layers can be found in FIG. 43. The input to the first MERA layer was reshaped in to a rank-12 tensor with each index being dimension 2, as described in Section 3.2. The MERA layer was then constructed from a set of rank-4 tensors using the method described in Section 3.2.

FIG. 43 shows a schematic of the MERA layers of the model. The small rectangles represent linear elements to factorize a general linear layer. White rectangles represent disentanglers. Black rectangles represent tree elements. Solid black lines connecting nodes represent tensor contraction and dashed lines with arrow heads represent the non-linearities being applied. Dashed lines ending in a circle represent fixed outputs.

The first MERA layer works as follows: It contains a column of 6 rank-4 tree elements, followed by 3 tree elements and finally a single tree element. 5 disentanglers are placed before the first column of tree elements and 2 more disentanglers are placed before the second column of tree elements.

The second MERA layer has an identical structure to the first MERA layer, one of the outputs of the first set of tree elements is fixed. As a result the output of the second MERA layer is 64 nodes. MERA weights were initialized using elements of randomized orthogonal matrices (Saxe et al. (2013)). The tensors themselves were constructed by reshaping these matrices, as described in Section 3.2. The random orthogonal matrix was constructed using the method of Stewart Starting from a random n−1×n−1 dimensional orthogonal matrix, a random n×n dimensional orthogonal matrix can be constructed by taking a randomly distributed n-dimensional vector, constructing its Householder transformation, and then applying the n−1 dimensional matrix to this vector. Finally, a network with its fully connected layers replaced with a tensor train decomposition was trained in order to provide a comparison with the MERA layers. The tensor train layers were constructed as described in Section 3.2 with the internal dimension being fixed at D=3. In the second tensor train layer, half of the output indices were fixed to match the second MERA layer. We tested performance on the CIFAR-10 and CIFAR-100 datasets. We used 45; 000 images for training, 5; 000 for validation and 10; 000 for testing. Each training batch consisted of 50 images.

Training data was augmented by randomly flipping and translating the input images by up to 4 pixels. Translated images were padded with zeros. All images were normalized by dividing by 255 and subtracting the mean pixels value from the training set.

Validation and test set accuracy was recorded every 500 iterations and training was stopped when validation accuracy did not improve for 10 successive tests. The network was trained using backpropagation and the Adam optimizer, with initial learning rate 0:001 (Kingma & Ba (2014)) and a softmax-cross-entropy objective. The test set accuracy for the model with the highest validation set accuracy was recorded. Each network was trained 10 times with a different random weight initialization.

The networks were implemented in Tensorflow r1.3 and trained on NVIDIA Titan Xp and 1080ti GPUs.

4. Experimental Results

FIG. 44 shows a table of results in which we compare the different models described in section 3.3 trained on the CIFAR-10 dataset. FC1 was the fully-connected model and FC2 was the fully-connected model with severely reduced number of parameters in the fully-connected layers. MERA are the result for the MERA inspired network. Finally TT is the tensor train model with the internal dimension being 3.

The compression rate stated is with respect to the number of parameters used in the fully-connected benchmark model, FC-1.

When comparing the MERA network to the fully connected model, FC-1 we see a considerable drop in the number of parameters required with only a modest drop in the accuracy of the network.

MERA compresses the fully connected layers by a factor of 14,000 with a drop in the accuracy of only 0:4%. We do not attempt to compress the convolutional layers in this work so in the MERA network the vast majority of the parameters are used in the convolutional layers, which are identical to the fully connected model.

How significant is the MERA network structure we have chosen to the results obtained? To test this we compare the MERA results obtained to the fully connected model with many fewer parameters in the fully connected layers, FC-2. Despite having around 20 times more parameters in the fully connected layer than the MERA model, the MERA model significantly out performs FC-2, with a 1:2% drop in the accuracy of FC-2 compared to MERA. The MERA network also compares favourably to a tensor train network. In this case, the two networks have a comparable number of parameters but the MERA appears to achieve a higher accuracy than the tensor train network in this case.

Results for the CIFAR-100 model can be seen in FIG. 45. While none of the networks are as accurate as the benchmark case, the MERA network continues to outperform the tensor train and ablated fully connected network. However, the reduction in accuracy compared to the fully connected network is larger than for the CIFAR-10 dataset.

In addition to the degree of compression achieved by these networks, we also address the time to optimize. There is evidently a degree of compromise required here: the number of multiplications required to apply a MERA layer scales with the input size N and bond order D as $N^{log\ 2\ D}$. The equivalent scaling for a tensor train and fully connected layer are $ND^2$ and $N^2$, respectively. This is reflected in the times taken to optimize these networks. Note however, that MERA can accommodate correlations at all scales of its input even at low bond order, whereas tensor trains require a bond order that scales exponentially with the length scale of correlation (Orus (2014)). MERA is, therefore, expected to scale better for very large data sets than either tensor trains or fully connected layers.

5 Related Work

Given how memory intensive deep neural networks typically are, substantial effort has been made to reduce number of parameters these networks require without significantly reducing their accuracy. Some of these have taken a similar approach to the MERA network described above, using tensor decompositions of the fully connected layers.

These include the tensor train models of Novikov et al. (2015) and Garipov et al. (2016). Here we have found replacing a fully connected linear layer with a MERA factorization resulted in superior accuracy for a comparable number of parameters. More directly related to this MERA model are a number of tree tensor network models (Liu et al. (2017), Levine et al. (2017)). As Section 3.2 explained, tree tensor networks inconsistently capture correlations on the same length scale, this is the reason for the introduction of disentanglers. Tree tensors do not possess these and we expect them to struggle to capture long range correlations as effectively as MERA.

A MERA works through a process of coarse graining or renormalization. There have been a number of other papers looking at the relationship between renormalization and deep learning. Lin et al. (2017) argue that the effectiveness of deep neural networks should be thought of in terms of renormalization and Mehta & Schwab (2014) demonstrate an exact mapping between the variational renormalization group and restricted Boltzmann machines. In this report we have taken a different approach: only the fully connected layers of the network were replaced with MERA layers.

6 Discussion

We have shown that replacing the fully connected layers of a deep neural network with layers based upon the multi-scale entanglement renormalization Ansatz can generate significant efficiency gains with only small reduction in accuracy. When applied to the CIFAR-10 data we found the fully connected layers can be replaced with MERA layers with 14,000 times less parameters with a reduction in the accuracy of less than 1%. The model significantly outperformed compact fully connected layers with 70-100 times as many parameters. Moreover, it outperformed a similar replacement of the fully connected layers with tensor trains, both in terms of accuracy for a given compression and compression for a given accuracy. While the MERA layer resulted in a larger accuracy drop in the CIFAR-100 case, it still outperformed a comparable tensor train network.

An added advantage—not explored here—is that a factorized layer can potentially handle much larger input data sets, thus enabling entirely new types of computation. Correlations across these large inputs can be handled much more efficiently by MERA than by tensor trains. Moreover, a compressed network may provide a convenient way to avoid over-fitting of large data sets. The compression achieved by networks with these factorized layers comes at a cost. They can take longer to train than networks containing the large fully connected layers due to the number of tensor contractions required to apply the factorized layer.

Our results suggest several immediate directions for future inquiry. Firstly, there are some questions about how to improve the existing model. For example, before the MERA layer is used the input is reshaped into a rank-12 tensor. There isn't a well defined method for how to perform this reshaping optimally and some experimentation is necessary. The best way to initialize the MERA layers is also still an open question.

The results presented here are a promising first step for using MERA in a more fundamental way.

Since MERA can be viewed as a coarse graining procedure (as explained in Section 3.2), and image data is often well represented in a hierarchical manner, one possibility would be to simply train a two-dimensional MERA directly on an image dataset, with no reference to a neural network. In Stoudenmire & Schwab (2016) a similar idea was explored with matrix product states being trained directly on MNIST. An alternative possibility would be the replacement of just the convolutional layers of the network with a two-dimensional MERA. Both of these approaches would be closer in spirit to the fundamental ideas about the relationships between quantum physics and machine learning proposed in Lin et al. (2017) and Mehta & Schwab (2014).

Additionally, there has been some work using entanglement measures to explore how correlations are distributed in deep neural networks, and then utilizing these in order to optimize the design of networks (Liu et al. (2017), Levine et al. (2017)). It would be intriguing to explore such ideas using MERA, for example by using the concrete MERA model explored in this paper, or one of the more ambitious possibilities mentioned above.

We end by noting two facts: any variational approximation to a quantum wavefunction can be used to construct a replacement for linear layers of a network. There are many examples and each may have its sphere of useful application. Moreover, quantum computers of the type being developed currently by several groups are precisely described by a type of tensor network (a finite-depth circuit—and one that may very soon be too large to manipulate classically) and could be used as direct replacement for linear layers in a hybrid quantum/classical neural computation scheme.

APPENDIX 5

Operator Expectation Value

Background

In machine learning terminology, the term "tensors" conventionally refers to multi-dimensional arrays. The description of a quantum state is in general exponentially large in the number of constituents (for example the electrons of an atom), for precisely the same reasons that one encounters curse of dimensionality issues with high dimensional data in machine learning. For example, for a system of spin-½ particles, such as electrons, the wave function describing them will be described by a $2^n$ dimensional vector space, or equivalently an n-dimensional array. In this example, only spin is taken into account, and positional information is ignored, i.e. where the electrons are in space.

Tensorial methods have been used in quantum physics to beat the curse of dimensionality, generally by decomposing a larger tensor into smaller constituents that can be re-assembled using tensor contractions in order to calculate quantities of interest. The aim of the re-assembly recipe is to obtain the quantities of interest efficiently (meaning polynomially in the number of basic constituents) —sometimes this can only be achieved using approximate methods, and sometimes it is believed that an efficient recipe will only be possible using appropriate algorithms on quantum computers, once and if these become available. Such a decomposition, and the recipe on how to reconstruct the larger tensor, is called a tensor network. Deciding what type of decomposition is appropriate for a given physical situation has been considered a difficult problem in general, and has been explored by physicists extensively over the past 20-30 years.

Summary

Aspects and/or embodiments seek to provide a method, apparatus, and system related to the search, sampling, statistical analysis and visualisation of vast multi-dimensional datasets, i.e. those that are naturally described by multi-dimensional arrays, or equivalently tensors. The data can be obtained from real world measurements or generated synthetically (in silico). The patent utilises above-mentioned quantum physics inspired tensor networks as enhancements for both predictive as well as generative machine learning models.

According to a first aspect, there is provided a method for generating an expectation value of an operator, the method comprising the steps of: providing a first set of input data; applying a first transformative network to the first set of input data to produce a first set of transformed data; providing a second set of input data; applying a second transformative network to the second set of input data to produce a second set of transformed data; providing the first set of transformed data and the second set of transformed data to an operator; and generating an expectation value from the operator.

The operator expectation value is the output of the network. The operator can itself have "output legs", which may comprise vectors and/or matrices, or one or more of any general tensorial object. The network may be trained using standard machine learning methods, so everything that a standard machine learning algorithm can do, the expectation value network disclosed herein can do as well. The cost function may be given in terms of data inputs and outputs, and the optimisation can be done utilising standard machine learning approaches, e.g. stochastic gradient descent. The structure of the network and the way it may be generalised to quantum computing may provide usefulness and efficiency over existing networks.

Optionally, the first and/or second set of input data comprises one or more of: a tensor; a tensor network; a string; a vector, a matrix; and/or a higher dimensional array.

Such arrangements can provide convenient ways to transfer and communicate data digitally.

Optionally, the first and/or second transformative network is constructed in such a manner as to respect the tensor and/or tensor network structure of their respective input data.

Examples of transformative operations that are then projected back into the format of original data include projections in the DMRG algorithm set out in the paper "The density-matrix renormalisation group" in Reviews of Modern Physics, vol. 77, Issue 1, pp. 259-315 by Schollwock, U (see http://adsabs.harvard.edu/cgi-bin/bib_query?arXiv:cond-mat/0409292), and the more general projection described in the paper "Geometry of matrix product states: Metric, parallel transport, and curvature" in Journal of Mathematical Physics, Volume 55, Issue 2, id. 021902 by Haegeman, Jutho; Mariën, Michaël; Osborne, Tobias J.; and Verstraete, Frank (see http://adsabs.harvard.edu/cgi-bin/bib_query?arXiv:1210.7710), which while mostly developed in the context of matrix product state tensor network, generalise to more complex multi-dimensional tensor networks.

Optionally, the first and/or second set of input data comprises one or more bits. Optionally, the first and/or second transformative network is operable to act directly on the one or more bits.

The one or more bits may be referred to as a "sequence of bits" or a "collection of bits". Conventionally it is unlikely that a circuit for practical use will be acting on a single bit only, as the operations that could be performed would be very limited.

Optionally, the first and/or second transformative network and/or the operator comprises computer circuits built from standard gates comprising one or more of: AND; OR; NAND; and/or NOR gates, in combination with explicit non-linear functions.

The input to the circuits may be represented or constructed as a binary or raw representation of input data.

Optionally, the first set of input data is identical to the second set of input data.

Such an arrangement can provide an efficient analysis and reconstruction of the relevant data.

Optionally, the first and/or second transformative network and/or the operator comprises one or more of: a neural network; and/or a tensor network. Optionally, the first and/or second transformative network and/or the operator comprises one or more of: a complete-graph tensor network state; a correlator product state; projected entanglement pair states (PEPS), matrix product states (MPS); a tensor train; a matrix product operator, and/or a multi-scale entanglement renormalization Ansatz (MERA) network.

The transformative network and/or operator constructions can provide efficient analysis and deconstruction/reconstruction of input data.

Optionally, the first and/or second set of input data comprises one or more quantum bits.

The one or more bits may be referred to as a "sequence of bits" or a "collection of bits". Conventionally it is unlikely that a circuit for practical use will be acting on a single bit only, as the operations that could be performed would be very limited.

Optionally, the first and/or second transformative network comprises a quantum circuit.

Optionally, an operation performed by gates of the quantum circuit is a function of one or more adjustable parameters. Optionally, the quantum circuit is operable to act on an input quantum state. Optionally, the input quantum state is in a general and/or entangled state. Optionally, the first and/or second set of transformed data is represented as a quantum state. Optionally, the expectation value from the operator is identified by measuring the operator on the quantum state a plurality of times in order to obtain the expectation value of the operator statistically.

The quantum circuit may be provided without any reference to a classical computing circuit, or may be derived from a classical circuit alongside a non-linear function setup. The generalisation of the non-quantum circuit may be performed in the conventional manner, (as described in e.g. Michael A. Nielsen and Isaac L. Chuang. 2011. Quantum Computation and Quantum Information: 10th Anniversary Edition (10th ed.). Cambridge University Press, New York, NY, USA). The classical non-linear transformations are first transformed into tensorial transformations, along the lines of what is described in Deep Learning and Quantum Entanglement: Fundamental Connections with Implications to Network Design, Levine, Yoav; Yakira, David; Cohen, Nadav; Shashua, Amnon, eprint arXiv:1704.01552. The tensors are then embedded into a unitary matrix (the unitary matrix can itself be expressed as a quantum circuit) using a conventional procedure. Measuring these spurious qubits may have the desired effect of introducing non-linear transformations on those qubits in the circuit that are of direct relevance to our machine learning algorithm. Embedding the tensor into a unitary matrix may result in a number of spurious output cubits, in addition to the ones that are part of the original tensor and therefore are relevant to the disclosure herein. The sole role of these spurious qubits is to effectively introduce non-linearities on the qubits that were outputs and inputs of the original tensor, via their measurement in the quantum algorithm. The adjustable parameters can be, for example, the values of the entries in the fundamental (usually these are one-qubit or two-qubit operations) unitary matrices from which the quantum circuit is constructed. Alternatively, they can provide a parameterisation for such unitary matrices. For example, the parameters could be the angles parameterising a SU(2) matrix 2-quibit operation in the quantum circuit. The input quantum state may be in a general and/or entangled state, as opposed to a state that is simply a set of one or more non-entangled qubits (i.e. a product state).

Optionally, the first and/or second set of transformed data comprises one or more of: a tensor, a tensor network; a string; a vector, a matrix; and/or a higher dimensional array. Optionally, the first and/or second set of transformed data and/or the operator comprise a plurality of sub-components. Optionally, the plurality of sub-components comprises: a tensor; a string; a vector; a matrix; and/or a higher dimensional array. Optionally, the first and/or second set of transformed data and/or the operator comprise five sub-components. Optionally, providing the first and/or second set of transformative data to the operator comprises a matrix vectorial dot product operation.

A tensor network conventionally comprises a larger tensor decomposed in terms of a number of smaller tensors. The smaller tensors can, via tensor contraction, be used to reconstruct the larger tensor and other quantities of interest, for example functions of the larger tensor. Their utility lies in the fact certain quantities of interest (e.g. energy in physics) can be calculated in a computationally efficient way using the tensor network, but would be computationally intractable if the larger tensor was used directly. As disclosed herein, a tensor may comprise a multi-dimensional array. Further, a vector, or a matrix may be special cases of a tensor, i.e. rank-0, rank-1, and rank-2 multi-dimensional arrays. Tensor networks are often used in physics to represent quantum states. A quantum circuit can be represented as a special type of tensor network, wherein the small tensors are the one and two qubit gates, and they are used to construct the large unitary which takes the input state and emits an output state. Tensors, or tensor networks, are conventionally not themselves thought of as quantum states or circuits, (which in the quantum computer are actual physical objects, i.e. physical entangled qubits, and the gates acting on these in the quantum computer), but are classical descriptions of quantum states or circuits.

Optionally, the first and/or second transformative network and/or the operator is trained using stochastic gradient descent.

Stochastic gradient descent is a computationally efficient method for training a machine learning network. However, a range of different training arrangements may be used.

Optionally, there is provided herein a method for training a machine learning algorithm. Optionally, the expectation value from the operator comprises a predictor for machine learning.

Standard machine learning methods can be applied directly to the network arrangement disclosed herein.

Optionally, there is provided herein a method operable to analyse a chemical compound dataset so as to determine suitable chemical compounds and/or properties of interest related to a chemical compound including any of: solubility; toxicity; binding affinity; and/or binding energy.

According to a further aspect, there is provided an apparatus for generating an expectation value of an operator, comprising: means for providing a first set of input data; means for applying a first transformative network to the first set of input data to produce a first set of transformed data; means for providing a second set of input data; means for applying a second transformative network to the second set of input data to produce a second set of transformed data; means for providing the first set of transformed data and the second set of transformed data to an operator, and means for generating an expectation value from the operator.

According to a further aspect, there is provided a system for generating an expectation value of an operator, comprising: means for providing a first set of input data; means for applying a first transformative network to the first set of input data to produce a first set of transformed data; means for providing a second set of input data; means for applying a second transformative network to the second set of input data to produce a second set of transformed data; means for providing the first set of transformed data and the second set of transformed data to an operator, and means for generating an expectation value from the operator.

The operator expectation value in the classical algorithm is calculated using the explanation and diagrams disclosed herein. The first set of transformed data and the second set of transformed data are contracted with the operator network using tensorial contractions. In one embodiment, the first set of transformed data is a vector, as is the second set of transformed data. The operator network is then a matrix, and the operator expectation value can be considered as this matrix acting on the first set of transformed data, producing another vector. The dot product of this vector with the right transformed data can produce the operator expectation value. The operator expectation value may be determined by a tensor network diagram that specifies the contractions that need to be performed in order to take the left transformed data, right transformed data, and the operator and produce the operator expectation value. An example of a simple tensor network of this kind is provided in FIG. 63, where the operator tensors O_1 to O_5 may each be defined in terms of tensor networks.

The operator expectation value can be used as a predictor in machine learning. For example, the input data could comprise images, and the predictor could output the number of cats in the image; or the input could be a description of a quantum state, and the predictor could be its energy. For one or more of the examples disclosed herein it may be assumed that both the left and right input data are the same. In this embodiment, the operator network takes the left and right transformed data and produces a single number. More generally, the operator itself can have an output. This output could be a vector, which may comprise a softmax layer added on top of it in order to decide, for example, whether the input images in the above example contain cats, cars, horses, or cars.

Data may be taken in the classical algorithm, expressed as a set of bits (0s and 1s), and mapped to a qubit input on the quantum computing side (classical 0 is mapped to a qubit pointing 'down', and 1 to a qubit pointing 'up'). On the classical side, a standard training approach may be used, wherein the predictors are minimised with respect to the training data using standard cost functions. The predictor on the quantum side is obtained by actually measuring the operator (described by the operator network) on the quantum state many times in order to obtain the expectation value of the operator statistically. The quantum state on which the measurement of the operator expectation value is performed is the result of applying the transformative quantum circuit (equivalent of the transformative network on the classical side) to the inputs. More generally, in the case when left and right inputs are different, the quantum measurement corresponds to obtaining the amplitude of the quantum state corresponding to the transformed right input data into the quantum state corresponding to the transformed left input data, with an insertion of the operator. Therefore, in the quantum algorithm, the parameters as previously disclosed are updated using results of these measurements. There may be no quantum element regarding these parameters i.e. they are just real or complex numbers, but they may be operable to be updated using a result of an average of quantum measurements. In the classical algorithm, the parameters (or equivalently the weights) may be updated using backpropagation. In the quantum computer implementation (or quantum version), the cost function and the updates of the weights classically obtained using back propagation are obtained via quantum measurements.

Specific Description

FIG. 38 is a diagram showing an example of a decomposition of a tensor into a matrix product state. Such an operation is performed in the fourth step of the method disclosed herein. The matrix product state shown may also be referred to as a "tensor train". Examples of possible decompositions are shown in Roman Orus, A practical introduction to tensor networks: Matrix product states and projected entangled pair states, Annals of Physics, Volume 349, p. 117-158 and Cichocki, A.; Lee, N.; Oseledets, I. V.; Phan, A-H.; Zhao, Q.; Mandic, D., Low-Rank Tensor Networks for Dimensionality Reduction and Large-Scale Optimization Problems: Perspectives and Challenges, eprint arXiv:1609.00893.

The elements referred to as "d" represent the size of each of the modes of the order N tensor $\Psi$ (which is here assumed to be the same for all modes, however, this need not be the case in general). For every value of $i_a$, $A^{ia}$ is a D×D matrix.

FIG. 39 shows a schematic decomposition of a mode-5 tensor as a matrix product state (or "tensor train").

FIG. 40 shows a schematic drawing depicting the effect of a quantum physics tensor decomposition, reducing a state that is exponentially expensive, in the number of modes, to store and manipulate, to one which imposes a prior and whose representation is polynomial in the number of modes. The exponentially expensive state comprises part of what is conventionally referred to as the "curse of dimensionality", in that the size of the quantum wave function is exponential in the number of particles.

Figure 63:
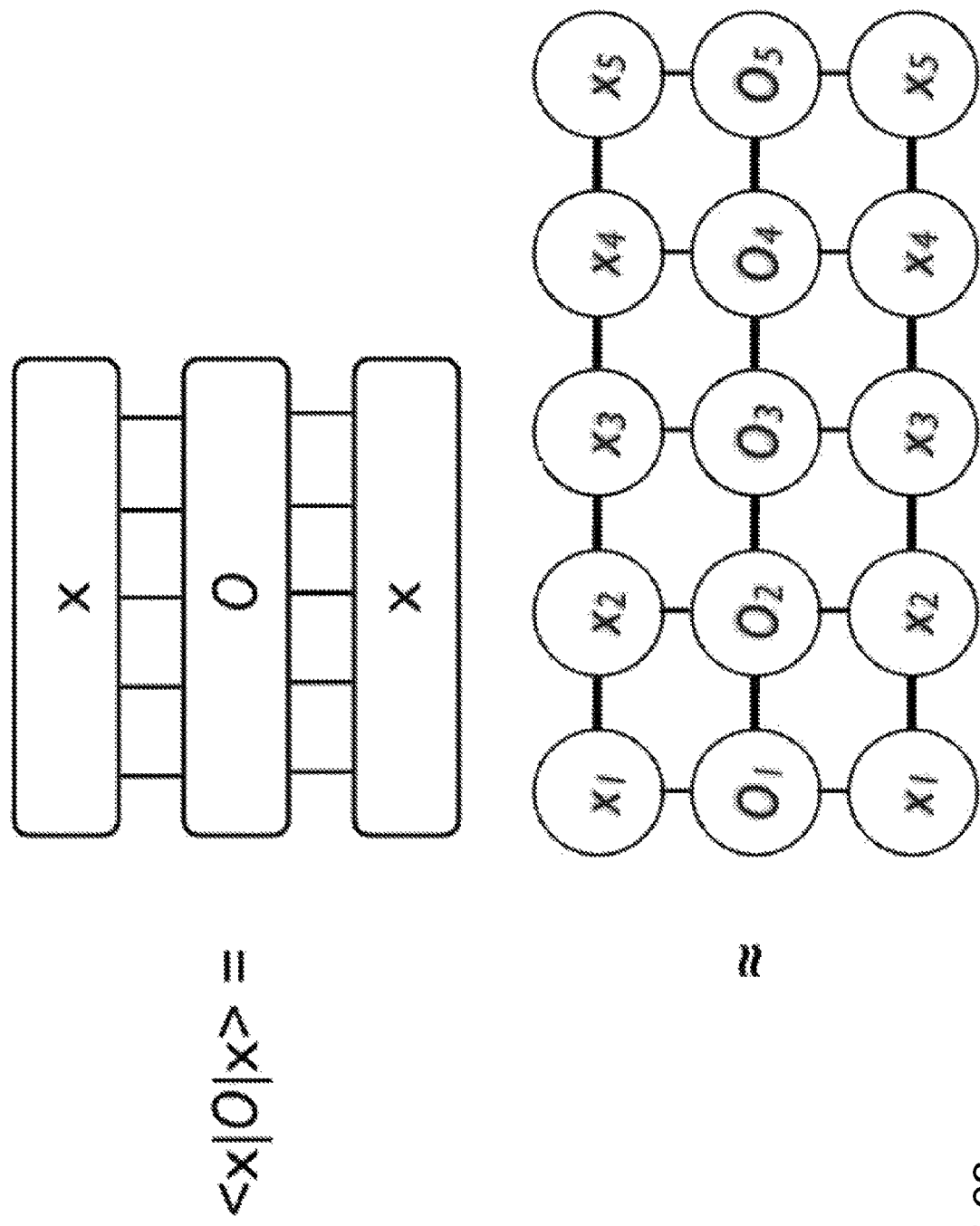
FIG. 63 shows a tensorial representation for an expectation value of an operator, in the standard quantum mechanical sense.

FIG. 63 shows a tensorial representation. In quantum mechanics, an experiment may be represented by an operator "O", which can be thought of as a large matrix or a linear operator acting on a quantum wave function. The wave function is denoted as |x>. For present purposes, the wave function as given by a tensor. The result of an experiment, or, more accurately, the average result over many runs, is given by the expectation value of O, which corresponds to:

$$<x|O|x>$$

Reading this from right to left, |x> is the state under study, which is then acted upon by the operator O. This represents the act of doing the experiment, and yields another vector. To obtain the average, the dot-product is taken with |x> (notationally the dot product may be represented by "flipping" |x> to <x|). If, for example, the initial state is given by some tensor, |x> may then be "reshaped" into a vector. In the programming language of Python this corresponds to applying the numpy.reshape( ) function. Equivalently, one can remain in the original tensorial representation throughout, but then the aforementioned vector dot-product step may require replacement by an appropriate tensorial contraction.

The tensorial representation of <x|O|x> is pictorially shown in FIG. 63. The second line represents a tensorial decomposition of the three objects <x|, O, and |x> in terms of five smaller sub-tensors. This is an example of a simpler kind of tensor network, comprising so-called matrix product state decompositions of <x| and |x>, and a matrix product operator decomposition of O.

Figure 64:
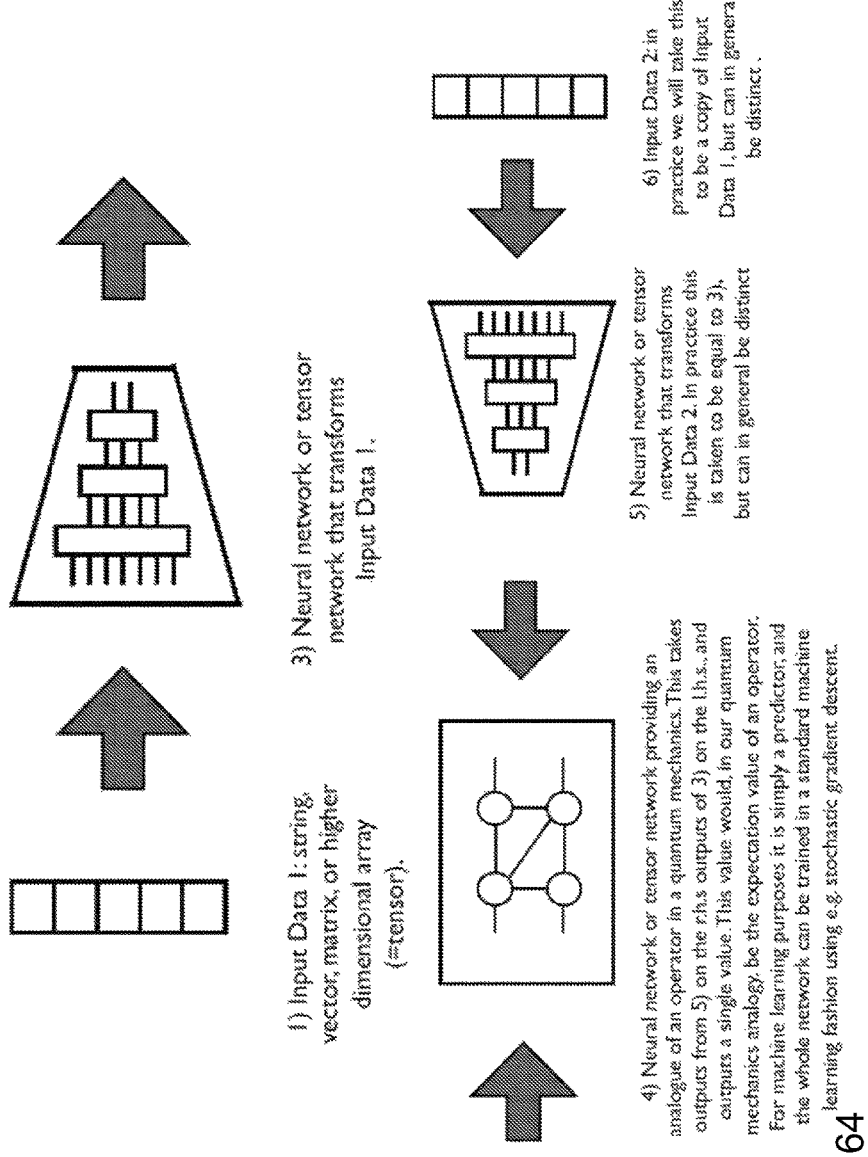
FIG. 64 shows a machine learning network inspired by the calculation of quantum operator expectation values.

The machine learning network inspired by the calculation of quantum operator expectation values is given in FIG. 64. In this manifestation, the input data is transformed by a neural network (or tensor network). A second copy of this input is then introduced, as well as an "operator" network. In order to compute the predictor, the operator network is sandwiched between the two input networks, similarly to the way the quantum operator O above is "sandwiched" between <x| and |x> in order to compute the expectation value of O. In other embodiments, the right and left inputs and networks do not need to be identical.

Therefore, the difference compared to a standard neural network, which takes an input and calculates some predictors as an output, is that here the predictor is obtained by taking two copies of an input, acting on these, separately, by a neural network, and finally sandwiching a third neural network between these in order to obtain the predictor. The "sandwiching" operation in our quantum-inspired neural network may be a vectorial dot product. More complex inputs and networks may alternatively or in addition be used, that can be represented as tensor networks, in which case the full machinery of tensor networks may be required in order to calculate the predictor. Further, implementing stochastic gradient descent may be more complex than doing standard back propagation for neural networks, since complex tensorial contractions may be involved. Defining the optimal computational graph to be used by back-propagation can become a highly non-trivial task.

Figure 65:
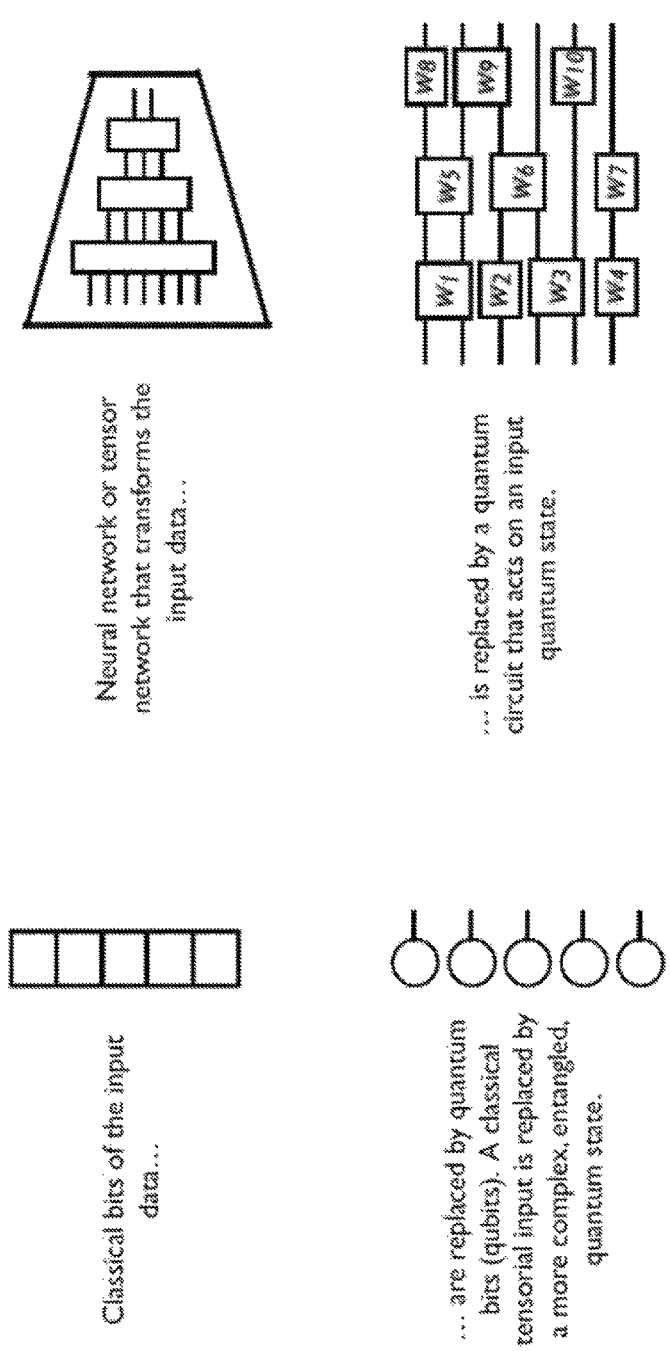
FIG. 65 shows the transformation of a classical network inspired by quantum mechanics into an arrangement that can be run on a quantum computer.

The main steps involved in transforming the classical network inspired by quantum mechanics as disclosed herein into an arrangement operable to be run on a quantum computer are given in FIG. 65. Specifically, the neural network that describe an action on the input is replaced by a quantum circuit. The input, if simply given by classical bits, is replaced by quantum bits ("qubits"). If the input is given by a tensor network, it is replaced by a corresponding non-separable (i.e. entangled) quantum state. Inference on the quantum computer algorithm is done by measuring an operator: the average value of our measurement yields the predictor value.

The adjustable parameters of gates, $w_1$ to $w_{10}$ in the diagram, are simply classical parameters. These may be optimised in a standard stochastic gradient routine to minimise a cost function of interest. The quantum part of the calculation determines the predictors, and the gradients for the gate parameters. The algorithm is therefore split into classical and quantum subroutines. The quantum subroutine deals with the calculation of the cost function and the gradients, whilst the updates of the parameters, and the rest of the stochastic gradient subroutine, are dealt with classically. The basic arrangement of splitting a gradient descent algorithm into quantum and classical parts addresses a machine learning problem, rather than purely wave function optimisation for a single molecule. The algorithm(s) and arrangement disclosed herein can be tested on computers that are not universal and do not have full quantum error correction implemented, for example the "IBM-Q" or the upcoming Google chipset (or the D-WAVE computer). Even though non-universal, future iterations of these machines may be capable of exploiting quantum entanglement that is not efficiently accessible classically. It has been inconclusively argued that this may be the case even for systems available at present. All accessible entanglement would, in principle, be utilised by the present approach, and there is be no requirement to understand details of decoherence effects or how to correct for these. The effects of decoherence may only be noticed in the lack of improvement for quantum circuits beyond a certain depth.

Generally, there is disclosed herein an arrangement to be run on a classical computer, and a further embodiment operable to be run on a quantum computer. A particular focus and use case of the disclosure herein may be regarding problems associated with searching spaces of possible small molecules in drug discovery. In such a case, inputs are descriptions of molecules and in some embodiments the approach described herein can be used to calculate predictors for molecules (or chemical compounds) such as toxicity, solubility and other properties. Current state of the art in machine learning applied to molecular data utilises simple molecular graphs as inputs, together with some standard per-atom features. Ultimately the correct description of a molecule is given by its full quantum wave function, and should be described by tensors. The networks that deal with such tensorial inputs may be mandated to respect this structure, and heavily reference tensor network machinery developed in physics.

The method disclosed herein may be operable to be quantum ready, so once quantum computers become available, it can be adopted to exploit quantum resources that are not efficiently accessible to classical computers.

Any system feature as described herein may also be provided as a method feature, and vice versa. As used herein, means plus function features may be expressed alternatively in terms of their corresponding structure.

Any feature in one aspect of the invention may be applied to other aspects of the invention, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

APPENDIX 6

Graph Generative Models

1 Overview of Existing Models

Generally deep generative models come in two flavours: likelihood-based (exemplified by VAE) and implicit (the main examples being GANs and reinforcement learning (RL) models). Likelihood-based models explicitly learn a distribution over the data space by learning the parameters of a distribution with some pre-set form (typically we assume a latent space with prior p(z), and the distribution takes the form $p(x|z)=N(f_\theta(z),1; x)$ where f_ is a neural network). Implicit methods define a prior p(z) and learn a mapping $x=G_\theta(z)$ such that the derived distribution $p(G_\theta(z))$ approximates the target distribution p(x).

VAEs (FIG. 51) consist of an encoder $q_\phi$ which maps samples from the target distribution to a latent vector, and a decoder $f_\theta$ which maps from latent space back to input space.

The model is trained to optimise reconstruction quality while minimising the amount of information passing through the latent space. Loosely, one can think of the model as learning a fuzzy submanifold on input space, where latent space is a coordinate system on that submanifold, and the decoder de_nes an embedding. Another view is in terms of description length: we are asking the encoder to describe the data as accurately as possible while using little information, which should encourage it to use the as much of latent space as possible to encode generalizable concepts. To optimise reconstruction quality, one must evaluate the model's distribution at data points from the training set, which presents a problem when learning on graph data, as we will see below.

GANs (FIG. 48) are easier to understand intuitively. They consist of a generator $G_\theta$_ and a discriminator $D_\phi$. The generator takes samples from some high-entropy distribution and maps them to the target space (in this case the space of graphs). The discriminator takes examples from the target space, either generated and real (i.e. from some dataset) with equal probability, and is trained to classify them as real or fake. The generator is trained to maximise the probability that its outputs are real according to the discriminator.

The majority of extant graph generative models are likelihood-based, and are heavily influenced by VAEs. These models are simpler to train than implicit models, which are infamously tricky and tend to put too much mass on a small set of peaks of the target distribution, a phenomenon also known as mode collapse. All current models, however, learn a distribution over labeled graphs, whereas ideally one would like to learn a distribution over unlabelled graphs, to maximise data density. This is due to the difficulty of representing a probability distribution over graphs in a way that is both independent of node ordering and easy to sample from at test-time. When training VAEs this problem manifests itself when comparing the output graph to the input graph.

Comparing unlabelled graphs means that all permutations of a certain output graph representation should be compared to the input graph, which is NP-hard and seems therefore to be infeasible.

Some models try to canonicalise the graph order, mapping each unlabelled graph to a labeled graph. This means that the representation of the data is highly dependent on the details of the ordering algorithm, which introduces effective discontinuities (so that e.g. small changes in the representation correspond to very different graphs). A consequence of this for the machine learning is that it can be difficult to train the models and/or that the resulting models generalise poorly.

The alternative is to learn the order of graphs explicitly, which extends the model complexity significantly. Seemingly, the most promising route to keep the model efficient is by using a permutation-covariant model architecture, necessitating a large permutation covariant latent space. Implicit models do not suffer from this problem since we can use an arbitrary function to estimate the density, and we are free to make this function invariant to node permutations.

A further design choice seems to consist of whether to generate the graph sequentially node by node (or edge by edge) or the entire graph at once. While sequential generation faces again the problem of ordering the nodes in the sequence, generating the entire graph at once usually means that each node and edge is generated independently and only depends on the latent variables. In other words, the probability distribution has to be of the form $$P(n_1, \ldots, n_N | z) = \prod_{i=1}^{N} P(n_i | z),$$

which restricts the model a lot. The generator has to decide for each node independently on which feature to assign, and can only impose constraints from chemistry a-posteriori, by discarding generated graphs. In contrast, sequential models can produce a distribution $$P(n_1, \ldots, n_N | z) = \prod_{i=1}^{N} P(n_i | n_{i-1}, \ldots, n_1, z),$$

which is a general probability distribution according to the product rule of statistics.

Most models treat all atoms as individual nodes, in chemistry it is clear however that certain larger structures occur regularly, for instance aromatic rings. A few models define larger building blocks that make it vastly easier to generate realistic molecules, which can lead to improved performance for molecules.

Below we give a couple of example models representing the current status of molecular graph generation. We first present a few likelihood-based graph generative models, then describe a molecular GAN and a RL graph generator. A summary overview of the models is given in Table 1 (FIG. 66).

1.1 GraphVAE (arXiv:1802.03480)

This is the most basic attempt at a VAE for graphs in the literature. The encoder is a graph convolutional neural network, and the decoder a 3-layer multi-linear perceptron (MLP), which means that the architecture is only capable of producing graphs with a fixed number of nodes. Edges and nodes are assumed to be independent given the latent point, and the decoder outputs a categorical distribution over each possible edge and each node, which defines a distribution over graphs. At test time, a graph is generated all at once by sampling from this distribution. This model therefore suffers from the problem with all-at-once generation mentioned above.

Using the model's output directly in the loss function is not optimal. The encoder destroys all information about the input's ordering, which in the absence of a canonical ordering for the data effectively makes learning impossible: if the model outputs the correct graph in the wrong order it is punished and moves away from that good behaviour.

Imposing a canonical ordering over the graphs is one option, but this forces the model to learn that ordering, which might be highly complex, along with the desired distribution over graphs. Instead, the authors use fuzzy graph matching to select the ordering for which the model gives the highest probability, and evaluate the distribution using that ordering. This guarantees that the loss is the same no matter what ordering the decoder chooses. Also, since the encoder is permutation invariant, the loss does not change with input ordering either. A potential problem with this approach is that the decoder is forced to arbitrarily select some ordering. It may learn different ordering schemes over different parts of latent space, and if this fractionation happens, examples which are decoded using one scheme are unlikely to update the model's weights in a way that is helpful when using other schemes, leading to an effective increase in data sparsity. The graph matching procedure is also computationally expensive and will not scale to larger graphs.

This model does not perform well in terms of proportion of valid molecules generated, and so ideas beyond this basic approach are needed.

1.2 Our Attempt

We attempted a VAE-based method which generates graphs all at once by having the decoder output a set of independent distributions over nodes and edges, similarly to the above model, but in which the encoder is not permutation invariant. This rids us of the need for graph matching: the model is able to encode the ordering along with the graph, and can therefore learn to place its mass on graphs with the correct ordering. As mentioned in the introduction, this entails a tradeoff: the model must learn a distribution over $\mathcal{G} \otimes \pi$. To mitigate this, we experimented with models that transform covariantly under permutations, so that for instance we have $$p_i(t|\mathcal{G}) = p_{\pi(i)}(t|\hat{\pi}\mathcal{G})$$

where pi is model's distribution over the ith node given the input graph $\mathcal{G}$, $\hat{\pi}$ is a node permuting operator, and $\pi(i)$ is the index of the node to which the ith node is mapped under $\hat{\pi}$. This comes with other advantages: it allows one to construct the model entirely from graph-convolutional networks without using any fully connected layers, which means we can deal with molecules of any size without changing the number of parameters.

Unfortunately the model in that form did not train at all. We do not yet understand why, but there's a step change in behaviour between permutation invariant models and non-invariant models: the non-invariant versions perform reasonably well but the invariant models don't learn at all, which suggests some underlying theoretical reason. Many of the non-invariant architectures we tried outperform Graph-VAE in terms of valid molecules generated, as well as being more computationally efficient and capable of dealing with arbitrary-size molecules.

1.3 Junction Tree Autoencoder (arXiv:1802.04364)

This is quite a complicated model. The training procedure is autoencoder-like in the sense that training examples are mapped to a latent space by a learned function $q_\_(x)$, from which a decoder produces a distribution $p_\theta(x|z)$, and the model's parameters are updated so as to increase the latter. The mapping $x \to z$ has a few stages: first, one reduces the graph to a tree using a fixed vocabulary of chemical structures comprised of rings and single atoms, so as to break cycles. Then a root node is chosen randomly, and features from the rest of the tree are propagated towards it; whenever a feature vector traverses an edge, it is multiplied by a matrix and the resulting vector is fed through a nonlinearity. These matrices are the learnable parameters of the encoder. Once all features have reached the root node, it is taken as the latent representation of the molecule input, and decoded into a distribution over graphs by something akin to the inverse of the encoding operation: essentially one assigns a probability to a procedure that produces the original graph starting from the root node by assigning probabilities to the actions that build up the graph one by one, based on the current state of the graph. This allows for training via teacher forcing. It also allows one to check the molecule for chemical validity at every step, and to forbid the model from taking any step leading to an invalid molecule; therefore even the untrained network always produces valid molecules, and more (but not all, see below) statistical power goes into learning the distribution of molecular properties in the dataset.

The models suffers from the node-ordering issue mentioned above: to learn to assign high probability to the actions that create the original graph, one is forced to pick some \correct" graph-construction procedure (or equivalently a \correct" node ordering).

Once trained, one can search the latent space using Bayesian optimization. Function evaluation consists of sampling a root-node vector, constructing a graph probabilistically according to the model, computing the score for the resulting molecule using some predictive model.

The authors report a reconstruction score (proportion of molecules that decode to themselves) of 76.6%. Assuming the molecules they tested this on were not seen during training (they don't mention this explicitly), this is an encouraging score, the best reported so far on the task. The molecules it produces look druglike enough. The regularity of the latent representation looks questionable however:

taking small steps in latent space can significantly change the decoded molecule, which isn't ideal for search/optimization.

1.4 Constrained Graph VAEs (1805.09076)

This algorithm is also VAE-like. The encoder is a truncated graph-convolutional neural network—truncated in the sense that it lacks the usual fully-connected \head", which would make the encoder invariant under node permutations. Such invariance is undesirable, since it forces us to use a learnable canonical node ordering (not obviously possible for larger graphs with many node types), and the model would have to waste statistical power on learning that ordering. Instead, the authors take only the convolutional layers of a graph convolutional neural network (GCNN) as the encoder, resulting in a "per-node" latent space. This at least allows for an architecture where the training updates do not depend on the input ordering (as would inevitably be the case with a permutation-invariant latent space). However, the extent to which this approach allows the model to focus its attention on learning a distribution over graphs rather than graphs cross permutations is unclear.

As with JTVAE, the decoder constructs the graph sequentially and trains via teacher forcing. This actually reintroduces the ordering problem that the per-node latent space went some way towards solving, since we now have to care about the order in which the graph is constructed. The authors solve this with Monte-Carlo: the loss function is formed using a sample from the set of all possible ways of constructing the ground-truth graph. This seems to be a general trend with these VAE-like models; people are willing to pay the price of ordering-ambiguity in order to gain the extra model capacity that comes with sequential decoding and, probably more importantly, to be able to force the model to produce valid molecules by enforcing validity at every step.

In order to do optimisation, the VAE is jointly trained with a predictive model on the latent space. Joint training makes sense in this context as the encoder sees the predictive model's loss, and so will learn an encoding that allows for predictability, and therefore hopefully optimisability. At test time, a latent space point is chosen according to the prior and gradient ascent of the predictive function is performed starting from the sampled point. From the paper it's not clear how well this works, but they present a couple of examples of optimisation trajectories where it does work.

1.5 MolGAN (1805.11973)

A GAN where the discriminator is a (full, permutation-invariant) GCNN, and the generator is a simple three-layer fully-connected network. Clearly this setup avoids the ordering problem since the discriminator loss is permutation-invariant. The only non-straightforward thing here is backpropagating through the generator-discriminator interface. The problem is that, unlike images, chemicals cannot be created by directly mapping from a sample in latent space (because they are represented in a discrete fashion in terms of node vectors and adjacency matrices). The best one can do is to map from latent space to a distribution over nodes and adjacency matrices, from which one must sample in order to obtain the _nal, discrete object—which is then passed through the discriminator.

Backpropagating through samples is usually not a problem in ML (e.g. just use the reparameterisation trick like in a VAE) but it is a problem if the domain of the distribution is discrete, as is the case at the input of the discriminator in a GAN. The paper mentions a couple of workarounds (although it doesn't say which it actually uses): treating node vectors and adjacency matrices as continuous objects and hoping that the generator will learn to limit its distribution to a discrete set of points; and having the generator produce discrete samples but backpropagating through them as though they were samples from a continuous distribution (in this case Gumbel-softmax, which, crucially, can be parameterised with the same parameters as the categorical distribution from which the molecule was actually sampled).

Optimisation here uses reinforcement learning (RL) as outlined in section 2. The reward is generated by a non-differentiable standard chemoinformatics model, which is allowed because RL does not require the reward function to be differentiable. RL success fully guides the GAN towards producing molecules with the correct properties; however, the learned distribution both with and without RL is severely mode-collapsed: very few unique molecules are generated; the model repeats the same few over and over. This seems to be a particularly severe case of a problem known to be endemic to GANs. In this case it is particularly bad. A possible explanation is the design choice mentioned above of the model to generate non-sequentially from a continuous distribution. Each node is sampled from the distribution independently of the other nodes. Generically this will lead to a lot of samples that might violate rules of chemistry and therefore can be easily spotted by the discriminator network. Finding probabilities that are close to deterministic can overcome that problem but inevitably lead to mode collapse.

1.6 Graph Convolutional Policy Network (1806.02473)

This algorithm builds molecular graphs sequentially using reinforcement learning.

The policy network consists of two parts, a standard GCNN encoding in a "per-node" latent space that is similar to the constrained graph VAE, and fully connected layers that take those latent space representation of nodes as input and output probabilities that decide which node gets a new edge to either another existing node or to a new node that comes out of a set of possible building blocks. The authors chose for the latter only individual atoms, but the algorithm is exible enough to also allow larger building blocks, using the same "per-node" GCNN to parameterise such building blocks in latent space.

The reward structure features a GAN, whose discriminator is a standard GCNN that is tasked to discriminate between the generated molecules and molecules in a given data set. Additional rewards (and penalties) are given for (not) obeying valence rules to steer the generator towards realistic molecules during generation, and other unrealistic features can be penalised at the end of episodes. Tweaking the algorithm to generate molecules that optimise certain properties is relatively simple, as relevant property scores can easily be implemented in the reward system as an incentive. Policy updates are done using proximal policy optimisation, which ensures exploration of the large space of molecules and might be the reason that there does not seem to be any problem with mode collapse.

Like MolGAN, the GCPN algorithm avoids any problem related to reordering between molecules, since the reward system of RL is completely insensitive to resulting nodes.

The model seems very successful in finding molecules with high targeted scores or with scores similar to a desired value, as well as doing constraint searches where one restricts to molecules that have certain components.

Note

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

The invention claimed is:

1. A quantum circuit based system configured to model drug-like molecules, in which one or more quantum circuits are configured as an infinite tensor network representation of quantum states of the drug-like molecules;
   in which an infinite tensor network is used to represent a repeating crystal structure of the drug-like molecules with a naturally repeating structure;
   and in which the quantum circuit based system is configured to determine or predict chemical properties for candidate drug-like molecules.

2. The quantum circuit based system of claim 1 that is implemented using a machine learning system.

3. The quantum circuit based system of claim 2, in which the machine learning system is a quantum machine learning circuit based on the infinite tensor network, obtained by embedding infinite tensors in networks into unitary gates.

4. The quantum circuit based system of claim 1, implemented using quantum computers with quantum circuits configured as infinite tensor networks.

5. The quantum circuit based system of claim 4, in which the quantum circuits are configured as an infinite tensor network representation of a classical system with the naturally repeating structure.

6. The quantum circuit based system of claim 1, in which a quantum circuit or a classical tensor network simulation is used for calculating an environment of the infinite tensor network.

7. The quantum circuit based system of claim 6, in which a quantum algorithm is used to predict a property, such as energy density or an expectation value of an operator, of the drug-like molecules.

8. The quantum circuit based system of claim 6, in which a quantum algorithm is used to optimise a cost function or a machine learning inspired cost function that has been trained on a periodic system.

9. The quantum circuit based system of claim 1, in which a property of the infinite tensor network including an environment is computed and tuned by sampling an output of a quantum circuit configured as the infinite tensor network.

10. The quantum circuit based system of claim 1, configured to predict or determine one or more of: energy transfer, organic LED and photovoltaic material properties, light absorption properties, melting point, and permeability associated with the drug-like molecules.

11. The quantum circuit based system of claim 1, configured to calculate energy densities or other properties of the drug-like molecules.

12. The quantum circuit based system of claim 1, configured to predict possible crystal structures of a solid and associated probabilities.

13. The quantum circuit based system of claim 1, configured to predict quantities based on crystal structures associated with the drug-like molecules.

14. The quantum circuit based system of claim 1, configured to simulate and calculate energies of excited states of the drug-like molecules.

15. A drug-like molecule identified, selected or optimized using the quantum circuit based system of claim 1.

16. A material or other substance identified, selected or optimized using the quantum circuit based system of claim 1.

17. A computer implemented method of modeling drug-like molecules, including a step of configuring one or more quantum circuits as an infinite tensor network representation of quantum states of the drug like molecules;
   in which an infinite tensor network is used to represent a repeating crystal structure of the drug-like molecules with a naturally repeating structure;
   and in which a quantum circuit based system is configured to determine or predict chemical properties for candidate drug-like molecules.

* * * * *